(12) United States Patent
Scola et al.

(10) Patent No.: US 7,135,462 B2
(45) Date of Patent: Nov. 14, 2006

(54) HEPATITIS C VIRUS INHIBITORS

(75) Inventors: Paul Michael Scola, Glastonbury, CT (US); Jeffrey Allen Campbell, Glen Gardner, NJ (US); Ny Sin, East Hampton, CT (US); Li-Qiang Sun, Glastonbruy, CT (US); Xiangdong Alan Wang, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/992,548

(22) Filed: Nov. 18, 2004

(65) Prior Publication Data

US 2005/0267040 A1    Dec. 1, 2005

Related U.S. Application Data

(60) Provisional application No. 60/523,717, filed on Nov. 20, 2003.

(51) Int. Cl.
A61K 38/00 (2006.01)
(52) U.S. Cl. ........................................................ 514/18
(58) Field of Classification Search ................. 530/331
See application file for complete search history.

(56) References Cited

U.S. PATENT DOCUMENTS

| | | | |
|---|---|---|---|
| 5,633,388 A | 5/1997 | Diana et al. | |
| 5,866,684 A | 2/1999 | Attwood et al. | |
| 5,869,253 A | 2/1999 | Draper et al. | |
| 6,018,020 A | 1/2000 | Attwood et al. | |
| 6,225,284 B1 | 5/2001 | Albert et al. | |
| 6,265,380 B1 | 7/2001 | Tung et al. | |
| 6,268,207 B1 | 7/2001 | Bailey et al. | |
| 6,323,180 B1 | 11/2001 | Llinas-Brunet et al. | |
| 6,410,531 B1 | 6/2002 | Llinas-Brunet et al. | |
| 6,420,380 B1 | 7/2002 | Llinas-Brunet et al. | |
| 6,534,523 B1 | 3/2003 | Llinas-Brunet et al. | |
| 6,642,204 B1 | 11/2003 | Llinas-Brunet et al. | |
| 6,869,964 B1 | 3/2005 | Campbell et al. | |
| 6,872,805 B1 | 3/2005 | Campbell et al. | |
| 6,878,722 B1 | 4/2005 | Campbell et al. | |
| 6,919,423 B1* | 7/2005 | Llinas-Brunet ............ | 514/18 |
| 2002/0111313 A1* | 8/2002 | Campbell et al. ............ | 514/18 |
| 2004/0048802 A1 | 3/2004 | Ripka et al. | |
| 2004/0077551 A1* | 4/2004 | Campbell et al. ............ | 514/18 |

FOREIGN PATENT DOCUMENTS

| | | |
|---|---|---|
| EP | 1162196 A1 | 12/2000 |
| WO | WO 95/33764 | 12/1995 |
| WO | WO 97/06804 | 2/1997 |
| WO | WO 97/43310 | 11/1997 |
| WO | WO 98/17679 | 4/1998 |
| WO | WO 98/22496 | 5/1998 |
| WO | WO 98/46597 | 10/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/06529 | 2/2000 |
| WO | WO 00/09543 | 2/2000 |
| WO | WO 00/09558 | 2/2000 |
| WO | WO 00/10573 | 3/2000 |
| WO | WO 00/13708 | 3/2000 |
| WO | WO 00/18231 | 4/2000 |
| WO | WO 00/59929 | 10/2000 |
| WO | WO 01/32153 A2 | 5/2001 |
| WO | WO 01/85172 A1 | 11/2001 |
| WO | WO 02/04425 A2 | 1/2002 |
| WO | WO 02/06246 A1 | 1/2002 |
| WO | WO 02/060926 A2 | 8/2002 |
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |
| WO | WO 03/099274 | 12/2003 |
| WO | WO 03/099316 | 12/2003 |
| WO | WO 2004/032827 | 4/2004 |
| WO | WO 2004/043339 | 5/2004 |
| WO | WO 2005/046712 | 5/2005 |

OTHER PUBLICATIONS

U.S. Appl. No. 10/985,106, filed Nov. 10, 2004, Scola et al.

(Continued)

*Primary Examiner*—Bruce R. Campell
*Assistant Examiner*—Thomas S. Heard
(74) *Attorney, Agent, or Firm*—Pamela A. Mingo; Warren K. Volles

(57) ABSTRACT

Hepatitis C virus inhibitors are disclosed having the general formula:

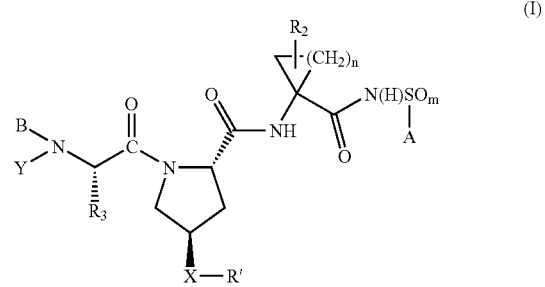

wherein A, $R_2$, $R_3$, R', B and Y are described in the description. Compositions comprising the compounds and methods for using the compounds to inhibit HCV are also disclosed.

54 Claims, No Drawings

OTHER PUBLICATIONS

U.S. Appl. No. 10/992,566, filed Nov. 18, 2004, Tu et al.

Lauer, G. M. et al., "Hepatitis C Virus Infection," The New England Journal of Medicine, vol. 345, No. 1, pp. 41-52 (2001).

Zeuzem, S. et al., "Peginterferon Alfa-2a in Patients with Chronic Hepatitis C," The New England Journal of Medicine, vol. 343, No. 23, pp. 1666-1672 (2000).

Poynard, T. et al., "Randomised trial of interferon α2b plus ribavirin for 48 weeks or for 24 weeks versus interferon α2b plus placebo for 48 weeks for treatment of chronic infection with hepatitis C virus," The Lancet, vol. 352, pp. 1426-1432 (1998).

Poupart et al., "Solid-Phase Synthesis of Peptidomimetic Inhibitors for the Hepatitis C Virus NS3 Protease," The Journal of Organic Chemistry, vol. 66, No. 14, pp. 4743-4751 (2001).

Steinkuhler et al., "Product Inhibition of the Hepatitis C Virus NS3 Protease," Biochemistry, vol. 37, pp. 8899-8905 (1998).

Ingallinella et al., "Potent Peptide Inhibitors of Human Hepatitis C Virus NS3 Protease Are Obtained by Optimizing the Cleavage Products," Biochemistry, vol. 37, pp. 8906-8914 (1998).

Chu et al., "Structure of Sch 68631: A New Hepatitis C Virus Proteinase Inhibitor from Streptomyces sp.," Tetrahedron Letters, vol. 37, No. 40, pp. 7229-7232 (1996).

Matsumoto et al., "3D Modeling of HCV Protease and Computer Screening of its Inhibitors," Antiviral Research, vol. 30, No. 1, pp. A23, Abstract 19 (1996).

\* cited by examiner

HEPATITIS C VIRUS INHIBITORS

CROSS REFERENCE TO RELATED APPLICATION

This non-provisional application claims priority from the provisional application U.S. Ser. No. 60/523,717 filed Nov. 20, 2003.

FIELD OF THE INVENTION

The present invention is generally directed to antiviral compounds, and more specifically directed to compounds which inhibit the functioning of the NS3 protease (also referred to herein as "serine protease") encoded by Hepatitis C virus (HCV), compositions comprising such compounds and methods for inhibiting the functioning of the NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. *N. Engl. J. Med.* (2001), 345, 41–52).

Presently, the most effective HCV therapy employs a combination of alpha-interferon and ribavirin, leading to sustained efficacy in 40% of patients. (Poynard, T. et al. *Lancet* (1998), 352, 1426–1432). Recent clinical results demonstrate that pegylated alpha-interferon is superior to unmodified alpha-interferon as monotherapy (Zeuzem, S. et al. *N. Engl. J. Med.* (2000), 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to cleave at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the peptide compounds disclosed in U.S. Pat. No. 6,323,180.

SUMMARY OF THE INVENTION

The present invention provides compounds of formula I;

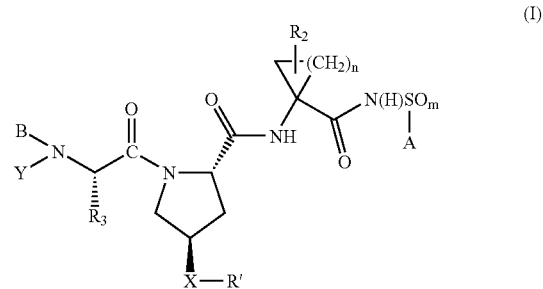

(I)

wherein:
(a) A is

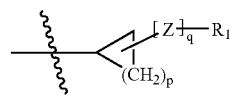

z is

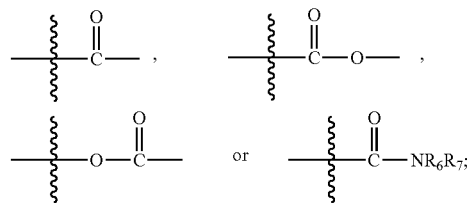

p is 1, 2 or 3;
q is 0 or 1;
$R_1$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;
or $R_1$ is trialkylsilane or halogen, provided q is 0;

(b) m is 1 or 2;
(c) n is 1 or 2;
(d) $R_2$ is H, $C_{1-6}$ alkyl, $C_{2-6}$ alkenyl or $C_{3-7}$ cycloalkyl, each optionally substituted with halogen;
(e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;
(f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;
(g) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;
(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalkyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo(1.1.1)pentane; or (vi) —C(O)O$C_{1-6}$ alkyl, $C_{2-6}$alkenyl or $C_{2-6}$ alkynyl;
(i) $R_5$ is H; $C_{1-6}$ alkyl optionally substituted with 1–3 halogens; or $C_{1-6}$ alkoxy provided $R_4$ is $C_{1-10}$ alkyl;
(j) X is O, S, SO, $SO_2$, $OCH_2$, $CH_2O$ or NH;
(k) R' is Het, $C_{6-10}$ aryl or $C_{7-14}$ alkylaryl, each optionally substituted with $R^a$; and
(l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di ($C_{1-6}$) alkyl(alkoxy)amine, $C_{6-10}$ aryl, $C_{7-14}$ alkylaryl, or a 5–7 membered monocyclic heterocycle; and
(m) $R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl;

or a pharmaceutically acceptable enantiomer, diastereomer, salt, solvate or prodrug thereof.

The present invention also provides compositions comprising the compounds or pharmaceutically acceptable salts, solvates or prodrugs thereof and a pharmaceutically acceptable carrier. In particular, the present invention provides pharmaceutical compositions useful for inhibiting HCV NS3 comprising a therapeutically effective amount of a compound of the present invention, or a pharmaceutically acceptable salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable salt, solvate or prodrug thereof. Additionally, the present invention provides methods of inhibiting HCV NS3 protease by contacting the NS3 protease with a compound of the present invention.

By virute of the present invention, it is now possible to provide improved drugs comprising the compounds of the invention which can be effective in the treatment of patients infected with HCV. Specifically, the present invention provides peptide compounds that can inhibit the functioning of the NS3 protease, e.g., in combination with the NS4A protease. Further, the present invention makes it possible to administer combination therapy to a patient whereby a compound in accordance with the present invention, which is effective to inhibit the HCV NS3 protease, can be administered with another compound having anti-HCV activity, e.g., a compound which is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

DETAILED DESCRIPTION OF THE INVENTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture. With reference to the instances where (R) or (S) is used, it is to designate the absolute configuration of a substituent in context to the whole compound and not in context to the substituent alone.

Unless otherwise specifically noted herein, the terms set forth below will have the following definitions.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of formula I, and pharmaceutically acceptable enantiomer, diastereomer salts, and solvates, e.g. hydrates, and prodrugs. Similarly, references to intermediates, are meant to embrace their salts, and solvates, where the context so permits. References to the compound of the invention also include the preferred compounds, e.g. formula II and A–M.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.p., organic radical, to which the subsitutent is bonded, e.g., mono-, di-, tri- or tetra-substituted, unless otherwise specifically stated.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine or arylalkyl, include all possible stable configurations, unless otherwise specifically stated. Certain radicals and combinations are defined below for purposes of illustration.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents having the specified number of carbon atoms and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralkyl" mean an aryl group substituted with one or more alkyl groups. Unless the carbon range of each group is specified, the stated range applies to the entire substituent. Thus, a $C_{7-14}$ alkylaryl group many have from 1–8 carbon atoms in the alkyl group for a monocyclic aromatic and from 1–4 carbon atoms in the alkyl group for a fused aromatic. The attachment of the group to bonding site on the molecule can be either at the aryl group or the alkyl group. Unless a specific aryl radical is specified, e.g., fluoro-phenyl, or the radical is stated to be unsubstituted, the aryl radicals include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "alkylamide" as used herein means an amide mono-substituted with an alkyl, such as

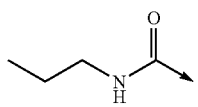

The term "heterocycle", also referred to as "Het", as used herein means 7–12 membered bicyclic heterocycles and 5–9 membered monocyclic heterocycles.

Preferred bicyclic heterocycles are 7–12 membered fused bicyclic ring systems (both rings share an adjacent pair of atoms) containing from one to four heteroatoms selected from nitrogen, oxygen and sulfur, wherein one or both rings of the heterocycle can be saturated, partially saturated or fully unsaturated ring system (this latter subset also herein referred to as unsaturated heteroaromatic). The nitrogen and sulfur heteroatoms atoms may be optionally oxidized. The bicyclic heterocycle may contain the heteroatoms in one or both rings. Unless a specific heterocycle is specified, e.g., a fluorinated 7–12 membered bicyclic heterocycle, or the heterocycle is stated to be unsubstituted, the heterocycles include those substituted with typical substituents known to those skilled in the art. For example, the bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di $(C_{1-6})$ alkylamino, di $(C_{1-6})$ alkylamide, carboxyl, $(C_{1-6})$ carboxyester, $C_{1-6}$ alkylsulfone, $C_{1-6}$ alkylsulfonamide, $C_{1-6}$ alkylsulfoxide, di $(C_{1-6})$ alkyl (alkoxy)amine, $C_{6-10}$ aryl, $C_{7-14}$ alkylaryl, and a 5–7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen. The bicyclic heterocycle may be attached to the molecule, e.g. $R_1$ in formula I, at any atom in the ring and preferably carbon.

Examples of bicyclic heterocycles include, but are not limited to, the following ring systems:

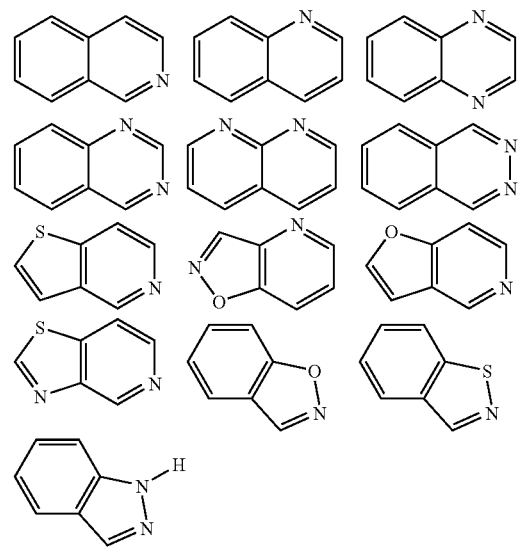

Preferred monocyclic heterocycles are 5–9 membered saturated, partially saturated or fully unsaturated ring system (this latter subset also herein referred to as unsaturated heteroaromatic) containing in the ring from one to four heteroatoms selected from nitrogen, oxygen and sulfur, wherein the sulfur and nitrogen heteroatoms may be optionally oxidized. Unless a specific heterocycle is specified, e.g., a $C_{1-6}$ alkoxy substituted 5–7 membered monocyclic heterocycle, or the heterocycle is stated to be unsubstituted, the heterocycles include those substituted with typical substituents known to those skilled in the art. For example, the monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di $(C_{1-6})$ alkylamino, di $(C_{1-6})$ alkylamide, carboxyl, $(C_{1-6})$ carboxyester, $C_{1-6}$ alkylsulfone, $C_{1-6}$ alkylsulfoxide, $C_{1-6}$ alkylsulfonamide, di ($C_{1-6}$) alkyl(alkoxy)amine, $C_{6-10}$ aryl, $C_{7-14}$ alkylaryl and an additional 5–7 membered monocyclic heterocycle. The monocyclic heterocycle may be attached to the molecule, e.g. $R_1$ in formula I, at any atom in the ring.

Examples of monocyclic heterocycles include, but are not limited to, the following (and their tautomers):

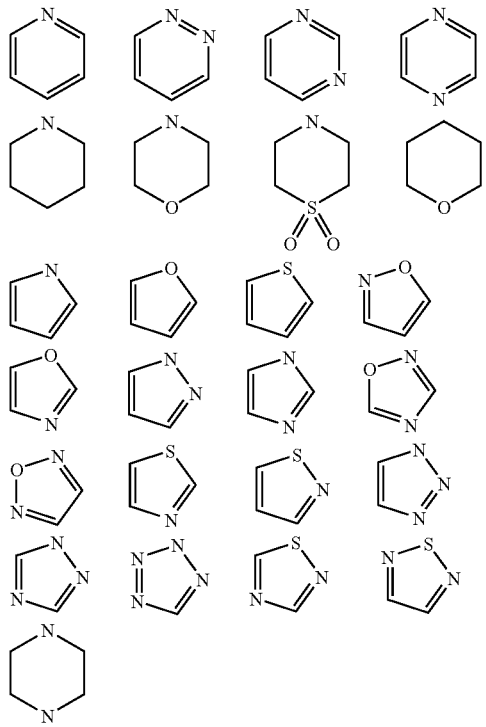

Those skilled in the art will recognize that the heterocycles used in the compounds of the present invention should be stable. Generally, stable compounds are those which can be synthesized, isolated and formulated using techniques known the those skilled in the art without degradation of the compound.

The term "substituent" with reference to an amino acid or amino acid derivative means a radical derived from the corresponding α-amino acid. For instance, the substituents methyl, iso-propyl, and phenyl represent the amino acids alanine, valine, and phenyl glycine, respectively.

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.)(see Berger A. & Schechter I., Transactions of the Royal Society London series (1970), B257, 249–264].

As used herein the term "1-aminocyclopropyl-carboxylic acid" (Acca) refers to a compound of formula:

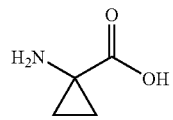

As used herein the term "tert-butylglycine" refers to a compound of the formula:

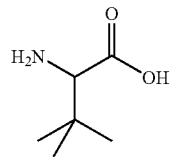

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The compounds of the present invention have the structure of Formula I:

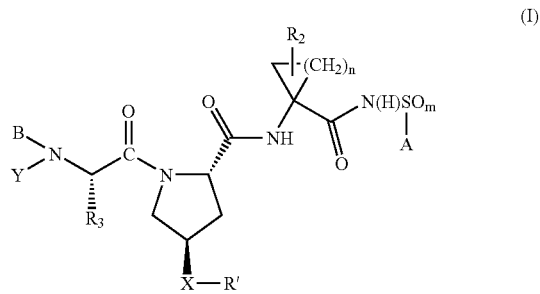

wherein:

(a) A is

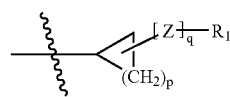

z is

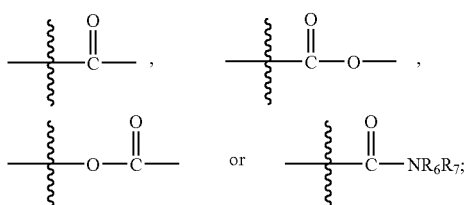

p is 1, 2 or 3;
q is 0 or 1;
$R_1$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het; or $R_1$ is trialkylsilane or halogen, provided q is 0;
(b) m is 1 or 2;
(c) n is 1 or 2;
(d) $R_2$ is H, $C_{1-6}$ alkyl, $C_{2-6}$ alkenyl or $C_{3-7}$ cycloalkyl, each optionally substituted with halogen;
(e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;
(f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;
(g) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;
(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy or $C_{4-10}$ alkylcycloaklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo(1.1.1)pentane; or (vi) —C(O)OC$_{1-6}$alkyl, $C_{2-6}$alkenyl or $C_{2-6}$ alkynyl;
(i) $R_5$ is H; $C_{1-6}$ alkyl optionally substituted with 1–3 halogens; or $C_{1-6}$ alkoxy provided $R_4$ is $C_{1-10}$ alkyl;
(j) X is O, S, SO, $SO_2$, OCH$_2$, CH$_2$O or NH;
(k) R' is Het, $C_{6-10}$ aryl or $C_{7-14}$ alkylaryl, each optionally substituted with $R^a$; and
(l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di ($C_{1-6}$) alkyl(alkoxy)amine, $C_{6-10}$ aryl, $C_{7-14}$ alkylaryl, or a 5–7 membered monocyclic heterocycle; and
(m) $R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl;

or a pharmaceutically acceptable enantiomer, diastereomer, salt, solvate or prodrug thereof.

In a preferred aspect of the invention, A is

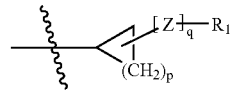

z is

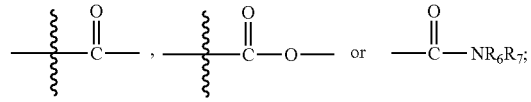

p is 1, 2 or 3;
q is 0 or 1;
$R_1$ is $C_{3-7}$ cycloalkyl, $C_{4-7}$ cycloalkenyl; $C_{7-14}$ alkylaryl; $C_{7-14}$ alkylaryloxy; $C_{8-15}$ alkylarylester; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{6-10}$ aryloxy, $C_{8-15}$ alkylarylester or Het; or $R_1$ is trialkylsilane or halogen, provided q is 0; and
$R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl.

Preferably, $R_2$ is $C_{1-6}$ alkyl, $C_{2-6}$ alkenyl or $C_{3-7}$ cycloalkyl. More preferably, $R_2$ is $C_{2-6}$ alkenyl. Preferably, $R_3$ is $C_{1-8}$ alkyl optionally substituted with $C_6$aryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl; or $C_{4-10}$ alkylcycloalkyl. More preferably, $R_3$ is $C_{1-8}$ alkyl optionally substituted with $C_{1-6}$ alkoxy; or $C_{3-7}$ cycloalkyl.

Preferably, Y is H. Preferably, B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—. More preferably, B is $R_4$—(C=O)—, $R_4O(C=O)$—, or $R_4$—N($R_5$)—C(=O)—. Even more preferably, B is $R_4O(C=O)$— and $R_4$ is $C_{1-6}$ alkyl. Preferably, $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen. More preferably, $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl. Preferably, $R_5$ is H or $C_{1-6}$ alkyl optionally substituted with 1–3 halogens. More preferably, $R_5$ is H.

Preferably, X is O or NH. Preferably, R' is Het; or $C_{6-10}$ aryl optionally substituted with $R^a$. More preferably, R' is Het. Preferably, the heterocycle contains 1 or 2 nitrogen atoms and optionally a sulfur atom or an oxygen atom in the ring. More preferably, the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle. Preferably, $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle.

The substituents from each grouping may be selected individually and combined in any combination which provides a stable compound in accordance with the present invention. Also, more than one substituent from each group may be substituted on the core group provided there are sufficient available binding sites. For example, each of the following $R_6$, $R_7$, $R_8$ or $R_9$ substituents, $C_{1-6}$ alkoxy, $C_6$ aryl and a 5–7 membered monocyclic heterocycle, may be substituted on a bicyclic heterocycle.

In a preferred aspect, the compounds of the present invention have the structure of Formula II:

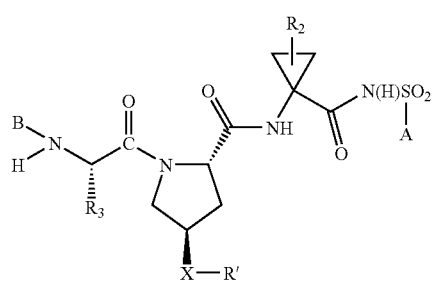
(II)

wherein:
(a) A is

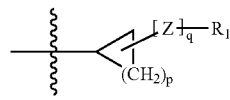

z is

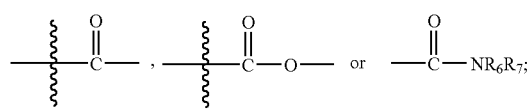

p is 1, 2 or 3;
q is 0 or 1; and
$R_1$ is $C_{3-7}$ cycloalkyl, $C_{4-7}$ cycloalkenyl; $C_{7-14}$ alkylaryl; $C_{7-14}$ alkylaryloxy; $C_{8-15}$ alkylarylester; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{6-10}$ aryloxy, $C_{8-15}$ alkylarylester or Het; or $R_1$ is trialkylsilane or halogen, provided q is 0;
(b) $R_2$ is $C_{1-6}$ alkyl, $C_{2-6}$ alkenyl or $C_{3-7}$ cycloalkyl;
(c) $R_3$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl;
(d) Y is H;
(e) B is H, $C_{1-6}$ alkyl, $R_4$—(C=O)—, $R_4$O(C=O)—, $R_4$—N($R_5$)—C(=O)—, $R_4$—N($R_5$)—C(=S)—, $R_4SO_2$—, or $R_4$—N($R_5$)—$SO_2$—;

(f) $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalkyl; or (iii) $C_{6-10}$ aryl or $C_{7-16}$ arylalkyl, each optionally substituted with $C_{1-6}$ alkyl or halogen;
(g) $R_5$ is H or $C_{1-6}$ alkyl optionally substituted with 1–3 halogens;
(h) X is O or NH;
(i) R' is Het; or $C_{6-10}$ aryl optionally substituted with $R^a$;
(j) $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle; and
(k) $R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl;

or a pharmaceutically acceptable enantiomer, diastereomer salt, solvate or prodrug thereof.

Preferably, R' is a bicyclic heterocycle. Preferably, the heterocycle contains 1 or 2 nitrogen atoms and optionally a sulfur atom or an oxygen atom in the ring. More preferably, the heterocycle is substituted with at least one of $C_{1-6}$ alkyl, $C_{1-6}$ alkoxy, halo, $C_6$ aryl, and a 5–7 membered monocyclic heterocycle.

In one aspect of the invention, R' is a bicyclic heterocycle containing 1 nitrogen atom and substituted with methoxy and at least one of a $C_6$ aryl and a 5–7 membered monocyclic heterocycle.

In another aspect of the invention, R' is a monocyclic heterocycle. Preferably, the heterocycle contains 1 or 2 nitrogen atoms and optionally a sulfur atom or an oxygen atom in the ring. Even more preferably, the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle. In an especially preferred aspect of the invention, R' is a monoyclic heterocycle containing 1 or 2 nitrogen atoms and substituted with methoxy and at least one of a $C_6$ aryl and a 5–7 membered monocyclic heterocycle.

In a more preferred aspect of the invention, the compounds have the structure of Formula III

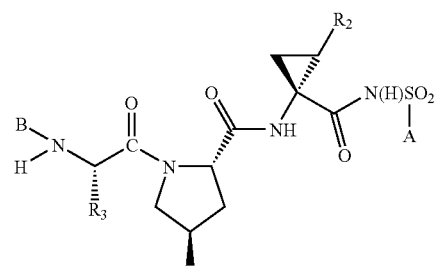
(III)

wherein:
(a) A is

p is 1, 2 or 3;

$R_1$ is $C_{7-14}$ alkylaryl; $C_{1-8}$ alkyl optionally substituted with $C_{1-6}$ alkoxy, $C_{2-10}$ alkenyl or $C_{4-10}$ alkylcycloalkyl; or $R_1$ is trialkylsilane or halogen;

(b) $R_2$ is $C_{2-6}$ alkenyl;

(c) $R_3$ is $C_{1-8}$ alkyl;

(d) B is $R_4O(C=O)$—, or $R_4$—N(H)—C(=O)—;

(e) $R_4$ is $C_{1-10}$ alkyl;

(f) R' is a bicyclic heterocycle optionally substituted with $R^a$; and (g) $R^a$ is $C_{1-6}$ alkyl, $C_{1-6}$ alkoxy, halo, $C_6$ aryl, or a 5–7 membered monocyclic heterocycle;

or a pharmaceutically acceptable enantiomer, diastereomer salt, solvate or prodrug thereof.

Preferably, $R_1$ is cyclopropyl or cyclobutyl, $R_2$ is vinyl, $R_3$ is t-butyl and $R_4$ is t-butyl. Preferably, R' is quinoline or isoquinoline optionally substituted with $R^a$. Preferbly, $R^a$ is $C_{1-6}$alkoxy. More preferably, $R^a$ further includes at least one of $C_6$ aryl or a 5–7 membered monocyclic heterocycle.

The compounds of the present invention, which are substituted with a basic group, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The compounds of the present invention also contain two or more chiral centers. For example, the compounds may include P1 cyclopropyl element of formula

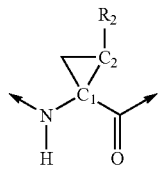

P1 wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R_2$ is configured either syn to the amide or syn to the carbonyl as shown below.

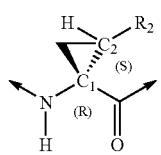

(1R, 2S)
$R_2$ is syn to carbonyl

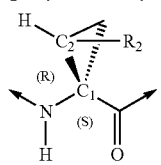

(1S, 2R)
$R_2$ is syn to carbonyl

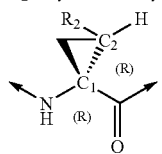

(1R, 2R)
$R_2$ is syn to amide

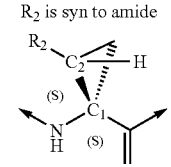

(1S, 2S)
$R_2$ is syn to amide

The present invention includes both enantiomers and mixtures of enantiomers such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent.

It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy) alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art, see e.p., U.S. Pat. No. 6,323,180 and U.S. Patent Appl. 20020111313 A1. The following methods set forth below are provided for illustrative purposes and are not intended to limit the scope of the claimed invention. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

The compounds of the present invention may, for example, be synthesized according to a general process as illustrated in Scheme I (wherein CPG is a carboxyl protecting group and APG is an amino protecting group):

Scheme I

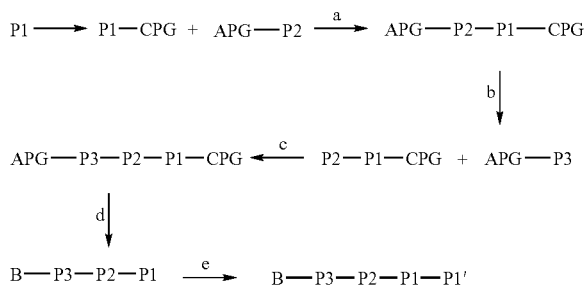

Briefly, the P1, P2, and P3 can be linked by well known peptide coupling techniques. The P1, P2, and P3 groups may be linked together in any order as long as the final compound corresponds to peptides of the invention. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (ρ-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N, N',N'-tetramethyluronium tetrafluoroborate. Still another practical and useful coupling agent is commercially available O-(7-azabenzotrizol-1-yl)-N,N,N', N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and ρ-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6)trialkylsilyl such as trimethylsilyl; and 7) thiol containing groups such as phenylthiocarbonyl and dithiasuccinoyl.

The preferred α-amino protecting group is either Boc or Fmoc. Many amino acid derivatives suitably protected for peptide synthesis are commercially available. The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; bencyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

Further, the following guidance may be followed in the preparation of compounds of the present invention. For example, to form a compound where $R_4$—C(O)—, $R_4$—S(O)$_2$, a protected P3 or the whole peptide or a peptide segment is coupled to an appropriate acyl chloride or sulfonyl chloride respectively, that is either commercially available or for which the synthesis is well known in the art.

In preparing a compound where $R_4$O—C(O)—, a protected P3 or the whole peptide or a peptide segment is coupled to an appropriate chloroformate that is either commercially available or for which the synthesis is well known in the art. For Boc-derivatives $(Boc)_2O$ is used.

For example:

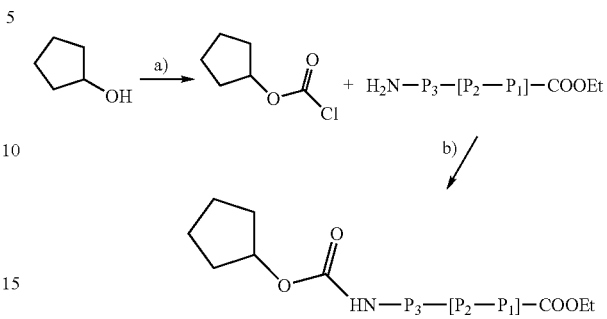

Cyclopentanol is treated with phosgene to furnish the corresponding chloroformate.

The chloroformate is treated with the desired $NH_2$-tripeptide in the presence of a base such as triethylamine to afford the cyclopentylcarbamate.

In preparing a compound where $R_4$—N($R_5$)—C(O)—, or $R_4$—NH—C(S)—, a protected P3 or the whole peptide or a peptide segment is treated with phosgene followed by amine as described in SynLett. February 1995; (2); 142–144 or is reacted with the commercially available isocyanate and a suitable base such as triethylamine.

In preparing a compound where $R_4$—N($R_5$)—S(O$_2$), a protected P3 or the whole peptide or a peptide segment is treated with either a freshly prepared or commercially available sulfamyl chloride followed by amine as described in patent Ger. Offen. (1998), 84 pp. DE 19802350 or WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $ASO_2NH_2$ as described herein.

Furthermore, if the P3 protecting group APG is removed and replaced with a B moiety by the methods described above, and the resulting α-carboxylic acid resulting from cleavage (resulting from cleavage by mild acid, mild base treatment or mild reductive means) is coupled with a $ASO_2NH_2$.

Compounds of the present invention can be prepared by many methods including those described in the examples, below, and as described in U.S. Pat. No. 6,323,180 and U.S. patent application Ser. No. 10/001,850 filed on Nov. 20, 2001. The teachings of U.S. Pat. No. 6,323,180 and U.S. patent application Ser. No. 10/001,850 are incorporated herein, in their entirety, by reference.

Scheme II further shows the general process wherein compounds of Formula I are constructed by the coupling of tripeptide carboxylic acid intermediate (1) with a P1' sulfonamide. (It should be noted that the groups $R_6$, $R_7$, $R_8$, $R_9$, $R_{10}$, $R_{11}$ as shown below represent substituents of the heterocyclic system.) Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or methylene chloride in the presence of a base such as DBU.

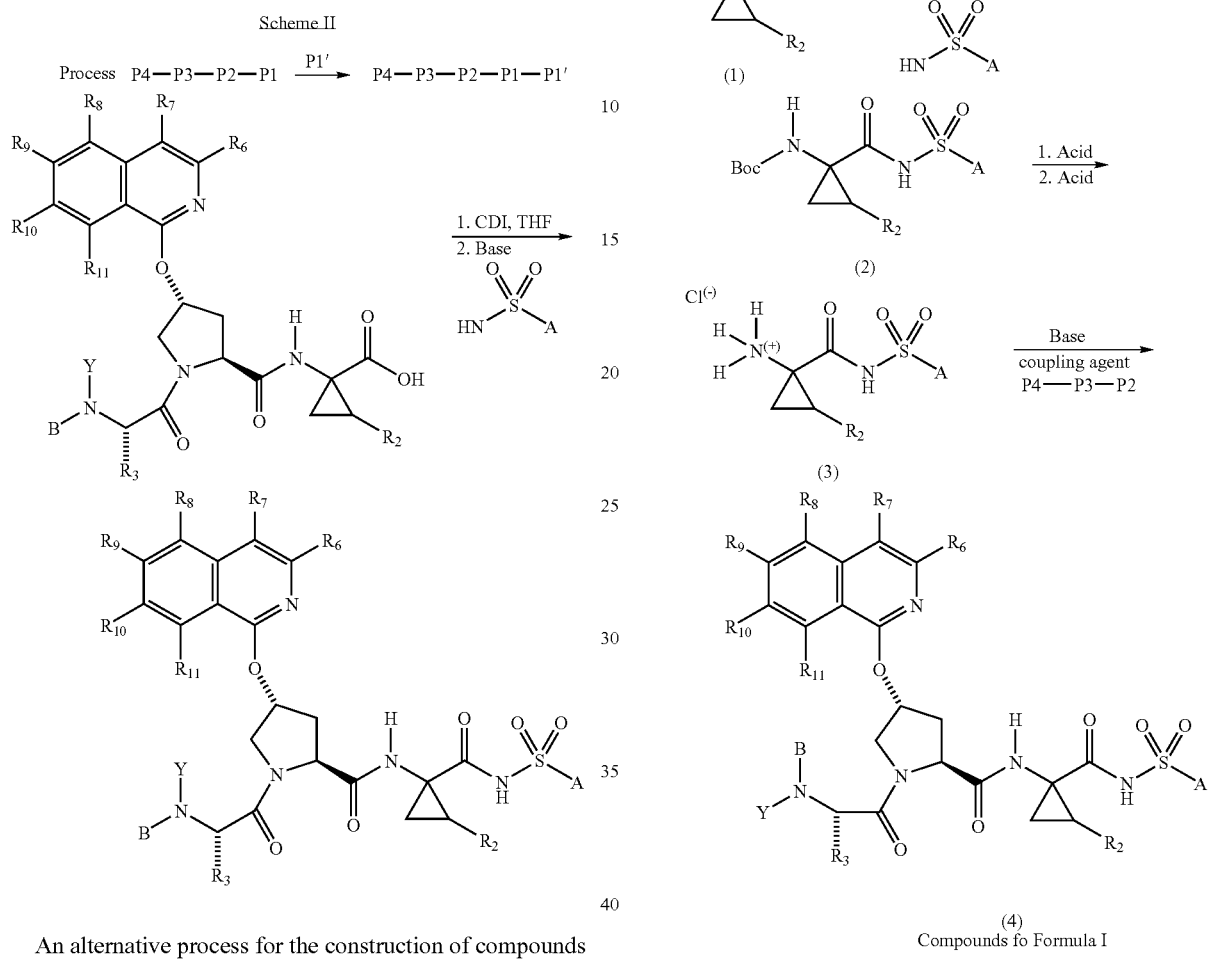

An alternative process for the construction of compounds of Formula I is shown in Scheme III. Therein the P1' sulfonamide element is coupled to the P1 element using the process employed in Scheme 1. The resulting P1–P1' moiety can then be deprotected at it's amino terminus. In this general example a Boc protecting group is employed but one skilled in the art would recognize that a number of suitable amino protecting groups could be employed in this process. Said Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme III. The coupling of said HCl amine salt (3) with the carboxyl terminus a P4–P3–P2 intermediate can be achieved using coupling reagents, such as HATU, in solvents such as dichloromethane to provide compounds of Formula I (4).

An alternative process for the construction of compounds of Formula I is shown in Scheme IV. Herein the hydrochloride salt of the P1–P1' terminal amine (1) is coupled to the free carboxyl group of the P2 element using coupling agents such as PyBOP, in the presence of a base such as diisopropyl amine, and in a solvent such as methylene chloride. The resulting P2–P1–P1' intermediate can be converted to compounds of Formula I in a two step process wherein the first step is deprotection of the P2 amine terminus using an acid such as TFA in a solvent such as methylene chloride. The resulting trifluoroacetic acid salt can be coupled with the carboxyl terminus of the P4–P3 element using standard coupling agents such as PyBop in the presence of base such as diisopropyl amine, and using solvents such methylene chloride to provide compounds of Formula I (4).

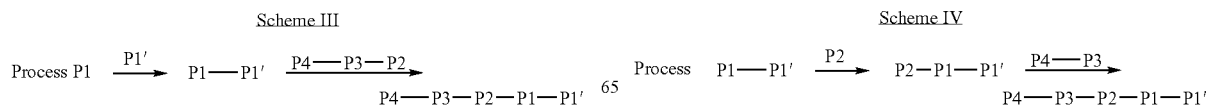

-continued

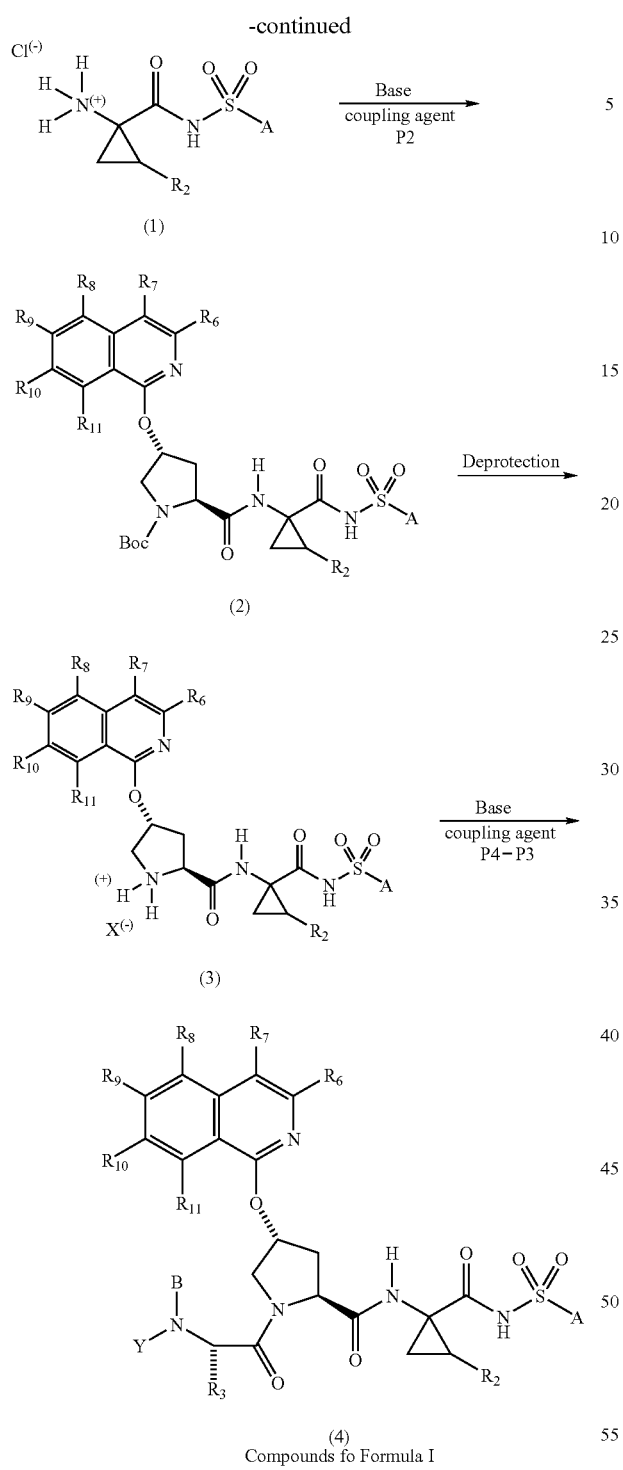

(1)

(2)

(3)

(4)
Compounds fo Formula I

The P4–P3–P2 intermediate utilized in the above schemes can be constructed as previously described with a further description of this process shown in general Scheme V. Therein the free carboxyl terminus of the P4–P3 intermediate (1), can be coupled to the amino terminus of the P2 element to provide the P4–P3–P2 dipeptide (2). The carboxyl terminus of the P4–P3–P2 intermediate can be deprotected by saponification of the ester group to provide P4–P3–P2 as the free carboxylic acid (3). Intermediates like (3) can be converted to compounds of Formula I using the methods described herein.

Scheme V

Process  P4—P3  $\xrightarrow{P2}$  P4—P3—P2

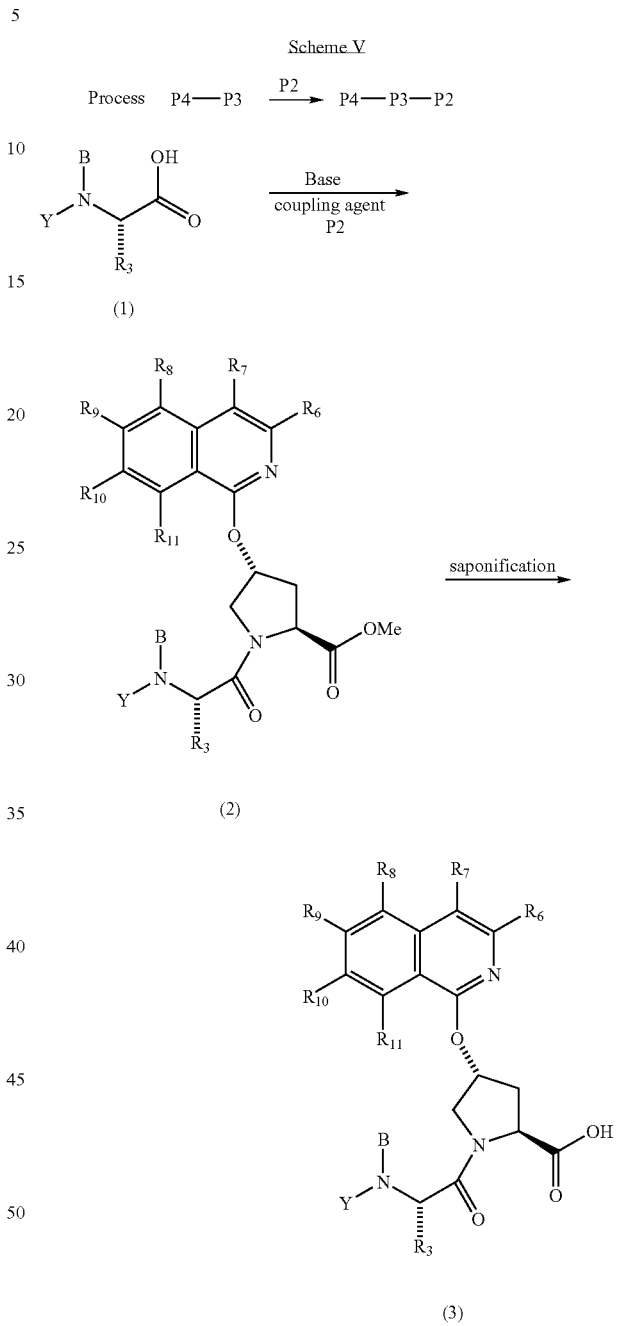

(1)

(2)

(3)

Compounds of Formula 1 can also be converted into other compounds of Formula I as described herein. An example of such a process is shown in Scheme VI wherein a compound of Formula I (1) which bears a Boc group at the P4 position is converted in a compound of Formula I (3) wherein said compound bears a urea group at the P4 position. The conversion of (1) to (3) can be carried out in a two step process the first of which is the conversion of (1) to amine (2) by treatment of (1) with an acid such as TFA in a solvent such as methylene chloride. The resulting amine TFA salt can be treated with an isocyanate in the presence of one equivalent of base to provide a compound of Formula I (3) wherein the P3 moiety is capped with a urea. As previously noted one skilled in the art will recognize that intermediate (2) can be used as starting materials for the preparation of compounds of Formula I wherein the P3 group is capped with an amide or a sulfonamide, or thiourea, or a sulfamide. The construction of said compounds of Formula I can be achieved using standard conditions for the formation of said P4 functionalities from amines.

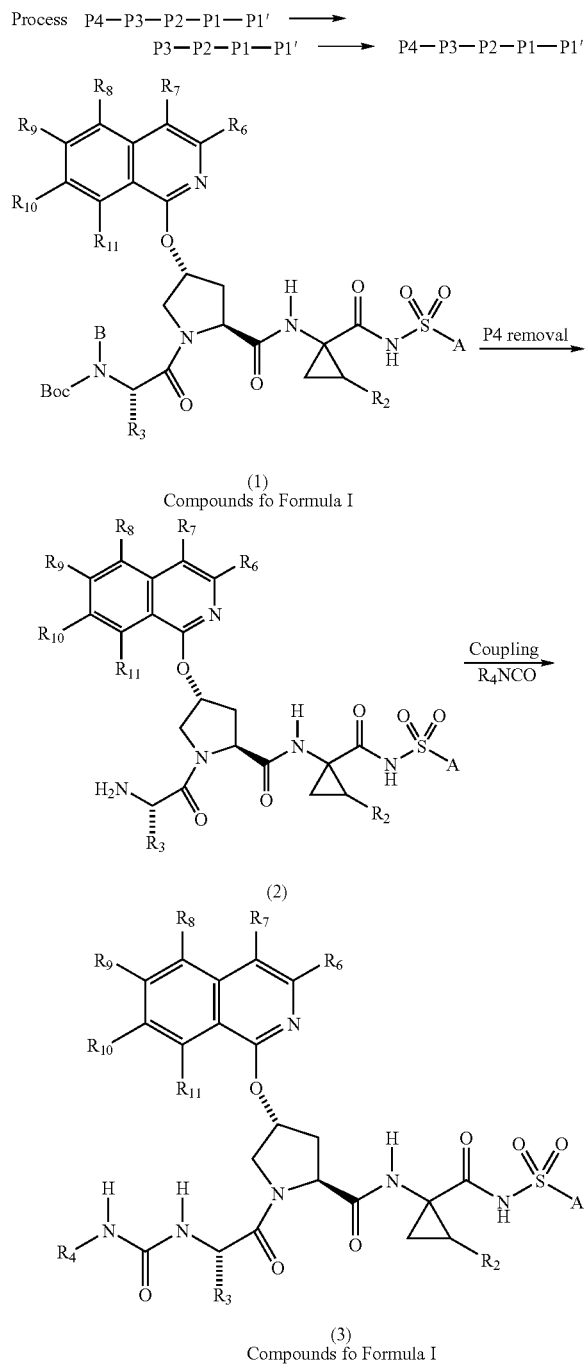

In the construction of compounds of Formula I, the P1' terminus is incorporated into the molecules using one of the general processes outlined above and described in more detail below. In some examples the P1' elements, that is the substituted cycloalkyl-sulfonamides are commercially available or can be prepared from the corresponding alkyl- or cycloalkyl-sulfonyl chloride by treating said sulfonyl chloride with ammonia. Alternatively, these sulfonamides can be synthesized using the general process outline in Scheme VII. Therein commercially available 3-chloro-propylsulfonyl chloride (1) is converted to a suitable protected sulfonamide as for example by treatment with tert-butyl amine. The sulfonamide obtained (2) is then converted to the corresponding substituted cycloalkylsulfonamide by treatment with a base such as butyl lithium in a solvent such as THF at low temperature followed by the addition of an electrophile. The resulting substituted cycloalkylsulfonamide can be deprotected by treatment with an acid to provide the desired unprotected substituted cycloalkylsulfonamide.

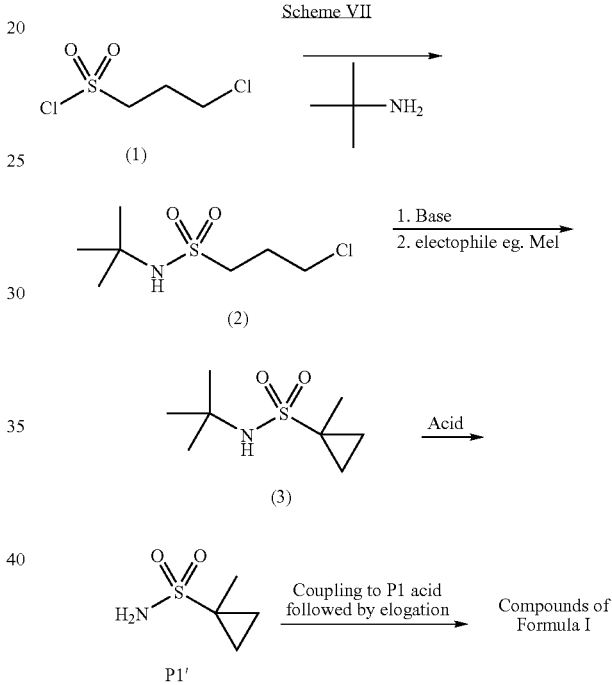

The P1 elements utilized in generating compounds of Formula I are in some cases commercially available, but are otherwise synthesized using the methods described herein and subsequently incorporated into compounds of Formula I using the methods described herein. The substituted P1 cyclopropylamino acids can be synthesized following the general process outline in Scheme VIII.

Treatment of commercially available or easily synthesized imine (1) with 1,4-dihalobutene (2) in presence of a base produces, provides the resulting imine (3). Acid hydrolysis of 3 then provides 4, which has an allyl substituent syn to the carboxyl group as a major product. The amine moiety of 4 can protected using a Boc group to provide the fully protected amino acid 5. This intermediate is a racemate which can be resolved by an enzymatic process wherein the ester moiety of 5 is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, the more preferred stereoisomer for integration into compounds of Formula I is 5a which houses the (1R,2S) stereochemistry. In the presence of the enzyme, this enantiomer does not undergo ester cleavage and thereby this enantiomer 5a is recovered from the reaction mixture. However, the less preferred enantiomer, 5b with houses the (1S,2R) stereochemistry undergoes ester cleavage, i.e., hydrolysis, to provide the free acid 6. Upon completion of this reaction, the ester 5a can be separated from the acid product 6 by routine methods such as, for example, aqueous extraction methods or chromatography.

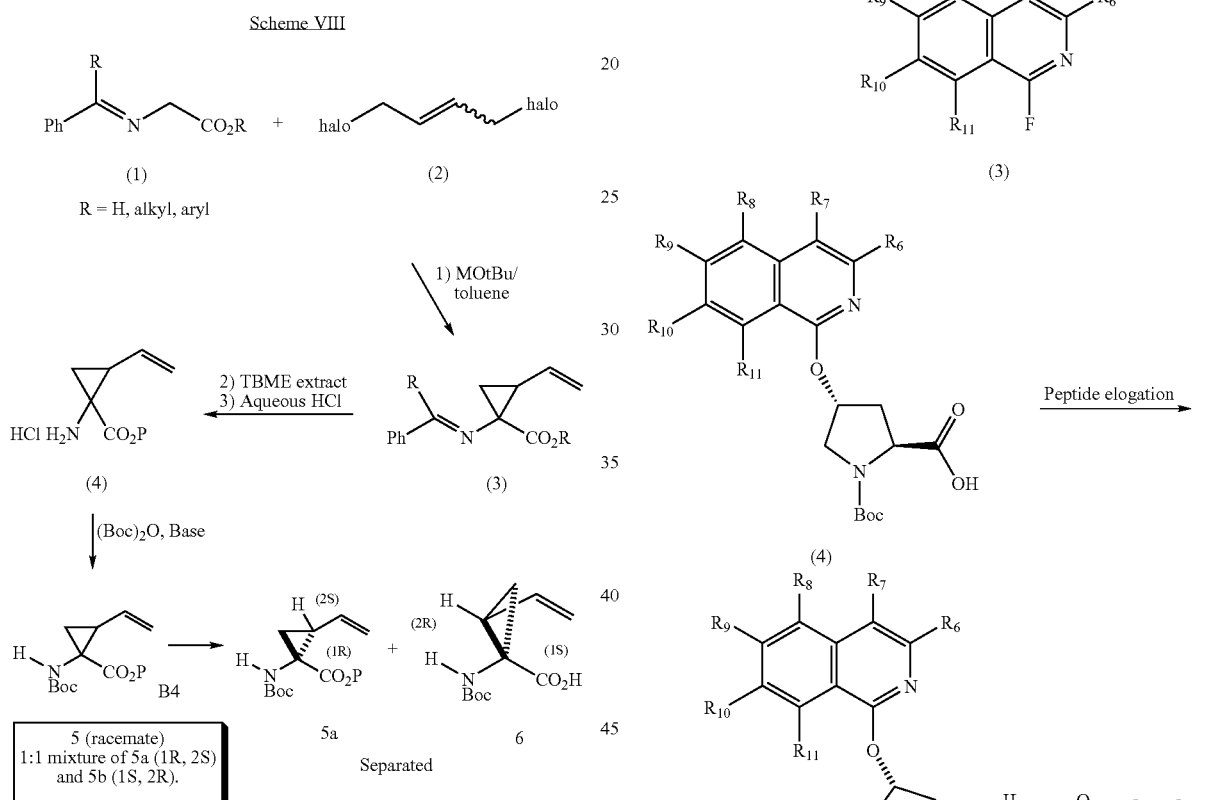

Procedures for making P2 intermediates and compounds of Formula I are shown in the Schemes below. It should be noted that in many cases reactions are depicted for only one position of an intermediate. However, it is to be understood that such reactions could be used to impart modifications to other positions within this intermediate. Moreover, said intermediates, reaction conditions and methods given in the specific examples are broadly applicable to compounds with other substitution patterns. The general Schemes outlined below are followed with examples herein. Both general and specific examples are non-limiting, as for example the isoquinoline nucleus is shown as part of the general scheme, Scheme IX, however, this pathway represents a viable process for the construction of alternate heterocycle substituents as replacements for the isoquinoline element, such as quinolines, or pyridines.

Scheme IX shows the coupling of an N-protected C4-hydroxyproline moiety with a heterocycle to form intermediate (4) and the subsequent modification of said intermediate (4) to a compound of Formula I by the process of peptide elongation as described herein. It should be noted that in the first step, that is the coupling of the C4-hydroxy proline group with the heteroaryl element, a base is employed. One skilled in the art would recognized that this coupling can be done using bases such as potassium tert-butoxide, or sodium hydride, in solvent such as DMF or DMSO or THF. This coupling to the isoquinoline ring system occurs at the C1 position (numbering for isoquinoline ring system shown in intermediate 2 of Scheme IX) and is directed by the chloro group which is displaced in this process. It should be noted that the alternative leaving groups can be utilized at this position such as a fluoro as shown in the Scheme. Said fluoro intermediates (3) are available from the corresponding chloro compound using literature procedures described herein. It should also be noted that the position of the leaving group (chloro or fluoro) in a given ring system can vary as shown in Scheme X, wherein the leaving group (fluoro in this example) is in the C6 position of the isoquinoline ring system of intermediate (2).

cycle described herein. In Scheme X intermediate (2) can be coupled to a C4 hydroxy proline derivative to provide the P2 element (3). This C6-substituted isoquinoline derivative can be converted to compounds of Formula I using the methods described herein.

An alternative to the method described above for the coupling of the C4-hydroxyproline to aromatics and heteroaromatics, is provided in the Mitsunobu reaction as depicted in

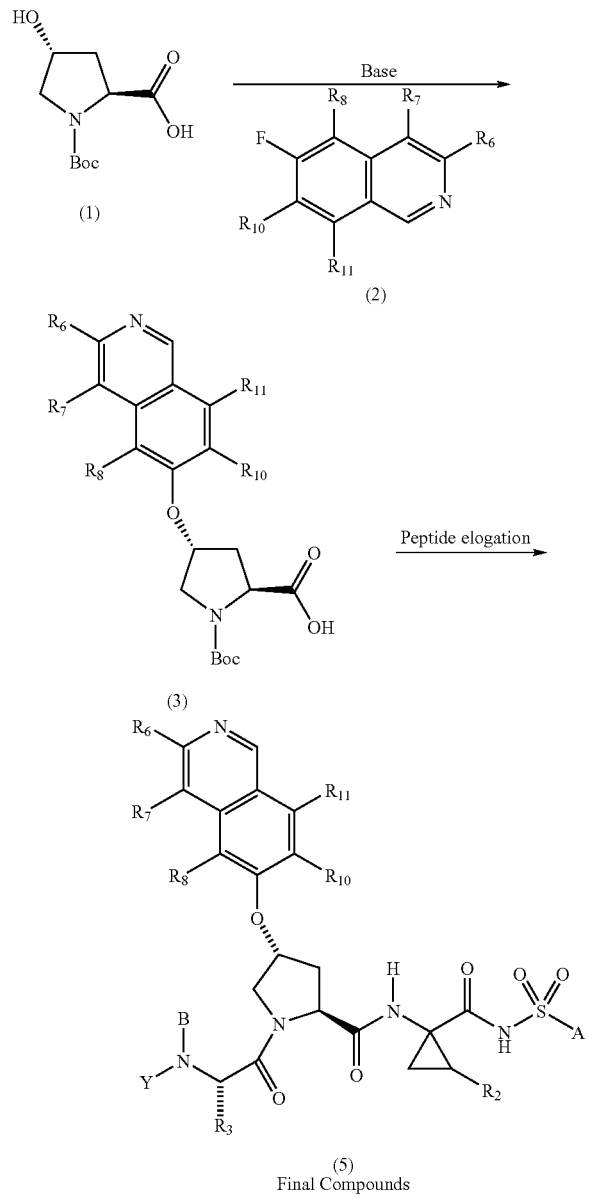

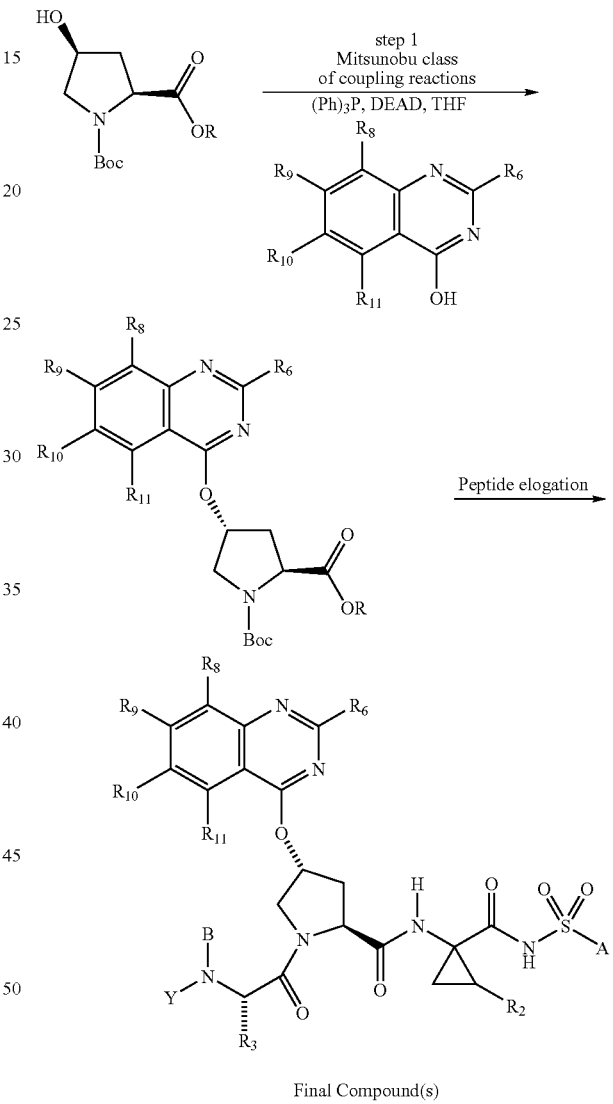

step 1 of Scheme XI. In this general reaction Scheme a $C_4$-hydroxy proline derivative is coupled to a quinazoline ring system. This reaction makes use of reagents such as triphenylphosphine and DEAD (diethylazodicarboxylate) in aprotic solvents such as THF or dioxane and can be used for the formation of aryl and heteroaryl ethers. Note that in the course of this coupling reaction the stereochemistry of the C4 chiral center in the C4-hydroxyproline derivative is inverted and thereby it is necessary to use the C4-hydroxyproline derivative housing the (S) stereochemistry at the C4 position as starting material. (as shown in Scheme XI). It It should be further noted that the position of the ring heteroatom(s) in intermediates like (2) of Scheme IX and Scheme X is also variable, as defined by the term heteroshould be noted that numerous modifications and improvements of the Mitsunobu reaction have been described in the literature, the teachings of which are incorporated herein.

In a subset of examples herein, isoquinolines are incorporated into the final compounds and specifically into the P2 region of said compounds. One skilled in the art would recognize that a number of general methods are available for the synthesis of isoquinolines. Moreoever, said isoquinolines generated by these methods can be readily incorporated into final compounds of Formula I using the processes described herein. One general methodology for the synthesis of isoquinolines is shown in Scheme XII, wherein cinnamic acid derivatives, shown in general form as structure (2) are converted to 1-chloroisoquinolines in a four step process. Said chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the Scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is coverted to the corresponding isoquinolone (4) as shown in the Scheme. In the event the acylazide is heated to a temperature of approximately 190 degress celcius in a high boiling solvent such a diphenylmethane. This reaction is general and provides moderate to good yields of substituted isoquinolone from the corresponding cinnamic acid derivatives. It should noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) of Scheme XII can be converted to the corresponding 1-chloroisoquinoline by treatment with phosphorous oxychloride. This reaction is general and can be applied to any of the isoquinolones, quinolones or additional heterocycles as shown herein to covert a hydroxy substituent to the corresponding chloro compound when said hydroxy is in conjugation with a nitrogen atom in said -heterocylic ring systems.

An alternative method for the synthesis of the isoquinoline ring system is the Pomeranz-Fritsh procedure. This general method is outlined in Scheme XIII. The process begins with the conversion of a benzaldehyde derivative (1) to a functionalized imine (2). Said imine is then converted to the isoquinoline ring system by treatment with acid at elevated

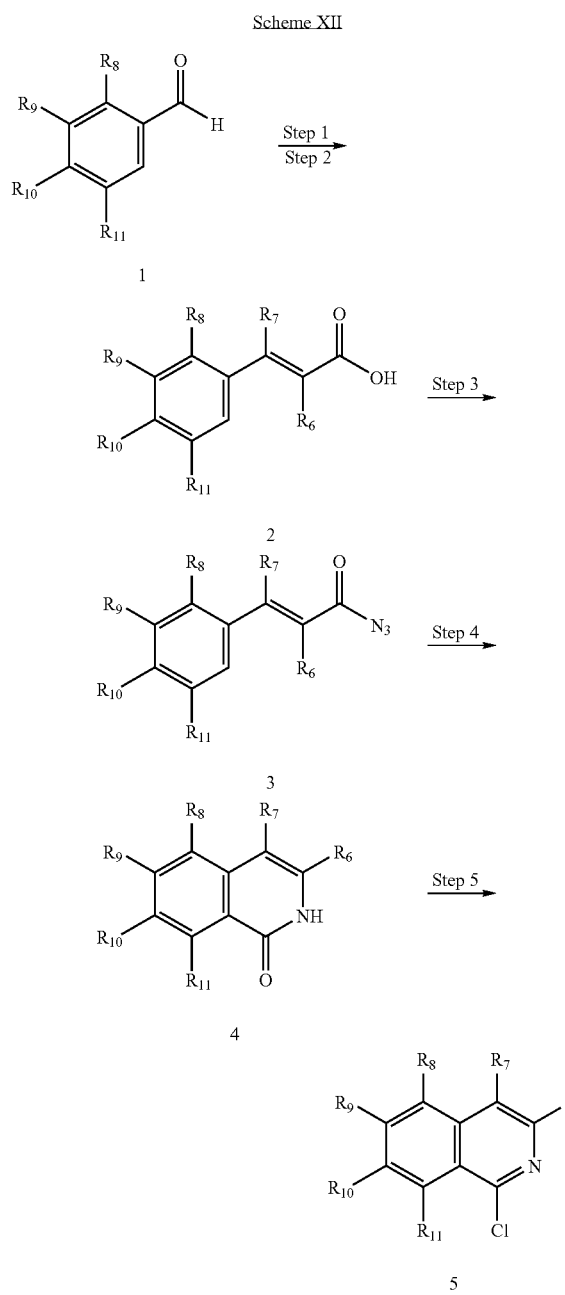

Reference: N. Briet at al, *Tetrahedron*, 2002, 5761

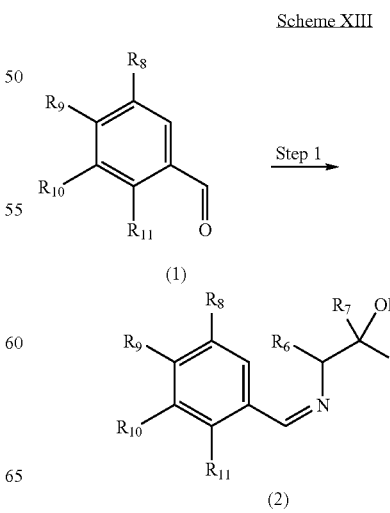

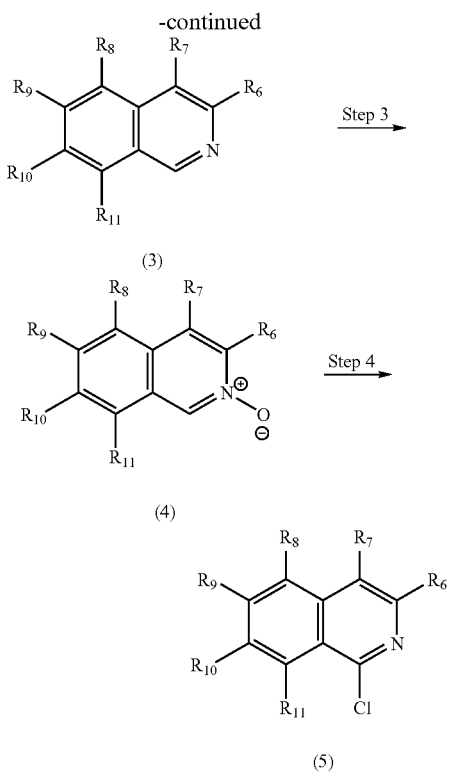

Pomeranz-Fritsch synthesis
K. Hirao, R. Tsuchiya, Y. Yano, H. Tsue, Heterocycles 42(1) 1996, 415–422 temperature. This isoquinoline synthesis of Scheme XIII is general, and it should be noted that this process is particularly useful in procuring isoquinoline intermediates that are substituted at the C8 position (note: in intermediate (3) of Scheme XIII the C8 position of the isoquinoline ring is substituted with substutuent $R_{11}$). The intermediate isoquinolines (3) can be converted to the corresponding 1-chloroquinolines (5) in a two step process as shown. The first step in this sequence is the formation of the isoquinoline N-oxide (4) by treatment of isoquinoline (3) with meta-chloroperbenzoic acid in an aprotic solvent such as dichloromethane. Intermediate (4) can be converted to the corresponding 1-chloroquinoline by treatment with phosphorous oxychloroide in refluxing chloroform. Note this two step process is general and can be employed to procure chloroisoquinolines and chloroquinolines from the corresponding isoquinolines and quinolines respectively. Another method for the synthesis of the isoquinoline ring system is shown in Scheme XIV. In this process an ortho-alkylbenzamide derivative (1) is treated with a strong Scheme XIV

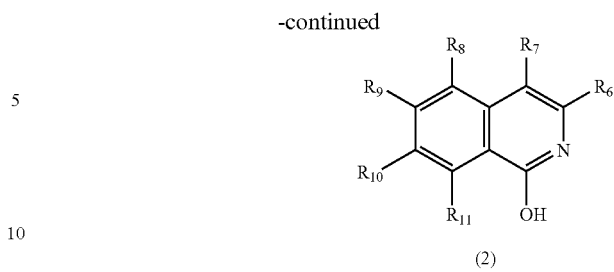

base such as tert-butyl lithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of Scheme XIV can be converted to the corresponding 1-chloroquinoline by the methods described herein.

An additional method for the synthesis of isoquinolines is shown in Scheme XV. The deprotonation of intermediate (1) using tert-butyl lithium is described above. In the present method however, said intermediate anion is trapped by an ester, resulting in the formation of intermediate (2) as shown below. In a subsequent reaction ketone (2) is condensed with ammoniumn acetate at elevated temperature providing for the formation of quinolone (3). This reaction is general and can be applied for the construction of substituted isoquinolones which can then be converted to the corresponding 1-chloroisoquinolines as described herein.

Scheme XV

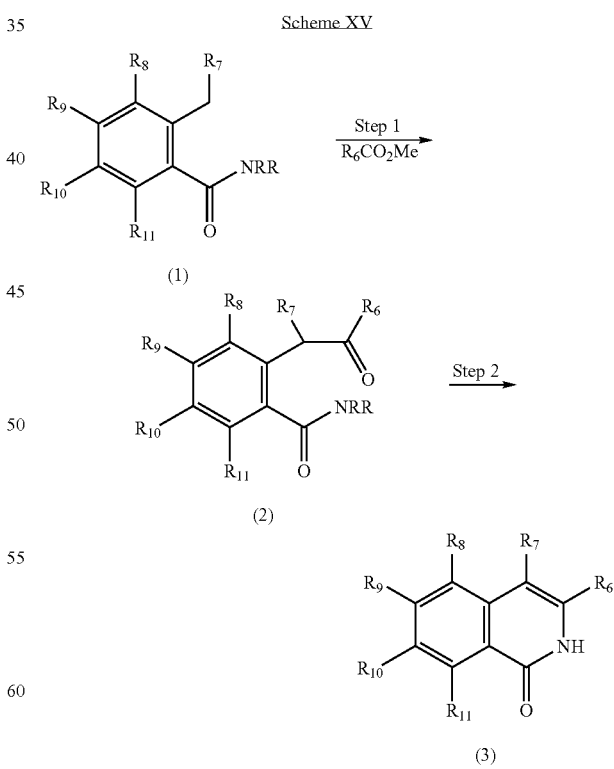

Yet an additional method for the construction of isoquinolines is found in Scheme XVI. In the first step of this process an ortho-alkylarylimine derivatives such as (1) is subjected to deprotonation conditions (sec-butyl lithium, THF) and the resulting anion is quenched by

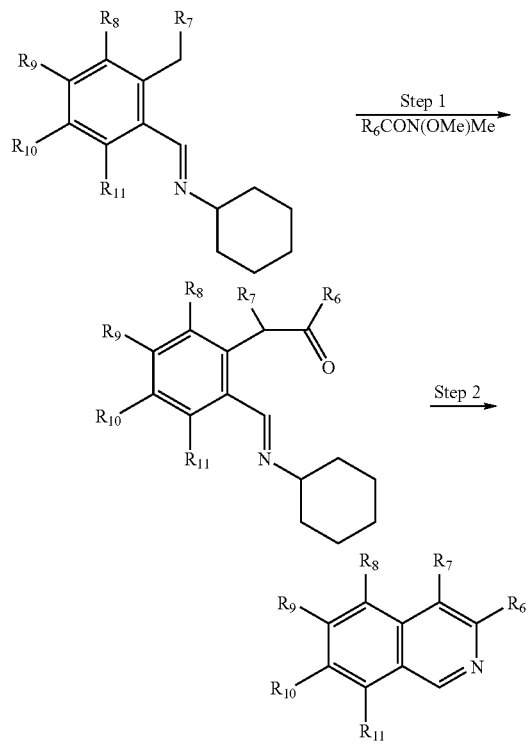

L. Flippin, J. Muchowski, JOC, 1993, 2631–2632 the addition of an activated carboxylic acid derivative such as a Weinreb amide. The resulting keto imine (2) can be converted to the corresponding isoquinoline by condensation with ammonium acetate at elevated temperatures. This method is general and can be used for the synthesis of substituted isoquinolines. Said isoquinolines can be converted to the corresponding 1-chloroquinoline by the methods described herein.

The heterocycles described herein, and which are incorporated into the compounds of Formula I can be further functionalized. It is obvious to one skilled in the art that additional functionalization of said heterocycles can be done either before or after incorporation of these functionalities into compounds of Formula I. The following Schemes illustrate this point. For example Scheme XVII shows the conversion of a 1-chloro-

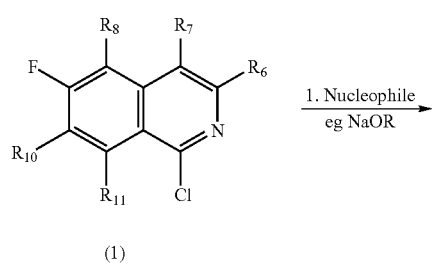

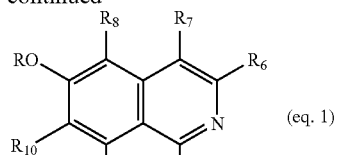

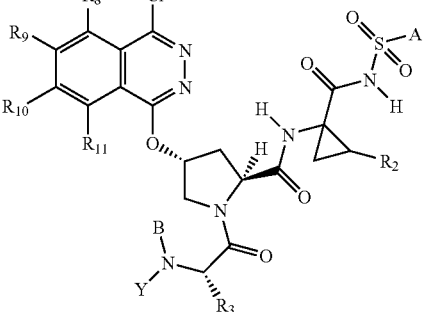

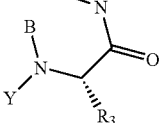

6-fluoro-isoquinoline to the corresponding 1-chloro-6-alkoxy-isoquinoline species, by treatment of (1) of (eq. 1) with a sodium or potassium alkoxide species in the alcohol solvent from which the alkoxide is derived at room temperature. In some cases it may be necessary to heat the reaction to drive it to completion. Said chloroquinoline can be incorporated into a compound of Formula I using the art described herein. Modifications of a P2 heterocyclic element can also be done after it's incorporation into compounds of Formula I as shown in (eq. 2) of Scheme VXII. Specifically compounds such as (1) in (eq. 2) which contain a leaving group in the pthalazine nucleus can be displaced by a nucleophile such as an alkoxide in solvents such as the corresponding alcohol from which the alkoxide is derived. These reaction scan be conducted at room temperature but in some cases it may be necessary to heat the reaction to drive it to completion.

Scheme XVIII provides a general example for the modification of heterocycles as defined herein by employing palladium mediated coupling reactions. Said couplings can be employed to functionalize a heterocycle at each position of the ring system providing said ring is suitably activated or functionalized, as for example with a chloride as shown in the Scheme. This sequence begins with 1-chloroisoquinoline (1) which upon treatment with metachloroperbenzoic acid can be converted to the corresponding N-oxide (2). Said intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the Scheme. Intermediate (5) can undergo a Suzuki coupling with an aryl boronic acid, in the presence of a palladium reagent and base, and in a solvent such as THF or toluene or DMF to provide the $C_3$-arylisoquinoline intermediate (6).

Heteroarylboronic acids can also be employed in this Pd mediated coupling process to provide C3-heteroarylisoquinolines. Intermediate (6) can be converted into final compounds of Formula I by the methods described herein.

Scheme XVIII

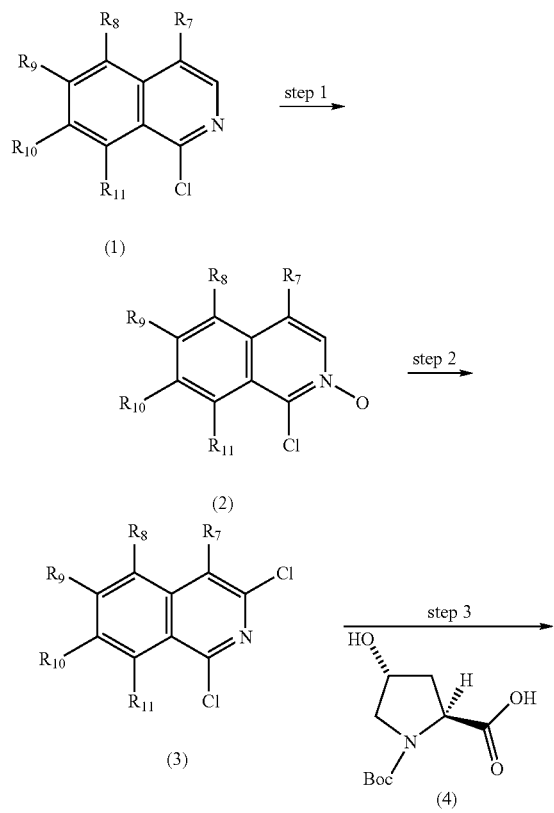

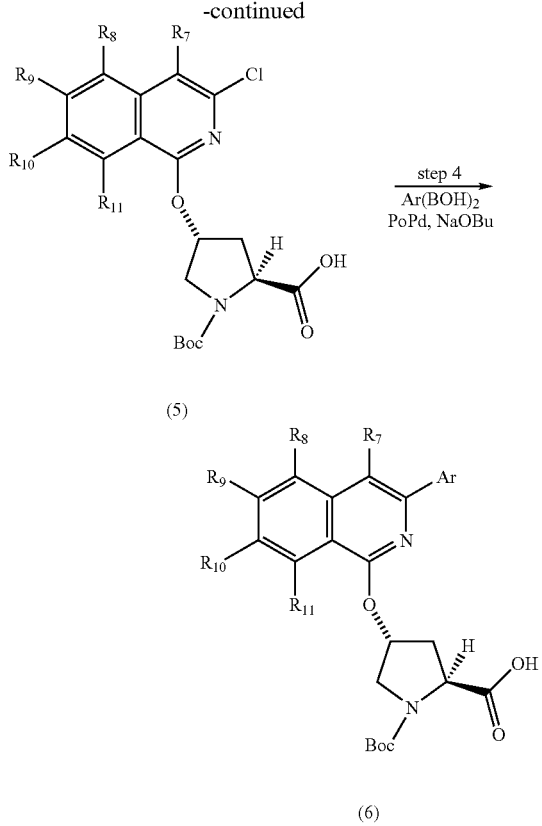

Palladium mediated couplings of heteroaryl systems with aryl or heteroaryl elements can also be employed at a later synthetic stage in the construction of compounds of Formula I as shown in Scheme IXX. Therein tripeptide acylsulfonamide intermediate (1) is coupled to a 1-chloro-3-bromoisoquinoline (2) using the previously described process of alkoxide displacement of an heteroarylhalo moiety to provide intermediate (3). The coupling of (1) and (2) is most efficient in the presence of a catalyst such as lanthanum chloride as described herein. The isoquinoline ring system of intermediate (3) can be further functionalized by employing either Suzuki couplings (Process 1: subjecting (3) to heteroaryl or aryl boronic acids in the presence of a palladium catalyst such as palladium tetra(triphenylphosphine) and a base such as cesium carbonate in solvents such as DMF) or Stille couplings (Process 2: subjecting (3) to heteraryl or aryl tin dervatives in the presence of palladium catalyst such as palladium tetra(triphenylphosphine in solvents such as toluene).

Scheme IXX

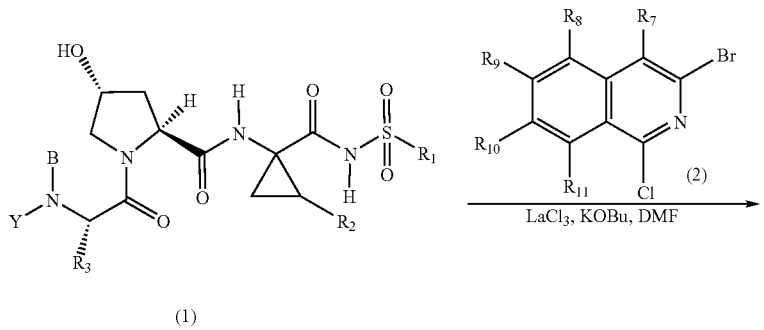

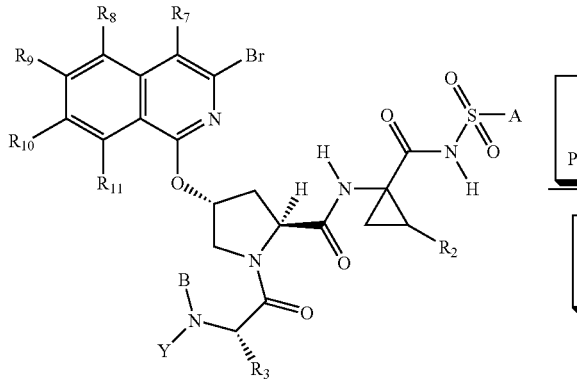

(3)

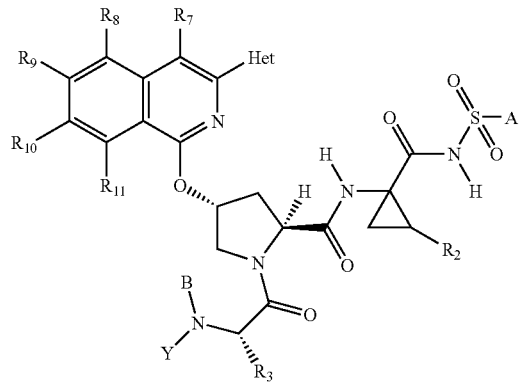

(4)

Palladium reactions can also be employed to couple C4-amino proline elements with functionalized heterocycles. Scheme XX shows intermediate (1) coupling with a functionalized isoquinoline in the presence of a palladium catalyst and a base in a solvent such as toluene. Intermediates like (3) can be converted to compounds of Formula I using the methods described herein.

Scheme XX

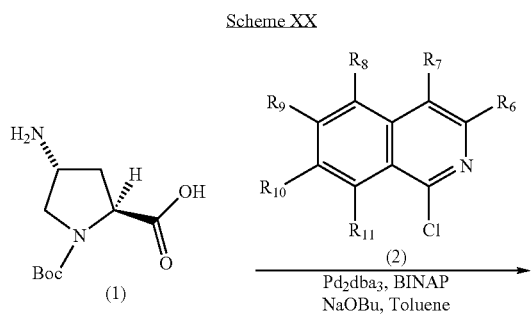

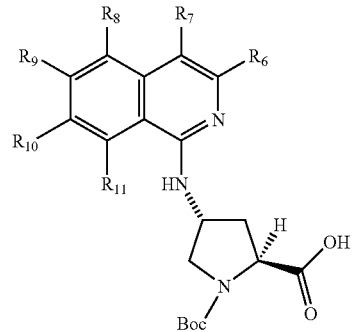

(3)

The construction of functionalized isoquinoline ring systems is also possible employing [4+2] cycloaddition reactions. For example (Scheme XXI) the use of vinyl isocyantes (1) in cycloaddition reactions with benzyne precusors (2) provides functionalized isoquinolones (3). Said isoquinolines can be incorporated into compounds of Formula I using the methods described herein.

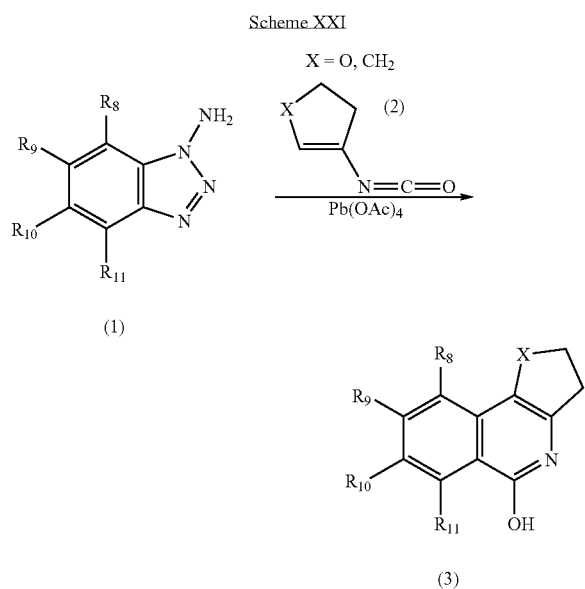

Compounds of the invention can also be prepared by utilizing methods known to thise skilled in the art, such as, for example, the methods described in patent application WO 03/099274, published Dec. 3, 2003, and WO 2004/043339, published May 27, 2004.

The present invention also provides compositions comprising a compound of the present invention, or a pharmaceutically acceptable enantiomer, diastereomer, salt, solvate or prodrug thereof, and a pharmaceutically acceptable carrier. Pharmaceutical compositions of the present invention comprise a therapeutically effective amount of a compound of the invention, or a pharmaceutically acceptable enantiomer, diastereomer, salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

Thus, in one aspect of the invention, there is provided a composition comprising the compound of formula I and a pharmaceutically acceptable carrier. Preferably, the composition further comprises a compound having anti-HCV activity. As used herein, the term "anti-HCV activity" means the compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. Often, the other compound having anti-HCV activity is effective to inhibit the function of target in the HCV life cycle other than the HCV NS3 protease protein.

In one preferred aspect, the compound having anti-HCV activity is an interferon. Preferably, the interferon is selected from the group consisting of interferon alpha 2B, pegylated interferon alpha, consensus interferon, interferon alpha 2A, lymphoblastiod interferon tau.

In another aspect of the invention, the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In one preferred aspect of the invention, the composition comprises a compound of the invention, an interferon and ribavirin.

In another preferred aspect of the invention, the compound having anti-HCV activity is a small molecule compound. As used herein, the term "small molecule compound" means a compound having a molecular weight of less than 1,500 daltons, preferably less than 1000 daltons. Preferably, the small molecule compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, inosine monophophate dehydrogenase ("IMPDH") and a nucleoside analog for the treatment of an HCV infection.

Certain illustrative HCV inhibitor compounds which can be administered with the compounds of the present invention include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this invention. The compounds of the invention can be administered with other anti-HCV activity compounds in combination therapy, either jointly or separately, or by combining the compounds into a composition.

TABLE 1

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |

TABLE 1-continued

| Brand Name | Type of Inhibitor or Target | Source Company |
|---|---|---|
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/ LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Other suitable carriers for the above noted compositions can be found in standard pharmaceutical texts, e.g. in "Remington's Pharmaceutical Sciences", 19th ed., Mack Publishing Company, Easton, Pa., 1995.

The pharmaceutical compositions can be prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable enantiomers, diastereomers, salts, solvates or prodrugs are formulated together with a pharmaceutically acceptable carrier, the resulting composition may be administered in vivo to mammals, such as man, to inhibit HCV NS3 protease or to treat or prevent HCV virus infection.

Accordingly, another aspect of this invention provides methods of inhibiting HCV NS3 protease activity in patients by administering a compound of the present invention or a pharmaceutically acceptable enantiomer, diastereomer, salt or solvate thereof.

In one aspect of the invention, there is provided a method of treating an HCV infection in a patient, comprising administering to the patient a therapeutically effective amount of the compound of the invention, or a pharmaceutically acceptable enantiomer, diastereomer, solvate, prodrug or salt thereof.

Preferably, the method of administering the compound is effective to inhibit the function of the HCV NS3 protease protein. In a preferred aspect, the method further comprises administering another compound having anti-HCV activity (as described above) prior to, after or concurrently with a compound of the invention.

The compounds of the invention may also be used as laboratory reagents. Compounds may be instrumental in providing research tools for designing of viral replication assays, validation of animal assay systems and structural biology studies to further enhance knowledge of the HCV disease mechanisms. Further, the compounds of the present invention are useful in establishing or determining the binding site of other antiviral compounds, for example, by competitive inhibition.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the invention can be used for the manufacture of a medicament for treating HCV infection in a patient.

EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts ($\delta$) are reported in parts per million. Flash chromatography was carried out on silica gel ($SiO_2$) according to Still's flash chromatography technique (W. C. Still et al., J. Org. Chem., (1978), 43, 2923).

All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+).

Unless otherwise noted, in the following examples each compound was analyzed by LC/MS, using one of seven methodologies, having the following conditions.

Columns:
  (Method A)—YMC ODS S7 C18 3.0×50 mm
  (Method B)—YMC ODS-A S7 C18 3.0×50 mm
  (Method C)—YMC S7 C18 3.0×50 mm
  (Method D)—YMC Xterra ODS S7 3.0×50 mm
  (Method E)—YMC Xterra ODS S7 3.0×50 mm
  (Method F)—YMC ODS-A S7 C18 3.0×50 mm
  (Method G)—YMC C18 S5 4.6×50 mm]
Gradient: 100% Solvent A/0% Solvent B to 0% Solvent A/100% Solvent B
Gradient time: 2 min. (A, B, D, F, G); 8 min. (C, E)
Hold time: 1 min. (A, B, D, F, G); 2 min. (C, E)
Flow rate: 5 mL/min
Detector Wavelength: 220 nm
Solvent A: 10% MeOH/90% $H_2O$/0.1% TFA
Solvent B: 10% $H_2O$/90% MeOH/0.1% TFA.

The abbreviations used in the present application, including particularly in the illustrative examples which follow, are well-known to those skilled in the art. Some of the abbreviations used are as follows:

rt room temperature
Boc tert-butyloxycarbonyl
DMSO dimethylsulfoxide
EtOAc ethyl acetate
t-BuOK potassium t-butoxide
$Et_2O$ diethyl ether
TBME tert-butylmethyl ether
THF tetrahydrofuran
CDI carbonyldiimidazole
DBU 1,8-diazabicyclo[5.4.0]undec-7-ene
TFA trifluoroacetic acid
NMM N-methylmorpholine
HATU O-7-azabenzotriazol-1-yl
HBTU O-{1H-benzotriazol-1-yl)-N,N,N',N'-tetramethyluronium hexafluorophosphate
HOBT N-hydroxybenzotriazole
PyBrop bromo-bis-pyrrolidine-phosphonium hexafluorophosphate
DMF dimethylformamide
MeOH methanol
EDTA ethylenediaminetetraacetic acid
HRMS high resolution mass spectrometry
DMAP 4-dimethylaminopyridine
DIPEA diisopropylethylamine
DCM dichloromethane
DCE dichloroethane The compounds and chemical intermediates of the present invention, described in the following examples, were prepared according to the following methods. It should be noted that the following exemplification section is presented in sections. Example numbers and compound numbers are not contiguous throughout the entire Examples portion of the application and hence, each section indicates a "break" in the numbering. The numbering within each section is generally contiguous.

Section A:

Preparation of Intermediates:

Preparation of P1 Intermediates:

The P1 intermediates described in this section can be used to prepare compounds of Formula I by the methods described herein.

I P1 Elements:

1. Preparation of racemic (1R,2S)/(1S,2R)-1-amino-2-vinylcyclopropane carboxylic acid ethyl ester Method A

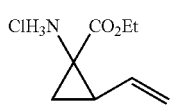

Step 1

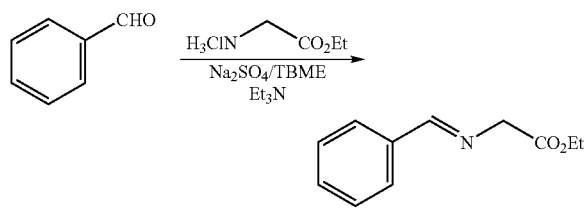

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous $NaHCO_3$ (1 L) and brine (1 L). The solution was dried over $MgSO_4$, concentrated in vacuo to afford 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

Step 2

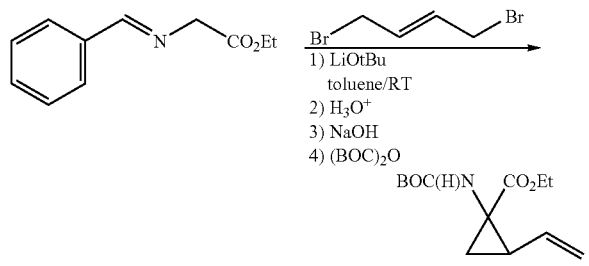

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried ($MgSO_4$) and concentrated to a volume of 1 L. To this solution of free amine, was added $BOC_2O$ or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over $MgSO_4$ and concentrated in vacuo to afford 80 g of crude material. This residue was purified by flash chromatography (2.5 Kg of $SiO_2$, eluted with 1% to 2% $MeOH/CH_2Cl_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR ($CDCl_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1).

Step 3 Preparation of Racemic (1R,2S)/(1S,2R) 1-amino-2-vinylcyclopropane carboxylic acid ethyl ester hydrochloride

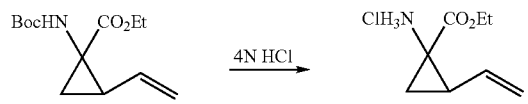

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-$d_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2, 1H), 5.69–5.81 (m, 1H).

Alternate route for the preparation of Racemic N-Boc-1-amino-2-vinylcyclopropane carboxylic acid ethyl ester hydrochloride

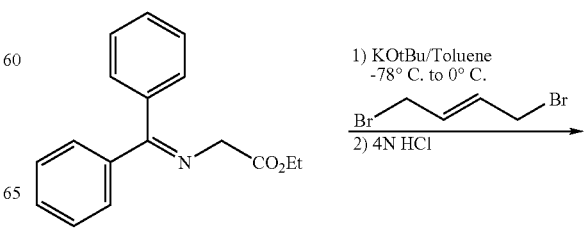

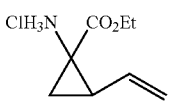

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in $Et_2O$ (530 mL), 1N aq. HCl solution (106 mL, 106 mmol) added and the resulting biphasic mixture stirred for 3.5 h at rt. The layers were separated and the aqueous layer was washed with $Et_2O$ (2×) and basified with a saturated aq. $NaHCO_3$ solution. The desired amine was extracted with $Et_2O$ (3×) and the combined organic extract was washed with brine, dried ($MgSO_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Resolution of N-Boc-(1R,2S)/(1S,2R)-1-amino-2-vinylcyclopropane carboxylic acid ethyl ester America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% $NaHCO_3$ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee").

The aqueous layer from the extraction process was then acidified to pH 2 with 50% $H_2SO_4$ and extracted with MTBE (2×2 L). The MTBE extract was washed with water (3×100 mL) and evaporated to give the acid as light yellow solid (42.74 g; purity: 99% @ 210 nm, containing no ester).

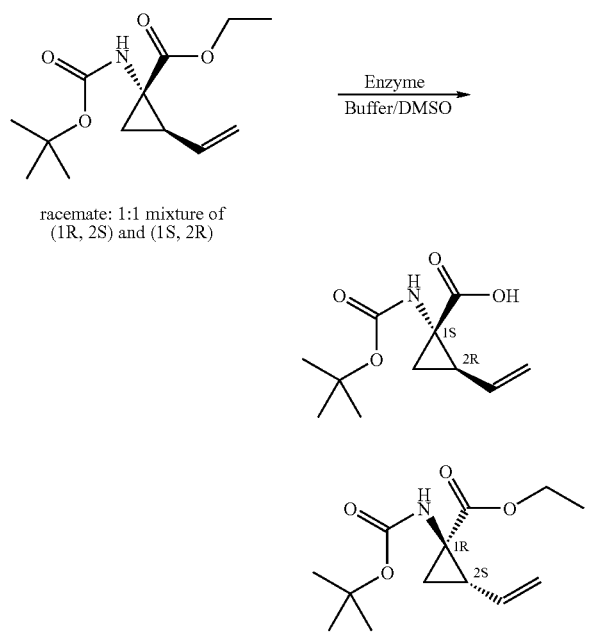

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Acalase 2.4 L (about 425 mL) (Novozymes North

| | ester | | acid | |
|---|---|---|---|---|
| High Resolution-Mass Spec | (+) ESI, C13H22NO4, [M + H]+, cal. 256.1549, found 256.1542 | | (−) ESI, C11H16NO4, [M − H]−, cal. 226.1079, found 226.1089 | |

NMR observed chemical shift
Solvent: $CDCl_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |

-continued

| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B

To 0.5 mL 100 mM Heps.Na buffer (pH 8.5) in a well of a 24 well plate (capacity: 10 ml/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("μl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Resolution C

To 0.5 ml 100 mM Heps.Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 μl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Samples analysis was carried out in the following manner:
1) Sample preparation: About 0.5 ml of the reaction mixture was mixed well with 10 volume of EtOH. After centrifugation, 10 μl of the supernatant was injected onto HPLC column.
2) Conversion determination:
Column: YMC ODS A, 4.6×50 mm, S-5 μm
Solvent: A, 1 mM HCl in water; B, MeCN
Gradient: 30% B for 1 min; 30% to 45% B over 0.5 min; 45% B for 1.5 min; 45% to 30% B over 0.5 min.
Flow rate: 2 ml/min
UV Detection: 210 nm
Retention time: acid, 1.2 min; ester, 2.8 min.
3) Enantio-excess determination for the ester:
Column: CHIRACEL OD-RH, 4.6×150 mm, S-5 μm
Mobile phase: MeCN/50 mM HClO$_4$ in water (67/33)
Flow rate: 0.75 ml/min.
UV Detection: 210 nm.

Retention time:
(1S,2R) isomer as acid: 5.2 min;
Rcaemate: 18.5 min and 20.0 min;
(1R,2S) isomer as ester: 18.5 min.

2. Preparation of N-Boc-(1R,2S)-1-amino-2-cyclopropylcyclopropane carboxylic acid ethyl ester

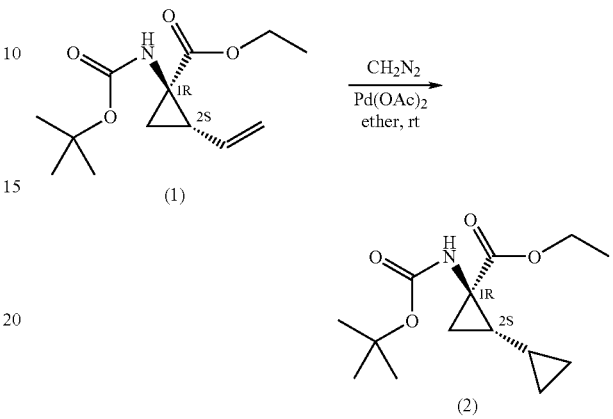

A solution of N-Boc-(1R,2S)-1-amino-2-vinylcyclopropane carboxylic acid (255 mg, 1.0 mmol) in ether (10 mL) was treated with palladium acetate (5 mg, 0.022 mmol). The orange/red solution was placed under an atmosphere of N$_2$. An excess of diazomethane in ether was added dropwise over the course of 1 h. The resulting solution was stirred at rt for 18 h. The excess diazomethane was removed using a stream of nitrogen. The resulting solution was concentrated by rotary evaporation to give the crude product. Flash chromatography (10% EtOAc/hexane) provided 210 mg (78%) of N-Boc-(1R,2S)-1-amino-2-cyclopropylcyclopropane carboxylic acid ethyl ester as a colorless oil. LC-MS (retention time: 2.13, similar to method A except: gradient time 3 min, Xterra MS C18 S7 3.0×50 mm column), MS m/e 270 (M$^+$+1).

3. 1-tert-butoxycarbonylamino-cyclopropane-carboxylic acid is commercially available

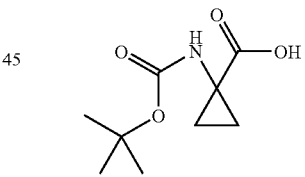

4. Preparation of 1-aminocyclobutanecarboxylic acid methyl ester.hydrochloride

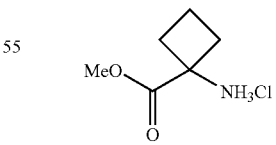

1-aminocyclobutanecarboxylic acid (100 mg, 0.869 mmol)(Tocris) was dissolved in 10 mL of MeOH, HCl gas was bubbled in for 2 h. The reaction mixture was stirred for 18 h, and then concentrated in vacuo to give 144 mg of a yellow oil. Trituration with 10 mL of ether provided 100 mg of the titled product as a white solid. $^1$H NMR (CDCl$_3$) δ 2.10–2.25 (m, 1H), 2.28–2.42 (m, 1H), 2.64–2.82 (m, 4H), 3.87 (s, 3H), 9.21 (br s, 3H).

5. Preparation of racemic (1R,2R)/(1S,2S) 1-Amino-2-ethylcyclopropanecarboxylic acid tert-butyl ester, shown below.

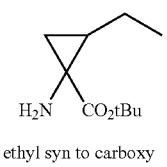

ethyl syn to carboxy

Step 1: Preparation of 2-Ethylcyclopropane-1,1-dicarboxylic acid di-tert-butyl ester, shown below.

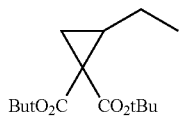

To a suspension of benzyltriethylammonium chloride (21.0 g, 92.2 mmol) in a 50% aqueous NaOH solution (92.4 g in 185 mL H₂O) was added 1,2-dibromobutane (30.0 g, 138.9 mmol) and di-tert-butylmalonate (20.0 g, 92.5 mmol). The reaction mixture was vigorously stirred 18 h at rt, a mixture of ice and water was then added. The crude product was extracted with CH₂Cl₂ (3×) and sequentially washed with water (3×), brine and the organic extracts combined. The organic layer was dried (MgSO₄), filtered and concentrated in vacuo. The resulting residue was flash chromatographed (100 g SiO₂, 3% Et₂O in hexane) to afford the titled product (18.3 g, 67.8 mmol, 73% yield) which was used directly in the next reaction.

Step 2: Preparation of racemic 2-Ethylcyclopropane-1,1-dicarboxylic acid tert-butyl ester, shown below.

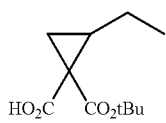

The product of Step 1 (18.3 g, 67.8 mmol) was added to a suspension of potassium tert-butoxide (33.55 g, 299.0 mmol) in dry ether (500 mL) at 0° C., followed by H₂O (1.35 mL, 75.0 mmol) and was vigorously stirred overnight at rt. The reaction mixture was poured in a mixture of ice and water and washed with ether (3×). The aqueous layer was acidified with a 10% aq. citric acid solution at 0° C. and extracted with EtOAc (3×). The combined organic layers were washed with water (2×), brine, dried (MgSO₄) and concentrated in vacuo to afford the titled product as a pale yellow oil (10 g, 46.8 mmol, 69% yield).

Step 3: Preparation of (1R,2R)/(1S,2S) 2-Ethyl-1-(2-trimethylsilanylethoxycarbonylamino)cyclopropane-carboxylic acid tert-butyl ester, shown below.

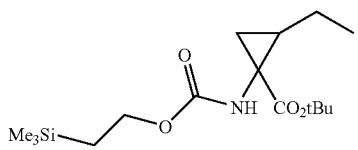

To a suspension, of the product of Step 2 (10 g, 46.8 mmol) and 3 g of freshly activated 4A molecular sieves in dry benzene (160 mL), was added Et₃N (7.50 mL, 53.8 mmol) and DPPA (11 mL, 10.21 mmol). The reaction mixture was refluxed for 3.5 h, 2-trimethylsilyl-ethanol (13.5 mL, 94.2 mmol) was then added, and the reaction mixture was refluxed overnite. The reaction mixture was filtered, diluted with Et₂O, washed with a 10% aqueous citric acid solution, water, saturated aqueous NaHCO₃, water (2×), brine (2×), dried (MgSO₄) and concentrated in vacuo. The residue was suspended with 10 g of Aldrich polyisocyanate scavenger resin in 120 mL of CH₂Cl₂, stirred at rt overnite and filtered to afford the titled product (8 g, 24.3 mmol; 52%) as a pale yellow oil: ¹H NMR (CDCl₃) δ 0.03 (s, 9H), 0.97 (m, 5H), 1.20 (bm, 1H), 1.45 (s, 9H), 1.40–1.70 (m, 4H), 4.16 (m, 2H), 5.30 (bs, 1H).

Step 4: Preparation of racemic (1R,2R)/(1S,2S) 1-Amino-2-ethylcyclopropanecarboxylic acid tert-butyl ester, shown below.

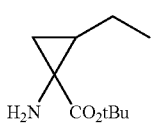

ethyl syn to carboxy

To the product of Step 3 (3 g, 9 mmol) was added a 1.0 M TBAF solution in THF (9.3 mL, 9.3 mmol) and the mixture heated to reflux for 1.5 h, cooled to rt and then diluted with 500 ml of EtOAc. The solution was successively washed with water (2×100 mL), brine (2×100 mL), dried (MgSO₄), concentrated in vacuo to provide the title intermediate.

6. Preparation of 1-Amino-spiro[2.3]hexane-1-carboxylic acid methyl ester hydrochloride salt

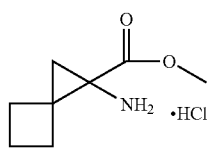

Step 1 Preparation of [2,3]hexane-1,1-dicarboxylic acid dimethyl ester, shown below.

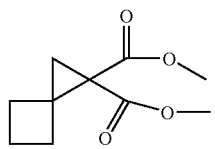

To a mixture of methylene-cyclobutane (1.5 g, 22 mmol) and Rh₂(OAc)₄ (125 mg, 0.27 mmol) in anhydrous CH₂Cl₂ (15 mL) was added 3.2 g (20 mmol) of dimethyl diazomalonate (prepared according to J. Lee et al. *Synth. Comm.*, 1995, 25, 1511–1515) at 0° C. over a period of 6 h. The reaction mixture was then warmed to rt and stirred for another 2 h. The mixture was concentrated and purified by flash chromatography (eluting with 10:1 hexane/Et₂O to 5:1 hexane/Et₂O) to give 3.2 g (72%) of [2,3]hexane-1,1-dicarboxylic acid dimethyl ester as a yellow oil. ¹H NMR (300 MHz, CDCl₃) δ 3.78 (s, 6H), 2.36 (m, 2H), 2.09 (m, 3H), 1.90 (m, 1H), 1.67 (s, 2H). LC-MS: MS m/z 199 (M⁺+1).

Step 2: Preparation of spiro[2,3]hexane-1,1-dicarboxylic acid methyl ester, shown below.

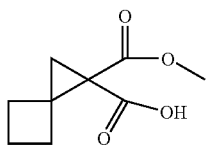

To the mixture of spiro [2,3]hexane-1,1-dicarboxylic acid dimethyl ester (200 mg, 1.0 mmol) in 2 mL of MeOH and 0.5 mL of water was added KOH (78 mg, 1.4 mmol). This solution was stirred at rt for 2 days. It was then acidified with dilute HCl and extracted two times with ether. The combined organic phases were dried (MgSO$_4$) and concentrated to yield 135 mg (73%) of 2 as a white solid. $^1$H NMR (300 MHz, CDCl$_3$) δ 3.78 (s, 3H), 2.36–1.90 (m, 8H). LC-MS: MS m/z 185 (M$^+$+1).

Step 3: Preparation of the titled product, 1-amino-spiro[2.3]hexane-1-carboxylic acid methyl ester hydrochloride salt.

To a mixture of spiro[2,3]hexane-1,1-dicarboxylic acid methyl ester (660 mg, 3.58 mmol) in 3 mL of anhydrous t-BuOH was added 1.08 g (3.92 mmol) of DPPA and 440 mg (4.35 mmol) of Et$_3$N. The mixture was heated at reflux for 21 h and then partitioned between H$_2$O and ether. The ether phase was dried over magnesium sulfate, filtered and concentrated in vacuo to yield an oil. To this oil was added 3 mL of a 4 M HCl/dioxane solution. This acidic solution was stirred at rt for 2 h and then concentrated in vacuo. The residue was triturated with ether to give 400 mg (58%) of desried prodict as a white solid. $^1$H NMR (300 MHz, d6-DMSO) δ 8.96 (br s, 3H), 3.71 (s, 3H), 2.41 (m, 1H), 2.12 (m, 4H), 1.93 (m, 1H), 1.56 (q, 2H, J=8 Hz). LC-MS of free amine: MS m/z 156 (M$^+$+1).

7. Preparation of 1-Amino-spiro[2.4]heptane-1-carboxylic acid methyl ester hydrochloride salt, shown below, was prepared as follows.

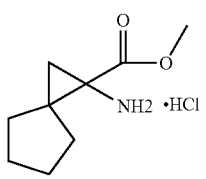

Step 1: Spiro[2.4]heptane-1,1-dicarboxylic acid dimethyl ester, shown below, was prepared as follows.

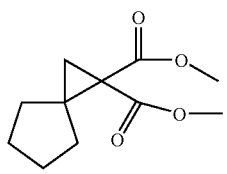

Using the same procedure described in the preparation of 1-Amino-spiro[2.3]hexane-1-carboxylic acid methyl ester hydrochloride salt 1.14 g (13.9 mmol) of methylenecyclopentane and 2.0 g (12.6 mmol) of dimethyl diazomalonate were reacted to yield 1.8 g (67%) of the dimethyl ester. $^1$H NMR (300 MHz, CDCl$_3$) δ 3.73 (s, 6H), 1.80 (m, 2H), 1.70 (m, 4H), 1.60 (m, 4H). LC-MS: MS m/z 213 (M$^+$+1).

Step 2: Preparation of Spiro[2.4]heptane-1,1-dicarboxylic acid methyl ester, shown below, was prepared as follows.

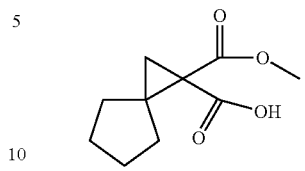

Using the same procedure described in the preparation of 1-Amino-spiro[2.3]hexane-1-carboxylic acid methyl ester hydrochloride salt 1.7 g (8.0 mmol) of the produc of Step 1 and 493 mg (8.8 mmol) of KOH gave 1.5 g (94%) of spiro[2.4]heptane-1,1-dicarboxylic acid methyl ester. $^1$H NMR (300 MHz, CDCl$_3$) δ 3.80 (s, 3H), 2.06 (d, 1H, J=5 Hz), 1.99 (d, 1H, J=5 Hz), 1.80–1.66 (m, 8H). LC-MS: MS m/z 199 (M$^+$+1).

Step 3: Preparation of 1-Amino-spiro[2.4]heptane-1-carboxylic acid methyl ester hydrochloride salt, shown below, was prepared as follows.

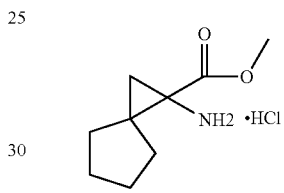

Using the same procedure described above in preparation of 1-Amino-spiro[2.3]hexane-1-carboxylic acid methyl ester hydrochloride salt, 500 mg (2.5 mmol) of the product of Step 2, 705 mg (2.5 mmol) of DPPA and 255 mg (2.5 mmol) of Et$_3$N gave 180 mg (35%) of this hydrochloride salt. $^1$H NMR (300 MHz, d6-DMSO) δ 8.90 (br s, 3H), 3.74 (s, 3H), 1.84 (m, 1H), 1.69 (m, 4H), 1.58 (m, 4H), 1.46 (d, 1H, J=6 Hz). LC-MS of free amine: MS m/z 170 (M$^+$+1).

8. Preparation of 1-Amino-spiro[2.2]pentane-1-carboxylic acid methyl ester hydrochloride salt, shown below, was prepared as follows.

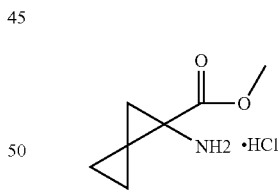

Step 1: Spiro[2.2]pentane-1,1-dicarboxylic acid dimethyl ester, shown below, was prepared as follows.

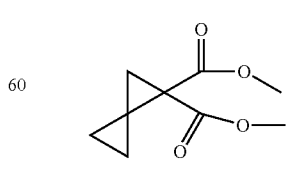

To a mixture of methylenecyclopropane (1.0 g, 18.5 mmol)(prepared according to P. Binger U.S. Pat. Ser. No. 5,723,714) and Rh$_2$(OAc)$_4$ (82 mg, 0.185 mmol) in anhydrous CH$_2$Cl$_2$ (10 mL), was added dimethyl diazomalonate (2.9 g, 18.3 mmol) at 0° C. At the top of the flask was installed a cold finger, the temperature of which was kept at −10° C. The reaction mixture was warmed to rt and stirred for another 2 h. The mixture was concentrated in vacuo and purified by flash chromatography (eluting with 10:1 hexane/Et$_2$O to 5:1 hexane/Et$_2$O) to give 0.85 g (25%) of the dimethyl ester as a yellow oil. $^1$H NMR (300 MHz, CDCl$_3$) δ 3.73 (s, 6H), 1.92 (s, 2H), 1.04 (d, 4H, J=3 Hz).

Step 2: Spiro[2.2]pentane-1,1-dicarboxylic acid methyl ester, shown below, was prepared as follows.

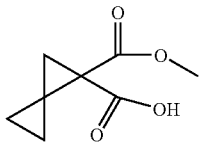

Using the same procedure described above in preparation of 1-Amino-spiro[2.3]hexane-1-carboxylic acid methyl ester hydrochloride salt, 800 mg (4.3 mmol) of the product of step 1 and 240 mg (4.3 mmol) of KOH gave 600 mg (82%) of Spiro[2.2]pentane-1,1-dicarboxylic acid methyl ester. $^1$H NMR (300 MHz, CDCl$_3$) δ 3.82 (s, 6H), 2.35 (d, 1H, J=3 Hz), 2.26 (d, 1H, J=3 Hz), 1.20 (m, 1H), 1.15 (m, 1H), 1.11 (m, 1H), 1.05 (m, 1H). LRMS: MS m/z 169 (M$^+$−1) (Method D).

Step 3: 1-Amino-spiro[2.2]pentane-1-carboxylic acid methyl ester hydrochloride salt, shown below, was prepared as follows.

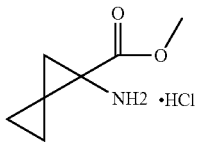

Using the same procedure described above for the preparation of 1-Amino-spiro[2.3]hexane-1-carboxylic acid methyl ester hydrochloride salt, 400 mg (2.3 mmol) of the product of step 2, 700 mg (2.5 mmol) of DPPA and 278 mg (2.7 mmol) of Et$_3$N gave 82 mg (20%) of the hydrochloride salt. $^1$H NMR (300 MHz, CDCl$_3$) δ 9.19 (br s, 3H), 3.81 (s, 3H), 2.16, (d, J=5.5 Hz, 1H), 2.01 (d, J=5.5 Hz, 1H), 1.49 (m, 1H), 1.24, (m, 1H), 1.12 (m, 2H). LRMS of free amine: MS m/z 142 (M$^+$+1).

9. Preparation of 5-Amino-spiro[2.3]hexane-5-carboxylic acid ethyl ester, shown below, was prepared as follows.

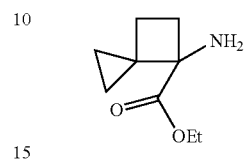

Spiro[2.3]hexan-4-one (500 mg, 5 mmol), which was prepared from bicyclopropylidene (A. Meijere et al. *Org. Syn.* 2000, 78, 142–151) according to A. Meijere et al. *J. Org. Chem.* 1988, 53, 152–161, was combined with ammonium carbamate (1.17 g, 15 mmol) and potassium cyanide (812 mg, 12.5 mmol) in 50 mL of EtOH and 50 mL of water. The mixture was heated at 55° C. for 2 days. Then NaOH (7 g, 175 mmol) was added and the solution was heated under reflux overnight. The mixture was then chilled to 0° C., acidified to pH 1 with concentrated HCl, and concentrated in vacuo. EtOH was added to the crude amino acid mixture and then concentrated to dryness (5×) so as to remove residual water. The residue dissolved in 100 mL of EtOH was cooled to 0° C. It was then treated with 1 mL of SOCl$_2$ and refluxed for 3 days. The solids were removed by filtration, and the filtrate was concentrated in vacuo to give the crude product. The crude product was partitioned between 3 N NaOH, NaCl and EtOAc. The organic phase was dried over potassium carbonate and concentrated. The residue was purified using column chromatography on C18 silica gel (eluting with MeOH/H$_2$O) to yield 180 mg (21%) of 15 as an oil. $^1$H NMR (300 MHz, CDCl$_3$) δ 8.20 (br s, 2H), 4.27 (s, 2H), 2.80 (s, 1H), 2.54 (s, 1H), 2.34 (m, 2H), 1.31 (s, 3H), 1.02 (s, 1H), 0.66 (m, 3H). $^{13}$C NMR (300 MHz, CDCl$_3$) δ 170.2(s), 63.0(s), 62.8 (s), 26.1 (s), 26.0 (s), 24.9 (s), 13.9 (s), 11.4 (s), 10.9 (s). LC-MS: MS m/z 170 (M$^+$+1).

II Heterocycles to be Used as Starting Material in the Construction of P2 Elements for Subsequent Incorporation into Compounds of Formula I.

1. Isoquinolines

(1)
Commercial material

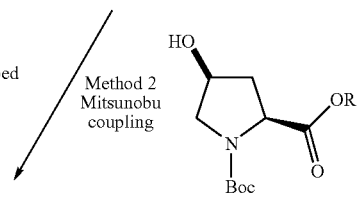

Method 1
alkoxide promoted coupling using the chemistry described in the following sections Method 2
Mitsunobu coupling

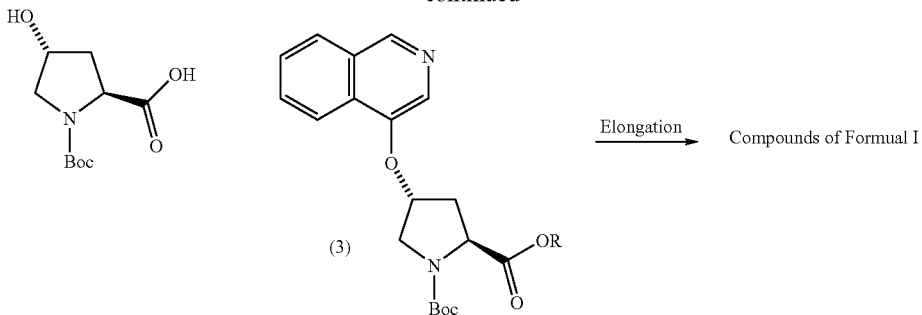

Isoquinoline (1) and substituted analogues thereof, can be incorporated into P2 elements using the two methods outline above and described in detail herein. Said P2 elements (3) can then be converted into compounds of Formula I using procedures analogous to those described herein for similar isoquinoline analogues.

2. Isoxazolepyridine and Oxazolepyridine (1)

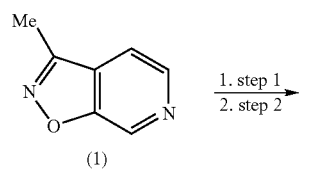

(1) is a known compound:
see: *Organic Mag Resonance*
(1982), 20(3), 141–4 and: *JCS PT1 (organic and bio-organic chemistry)*
1972–1999) (1975), (21), 2190–4

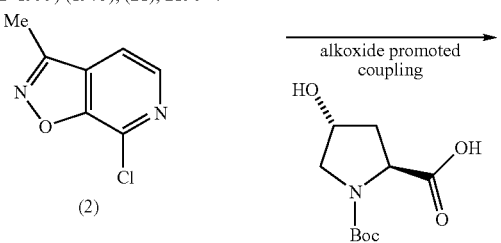

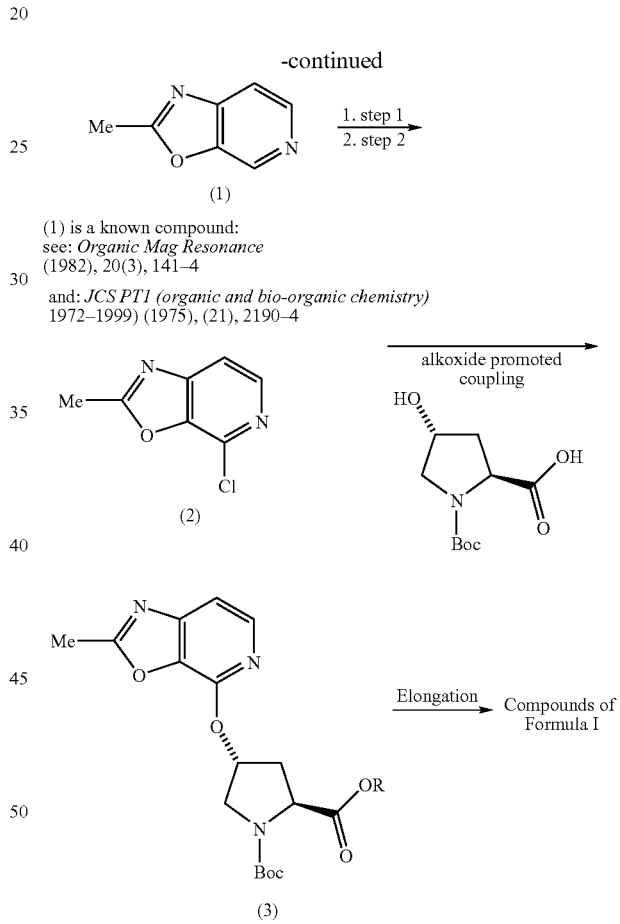

(1) is a known compound:
see: *Organic Mag Resonance*
(1982), 20(3), 141–4 and: *JCS PT1 (organic and bio-organic chemistry)*
1972–1999) (1975), (21), 2190–4

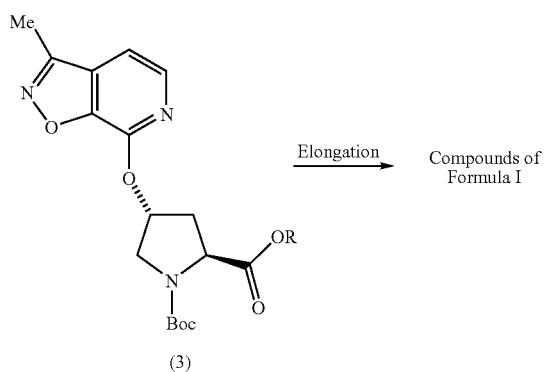

Isoxazole and oxazole heterocycle (1) and analogues thereof can be prepared using know chemistry and incorporated into compounds of Formula I using the chemistry described herein for similar isoxazolepyridine intermediates as shown in section B.

III P1 Prime Elements:

The P1 prime elements prepared below can be used to prepare compounds of Formula I by using the methods described herein.

1. Preparation of Cyclopropylsulfonamide:

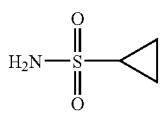

Step 1: Preparation of N-tert-Butyl-(3-chloro)propylsulfonamide

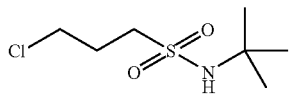

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to rt and stirred for 24 h. The mixture was filtered, and the filtrate was concentrated in vacuo. The residue was dissolved in $CH_2Cl_2$ (2.0 L). The resulting solution was washed with 1 N HCl (1.0 L), water (1.0 L), brine (1.0 L) and dried over $Na_2SO_4$. It was filtered and concentrated in vacuo to give a slightly yellow solid, which was crystallized from hexane to afford the product as a white solid (316.0 g, 99%).

$^1$H NMR (CDCl$_3$) δ 1.38 (s, 9H), 2.30–2.27 (m, 2H), 3.22 (t, J=7.35 Hz, 2H), 3.68 (t, J=6.2 Hz, 2H), 4.35 (b, 1H).

Step 2: Preparation of Cyclopropanesulfonic acid tert-butylamide

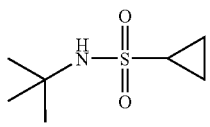

To a solution of N-tert-butyl-(3-chloro)propylsulfonamide (2.14 g, 10.0 mmol) in THF (100 mL) was added n-BuLi (2.5 M in hexane, 8.0 mL, 20.0 mmol) at −78° C. The reation mixture was allowed to warm up to room temperature over period of 1 h. The volatiles were removed in vacuo. The residue was partitioned between EtOAC and water (200 mL, 200 mL). The separated organic phase was washed with brine, dried over $Na_2SO_4$, filtered and concentrated in vacuo. The residue was recrystallized from hexane to yield the desired product as a white solid (1.0 g, 56%).

$^1$H NMR (CDCl$_3$) δ 0.98–1.00 (m, 2H), 1.18–1.19 (m, 2H), 1.39 (s, 9H), 2.48–2.51 (m, 1H), 4.19 (b, 1H).

Step 3: Preparation of Cyclopropylsulfonamide

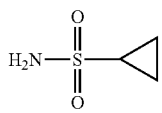

A solution of cyclopropanesulfonic acid tert-butylamide (110.0 g, 0.62 mol) in TFA (500 mL) was stirred at room temperature for 16 h. The volatile was removed in vacuo. The residue was recrystallized from EtOAC/hexane (60 mL/240 mL) to yield the desired product as a white solid (68.5 g, 91%).

$^1$H NMR (DMSO-d$_6$) δ 0.84–0.88 (m, 2H), 0.95–0.98 (m, 2H), 2.41–2.58 (m, 1H), 6.56 (b, 2H).

2. Alternate Procedure for the Preparation of Cyclopropyl Sulfonamide

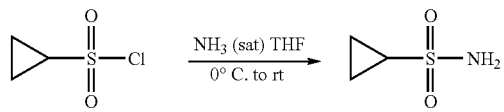

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1–2 mL of solvent remained, applied onto 30 g plug of SiO$_2$ (eluted with 30% to 60% EtOAc/Hexanes) to afford 3.45 g (100%) of cyclopropyl sulfonamide as a white solid. $^1$H NMR (Methanol-d$_4$) δ 0.94–1.07 (m, 4H), 2.52–2.60 (m, 1H); $^{13}$C NMR (methanol-d$_4$) δ 5.92, 33.01.

3. Preparation of Cyclobutyl Sulfonamide

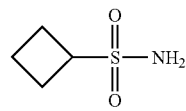

To a solution of 5.0 g (37.0 mmol) of cyclobutyl bromide in 30 mL of anhydrous diethyl ether (Et$_2$O) cooled to −78° C. was added 44 mL (74.8 mmol) of 1.7M tert-butyl lithium in pentanes and the solution slowly warmed to −35° C. over 1.5 h. This mixture was cannulated slowly into a solution of 5.0 g (37.0 mmol) freshly distilled sulfuryl chloride in 100 mL of hexanes cooled to −40° C., warmed to 0° C. over 1 h and carefully concentrated in vacuo. This mixture was redissolved in Et$_2$O, washed once with some ice-cold water, dried (MgSO$_4$) and concentrated carefully. This mixture was redissolved in 20 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1–2 drops of MeOH to afford 1.90 g (38%) of cyclobutylsulfonamide as a white solid. $^1$H NMR (CDCl$_3$) δ 1.95–2.06 (m, 2H), 2.30–2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M–H)$^-$ calcd for C$_4$H$_8$NSO$_2$: 134.0276, found 134.0282.

4 Preparation of Cyclopentyl Sulfonamide

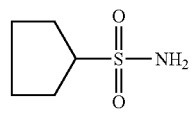

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 h and was then carefully concentrated in vacuo. This mixture was redissolved in Et₂O (200 mL), washed once with some ice-cold water (200 mL), dried (MgSO₄) and concentrated carefully. This mixture was redissolved in 35 mL of THF, added dropwise to 500 mL of saturated NH₃ in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of CH₂Cl₂ in hexanes with 1–2 drops of MeOH to afford 2.49 g (41%) of cyclopentylsulfonamide as a white solid. ¹H NMR (CDCl₃) δ 1.58–1.72 (m, 2H), 1.74–1.88 (m, 2H), 1.94–2.14 (m, 4H), 3.48–3.59 (m, 1H), 4.80 (bs, 2H); ¹³C NMR (CDCl₃) δ 25.90, 28.33, 63.54; MS m/e 148 (M−H)⁻.

5. Preparation of Cyclohexyl Sulfonamide

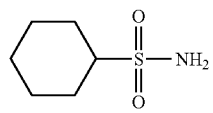

A solution of 18.5 mL (37.0 mmol) of 2M cyclohexylmagnesium chloride (TCI Americas) in ether was added dropwise to a solution of 3.0 mL (37.0 mmol) freshly distilled sulfuryl chloride in 100 mL of hexanes cooled to −78° C. The mixture was warmed to 0° C. over 1 h and was then carefully concentrated in vacuo. This mixture was redissolved in Et₂O (200 mL), washed once with some ice-cold water (200 mL), dried (MgSO₄) and concentrated carefully This mixture was redissolved in 35 mL of THF, added dropwise to 500 mL of saturated NH₃ in THF and was allowed to stir overnite. The mixture was concentrated in vacuo to a crude yellow solid, the residue filtered through 50 g of silica gel using 70% EtOAc-hexanes as the eluent and was concentrated. The residue was recrystallized from the minimum amount of CH₂Cl₂ in hexanes with 1–2 drops of MeOH to afford 1.66 g (30%) of cyclohexyl-sulfonamide as a white solid: ¹H NMR (CDCl₃) δ 1.11–1.37 (m, 3H), 1.43–1.56 (m, 2H), 1.67–1.76 (m, 1H), 1.86–1.96 (m, 2H), 2.18–2.28 (m, 2H), 2.91 (tt, J=12, 3.5 Hz, 1H), 4.70 (bs, 2H); ¹³CH NMR (CDCl₃) δ 25.04, 25.04, 26.56, 62.74; MS m/e 162 (M−1)⁻.

6. Preparation of Substituted Cycloalkyllsulfonamides for Use in the Construction of Compounds of Formula 1.

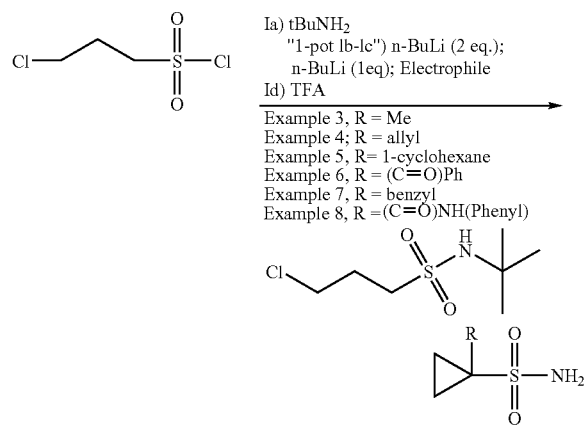

Preparation of N-tert-Butyl-(3-chloro)propylsulfonamide.
As Described Above.

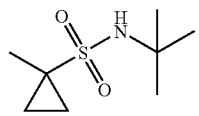

Preparation of N-tert-Butyl-(1-methyl)cyclopropyl-sulfonamide.

A solution of N-tert-Butyl-(3-chloro)propylsulfonamide (4.3 g, 20 mmol) was dissolved in dry THF (100 mL) and cooled to −78° C. To this solution was added n-BuLi (17.6 mL, 44 mmol, 2.5 M in hexane) slowly. The dry ice bath was removed and the reaction mixture was allowed to warm to rt over a period of 1.5 h. This mixture was then cooled to −78° C., and a solution of n-BuLi (20 mmol, 8 mL, 2.5 M in hexane) was added. The reaction mixture was warmed to rt, recooled to −78° C. over a period of 2 h and a neat solution of methyliodide (5.68 g, 40 mmol) added. The reaction mixture was allowed to warm to rt overnight, quenched with saturated NH₄Cl (100 mL) at rt. It was extracted with EtOAc (100 mL). The organic phase was washed with brine (100 mL), dried (MgSO₄), and concentrated in vacuo to give a yellow oil which was crystallized from hexane to afford the product as a slightly yellow solid (3.1 g, 81%): ¹H NMR (CDCl₃) δ 0.79 (m, 2H), 1.36 (s, 9H), 1.52 (m, 2H), 1.62 (s, 3H), 4.10 (bs, 1H).

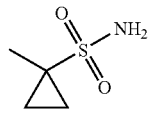

Preparation of Example 3

1-methylcyclopropylsulfonamide.

A solution of N-tert-Butyl-(1-methyl)cyclopropylsulfonamide (1.91 g, 10 mmol) was dissolved in TFA (30 mL), and the reaction mixture stirred at rt for 16 h. The solvent was removed in vacuo to give a yellow oil which was crystallized from EtOAc/hexane (1:4, 40 mL) to yield Example 3,1-methylcyclopropylsulfonamide, as a white solid (1.25 g, 96%): ¹H NMR (CDCl₃) δ 0.84 (m, 2H), 1.41 (m, 2H), 1.58 (s, 3H), 4.65 (bs, 2H). Anal. Calcd. For C₄H₉NO₂S: C, 35.54; H, 6.71; N, 10.36. Found: C, 35.67; H, 6.80; N, 10.40.

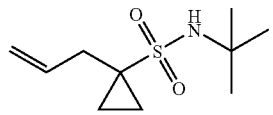

Preparation of N-tert-Butyl-(1-allyl)cyclopropylsulfonamide.

This compound, N-tert-Butyl-(1-allyl)cyclopropylsulfonamide, was obtained in 97% yield according to the procedure described in the synthesis of N-tert-Butyl-(1-methyl)cyclopropylsul-fonamide except 1.25 equivalents of allyl bromide were used as electrophile. The compound was taken directly into the next reaction without purification: $^1$H NMR (CDCl$_3$) δ 0.83 (m, 2H), 1.34 (s, 9H), 1.37 (m, 2H), 2.64 (d, J=7.3 Hz, 2H), 4.25 (bs, 1H), 5.07–5.10 (m, 2H), 6.70–6.85 (m, 1H).

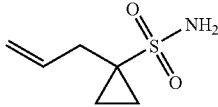

Preparation of Example 4

1-allylcyclopro-pylsulfonamide.

Example 4,1-allylcyclopropylsulfonamide, was obtained in 40% yield from N-tert-butyl-(1-allyl)cyclopropylsulfonamide according to the procedure described in the synthesis of 1-Methylcyclopropylsulfonamide. The compound was purified by column chromotography over SiO$_2$ using 2% MeOH in CH$_2$Cl$_2$ as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

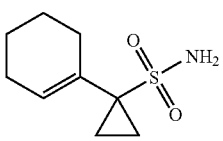

Preparation of N-tert-Butyl-[1-(1-hydroxy)cyclohexyl]-cyclopropylsulfonamide.

This compound was obtained in 84% yield using to the procedure described for the synthesis of N-tert-Butyl-(1-methyl)cyclopropylsul-fonamide except 1.30 equivalents of cyclohexanone were used, followed by recrystallization from the minimum amount of 20% EtOAc in hexane: $^1$H NMR (CDCl$_3$) δ 1.05 (m, 4H), 1.26 (m, 2H), 1.37 (s, 9H), 1.57–1.59 (m, 6H), 1.97 (m, 2H), 2.87 (bs, 1H), 4.55 (bs, 1H).

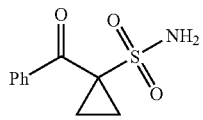

Preparation of Example 5

1-(1-cyclohexenyl)cyclopropyl-sulfonamide.

This compound, 1-(1-cyclohexenyl)-cyclopropylsulfonamide, Example 5, was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of EtOAc and hexane: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$–1).

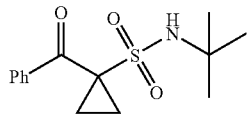

Preparation of N-tert-Butyl-(1-benzoyl)cyclopropyl-sulfonamide.

This compound was obtained in 66% yield using the procedure described for the synthesis of N-tert-Butyl-(1-methyl)cyclopropylsulfonamide except 1.2 equivalents of methyl benzoate was used as the electrophile. The compound was purified by column chromatography over SiO$_2$ using 30% to 100% CH$_2$Cl$_2$ in hexane: $^1$H NMR (CDCl$_3$) δ 1.31 (s, 9H), 1.52 (m, 2H), 1.81 (m, 2H), 4.16 (bs, 1H), 7.46 (m, 2H), 7.57 (m, 1H), 8.05 (d, J=8.5 Hz, 2H).

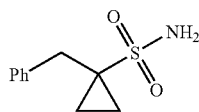

Preparation of Example 6

1-benzoylcyclo-propylsulfonamide.

This compound, Example 6,1-benzoylcyclopropyl-sulfonamide, was obtained in 87% yield from N-tert-butyl(1-benzoyl)cyclopropylsul-fonamide using the procedure described for the synthesis of 1-Methylcyclopropylsulfonamide, followed by recrystallization from the minimum amount of EtOAc in hexane: $^1$H NMR (DMSO-d$_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO d6) δ 12.3, 48.4, 128.1, 130.0, 133.4, 135.3, 192.0.

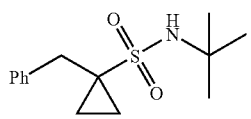

Preparation of N-tert-Butyl-(1-benzyl)cyclopropyl-sulfonamide.

This compound was obtained in 60% yield using the procedure described for the synthesis of N-tert-Butyl-(1-methyl)cyclopropylsulfonamide except 1.05 equivalents of benzyl bromide were used, followed by trituration with 10% EtOAc in hexane: $^1$H NMR (CDCl$_3$) δ 0.92 (m, 2H), 1.36 (m, 2H), 1.43 (s, 9H), 3.25 (s, 2H), 4.62 (bs, 1H), 7.29–7.36 (m, 5H).

Preparation of Example 7

1-Benzylcyclo-propylsulfonamide.

This compound, Example 7,1-Benzylcyclopropylsulfonamide, was obtained in 66% yield from N-tert-butyl(1-benzyl)cyclopropylsul-fonamide using the procedure described for the synthesis of 1-Methylcyclopropylsulfonamide, followed by recrystallization from the minimum amount of 10% EtOAc in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

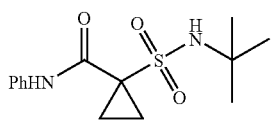

Preparation of N-tert-Butyl-(1-phenylaminocarboxy)-cyclopropylsulfonamide.

This compound was obtained in 42% yield using the procedure described for the synthesis of N-tert-Butyl-(1-methyl)cyclopropylsulfonamide using 1 equivalent of phenylisocyanate, followed by recrystallization from the minimum amount of EtOAc in hexane $^1$H NMR (CDCl$_3$) δ 1.38 (s, 9H), 1.67–1.71 (m, 4H), 4.30 (bs, 1H), 7.10 (t, J=7.5 Hz, 1H), 7.34 (t, J=7.5 Hz, 2H), 7.53 (t, J=7.5 Hz, 2H).

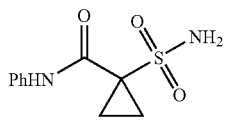

Sections B through I: Preparation of Compounds

Section B: Preparation of Compounds 100–113

Preparation of 2(S)-[1(R)-(1-Ethyl-cyclopropanesulfonylaminocarbonyl)-2(S)-vinyl-cyclopropylcarbamoyl]-N-[N-Boc-amino-(S)-t-butyl-acetyl]4(R)-hydroxy-pyrrolidine

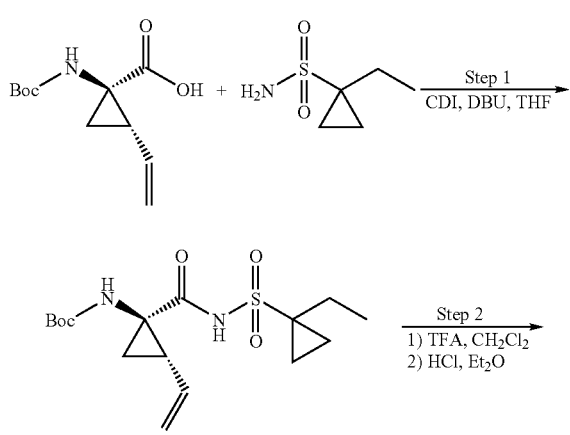

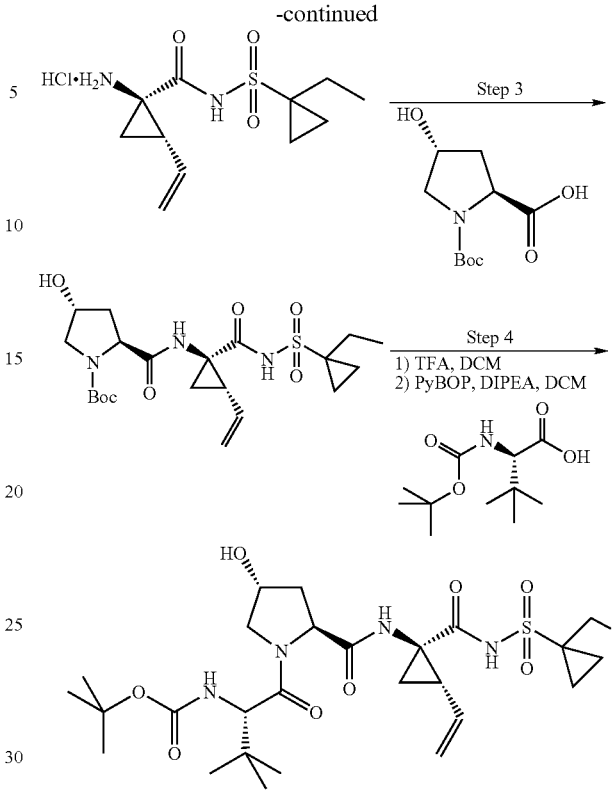

Step 1:

A mixture of 1(R)-N-Boc-amino-2(S)-vinyl-cyclopropanecarboxylic acid (3.41 g, 15 mmol) and CDI (2.46 g, 16.5 mmol) in THF (40 ml) was refluxed for 1 h. The solution was cooled to room temperature and transferred into a solution of 1-ethyl-cyclopropylsulfonamide (2.46 g, 16.5 mmol) in THF (10 ml). DBU (2.7 ml, 18 mmol) was added and the resulting mixture was stirred at room temperature overnight. The reaction was quenched with 1N HCl to pH 1 and the solvent was evaporated in vacuo. The residue was extracted with EtOAc (3×100 ml). The combined organic extracts were washed with brine, dried over MgSO$_4$ and concentrated in vacuo. The crude product was purified by flash column chromatograph (Biotage Flash 40M) eluted with EtOAc to give the desired product (1.72 g, 32%). $^1$H NMR (400 MHz, CD$_3$OD) δ ppm 0.92 (m, 2H), 0.98 (t, J=7.46 Hz, 3H), 1.27 (dd, J=9.54, 5.38 Hz, 1H), 1.47 (m, 11H), 1.81 (dd, J=7.83, 5.62 Hz, 1H), 1.91 (m, 2H), 2.18 (m, 1H), 5.09 (dd, J=10.27, 1.47 Hz, 1H), 5.27 (dd, J=17.24, 1.59 Hz, 1H), 5.53 (m, 1H); MS 359 (M+H)$^+$.

Step 2:

A solution of 1-ethyl-cyclopropanesulfonic acid [1(R)-N-Boc-amino-2(S)-vinyl-cyclopropanecarbonyl]-amide (Product of Step 1, 1.72 g, 4.8 mmol) in TFA (15 ml) and CH$_2$Cl$_2$ (15 ml) was stirred at room temperature for 2 h. The reaction mixture was concentrated in vacuo. The residue was suspended in 1N HCl in Et$_2$O (10 ml) and concentrated in vacuo. This procedure was repeated once. The precipitate was washed with Et$_2$O, collected by filtration and dried in desiccator to give the desired product (1.40 g, 99%); MS 259 (M+H)$^+$.

Step 3:
To a mixture of Boc-Hyp-OH (1.00 g, 4.3 mmol) and 1-ethyl-cyclopropane-sulfonic acid [1(R)-amino-2(S)-vinyl-cyclopropanecarbonyl]-amide hydrochloride (Product of Step 2, 1.27 g, 4.3 mmol) in CH$_2$Cl$_2$ (10 ml) was added DIPEA (2.2 ml, 13 mmol) and PyBOP (2.36 g, 4.5 mmol). The mixture was stirred at room temperature for 1 h and concentrated in vacuo. Purification by flash column chromatograph (Biotage Flash 40M) eluted with EtOAc gave the desired product (2.00 g, 99%). MS 494 (M+Na)$^+$.

Step 4:
A solution of 2(S)-[1(R)-(1-ethyl-cyclopropanesulfonylaminocarbonyl)-2(S)-vinyl-cyclopropylcarbamoyl]-4(R)-hydroxy-N-Boc-pyrrolidine (Product of Step 3, 2.00 g, 4.2 mmol) in TFA (5 ml) and CH$_2$Cl$_2$ (5 ml) was stirred at room temperature for 1 h and concentrated in vacuo. The residue was dissolved in CH$_2$Cl$_2$ (10 ml) and Boc-L-tert-leucine (0.98 g, 4.2 mmol), DIPEA (2 ml) and PyBOP (2.32 g, 4.5 mmol) were added. The resulting mixture was stirred at room temperature overnight and the solvent was removed in vacuo. The crude product was purified by flash column chromatograph (Biotage Flash 40M) eluted with EtOAc to provide the title compound (2.01 g, 81%). $^1$H NMR (400 MHz, CDCl$_3$) δ ppm 0.96 (m, 5H), 1.01 (s, 9H), 1.39 (m, 12H), 1.83 (m, 2H), 1.96 (m, 2H), 2.17 (m, 2H), 3.81 (m, 2H), 4.29 (d, J=9.54 Hz, 1H), 4.40 (dd, J=9.78, 7.34 Hz, 1H), 4.48 (s, 1H), 5.11 (d, J=11.49 Hz, 1H), 5.28 (d, J=17.36 Hz, 1H), 5.73 (m, 1H), 6.66 (d, J=9.29 Hz, 1H); MS 607 (M+Na)$^+$.

Preparation of (1(S)-{2(S)-[1(R)-(1-Ethyl-cyclopropane-sulfonylaminocarbonyl)-2(S)-vinyl-cyclopropylcarbamoyl]-4-hydroxy-pyrrolidine-1-carbonyl}-2,2-dimethyl-propyl)-carbamic acid isopropyl ester

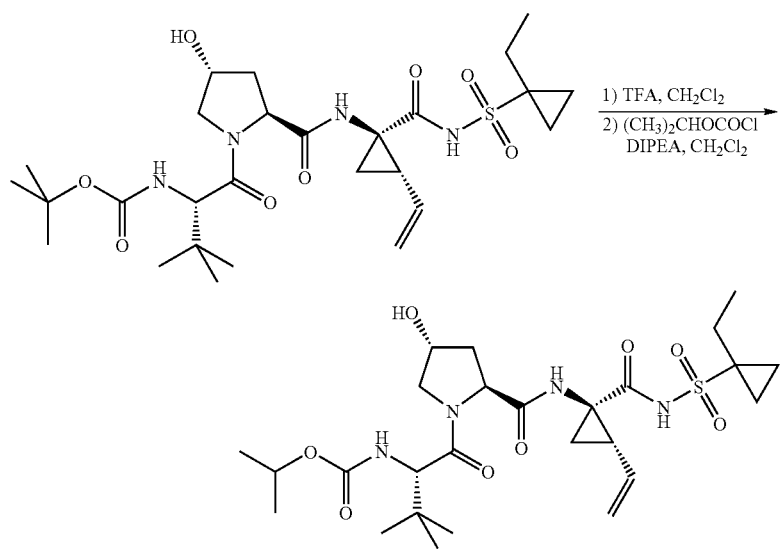

A solution of 2(S)-[1 (R)-(1-ethyl-cyclopropanesulfonylaminocarbonyl)-2(S)-vinyl-cyclopropylcarbamoyl]-N-[N-Boc-amino-(S)-t-butyl-acetyl]-4(R)-hydroxy-pyrrolidine (585 mg, 1.0 mmol) in TFA (2 ml) and CH$_2$Cl$_2$ (2 ml) was stirred at room temperature for 1 h and concentrated in vacuo. The residue was dissolved in CH$_2$Cl$_2$ (5 ml) and isopropyl chloroformate (1.0M in toluene, 1.0 ml, 1.0 mmol), DIPEA (0.5 ml) were added. The resulting mixture was stirred at room temperature overnight and the solvent was removed in vacuo. The crude product was purified by flash column chromatograph (Biotage Flash 40M) eluted with EtOAc to provide the title compound (180 mg, 32%). MS 571 (M+H)$^+$.

Example 100

Preparation of Compound 100

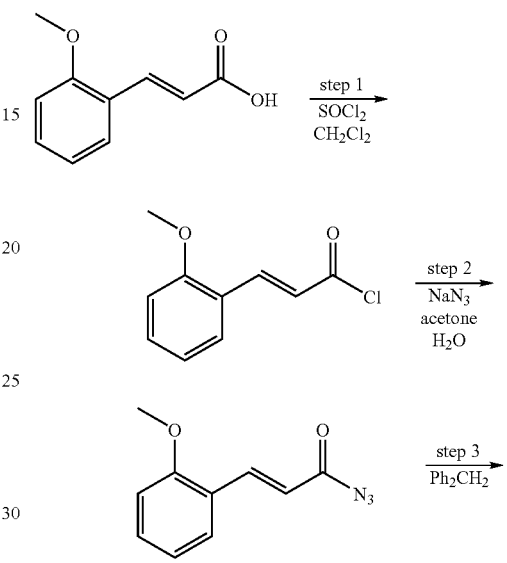

-continued

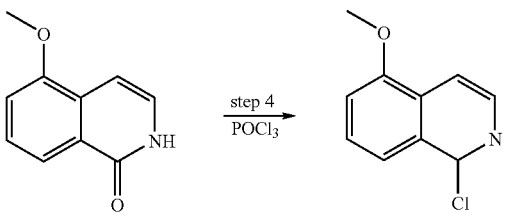

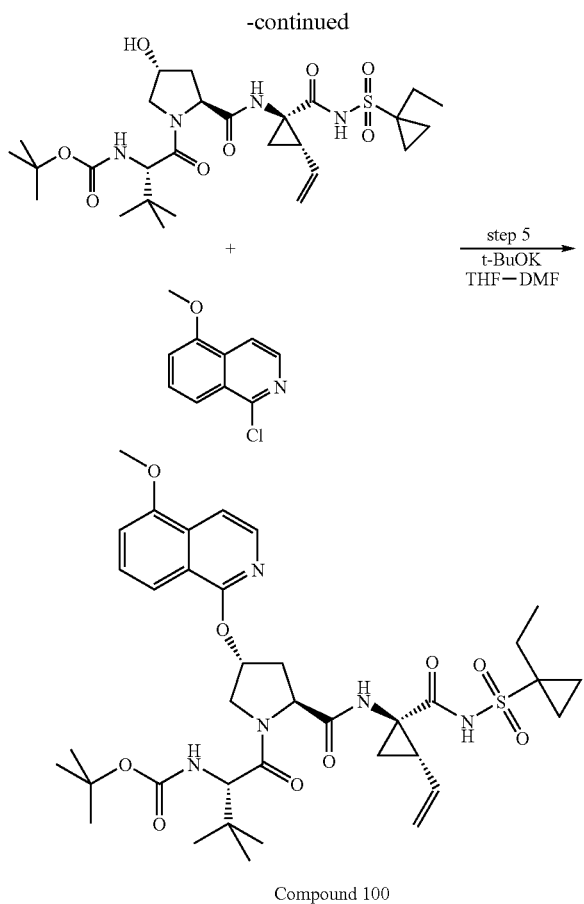

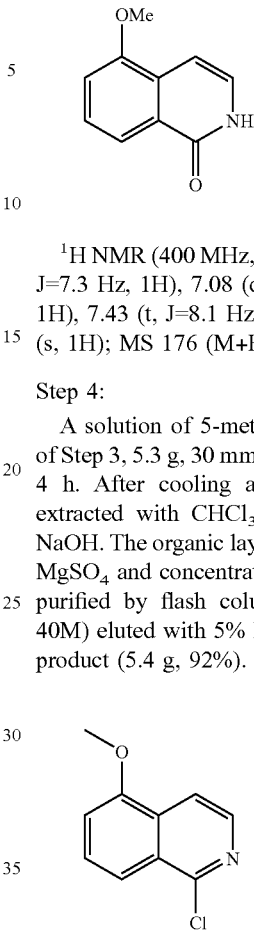

¹H NMR (400 MHz, CD₃OD) δ ppm 3.95 (s, 3H), 6.94 (d, J=7.3 Hz, 1H), 7.08 (d, J=8.1 Hz, 1H), 7.14 (d, J=7.3 Hz, 1H), 7.43 (t, J=8.1 Hz, 1H), 7.99 (d, J=8.1 Hz, 1H), 10.92 (s, 1H); MS 176 (M+H)⁺.

Step 4:

A solution of 5-methoxy-2H-isoquinolin-1-one (Product of Step 3, 5.3 g, 30 mmol) in POCl₃ (50 ml) was refluxed for 4 h. After cooling and concentration, the residue was extracted with CHCl₃ (50 ml) and neutralized with 1N NaOH. The organic layer was washed with brine, dried over MgSO₄ and concentrated in vacuo. The crude product was purified by flash column chromatograph (Biotage Flash 40M) eluted with 5% EtOAc in hexane to give the desired product (5.4 g, 92%).

¹H NMR (400 MHz, CDCl₃) δ ppm 4.01 (s, 3H), 7.04 (d, J=7.8 Hz, 1H), 7.57 (t, J=8.1 Hz, 1H), 7.88 (d, J=8.6 Hz, 1H), 7.97 (d, J=5.9 Hz, 1H), 8.25 (d, J=5.9 Hz, 1H); MS 194 (M+H)⁺.

Step 5:

A solution of 1-chloro-5-methoxy-isoquinoline (Product of Step 4, 19 mg, 0.1 mmol) and 2(S)-[1(R)-(1-ethyl-cyclopropanesulfonylaminocarbonyl)-2(S)-vinyl-cyclopropylcarbamoyl]-N-[N-Boc-amino-(S)-t-butyl-acetyl]-4(R)-hydroxy-pyrrolidine (58 mg, 0.1 mmol) in DMF (1 ml) was cooled to −78° C. and t-BuOK (1.0 M in THF, 0.75 ml) was added. The resulting mixture was warmed to room temperature and stirred overnight. The reaction was quenched with aqueous NH₄Cl and extracted with EtOAc. The organic layer was washed with brine, dried over MgSO₄ and concentrated in vacuo. The crude product was purified by Prep HPLC to give compound 100 (18 mg, 24%). ¹H NMR (400 MHz, CD₃OD) δ ppm 0.96 (m, 5H), 1.04 (s, 9H), 1.26 (s, 9H), 1.42 (m, 1H), 1.51 (m, 2H), 1.85 (m, 2H), 1.97 (m, 1H), 2.25 (m, 2H), 2.63 (dd, J=13.69, 7.58 Hz, 1H), 3.99 (s, 3H), 4.07 (dd, J=11.49, 3.42 Hz, 1H), 4.26 (s, 1H), 4.46 (d, J=11.98 Hz, 1H), 4.55 (dd, J=9.29, 7.83 Hz, 1H), 5.11 (d, J=10.27 Hz, 1H), 5.28 (d, J=17.36 Hz, 1H), 5.71 (m, 1H), 5.85 (s, 1H), 7.14 (d, J=8.07 Hz, 1H), 7.43 (t, J=7.83 Hz, 1H), 7.60 (d, J=5.62 Hz, 1H), 7.74 (d, J=8.07 Hz, 1H), 7.94 (d, J=6.11 Hz, 1H); MS 742 (M+H)⁺.

Step 1:

To a solution of 2-methoxy cinnamic acid (10.0 g) in CH₂Cl₂ (100 ml) was added thionyl chloride (40 ml). After refluxing for 4 h, the reaction mixture was concentrated in vacuo. The crude product was used for next step without purification.

Step 2:

To a solution of 3-(2-methoxy-phenyl)-acryloyl chloride (Product of Step 1, 11.0 g, 56 mmol)) in acetone (100 ml) was added sodium azide (9.1 g, 240 mmol) in water (30 ml). The mixture was stirred at room temperature for 3 h and the solvent was evaporated in vacuo. The residue was extracted with diphenylmethane (50 ml) and the organic layer was washed with water and dried over MgSO₄. This solution was used for next step without purification.

Step 3:

Diphenylmethane (50 ml) was heated to 200° C., and the solution of 3-(2-methoxy-phenyl)-acryloyl azide in diphenylmethane (Product of Step 2) was added dropwise. After completion of addition, the mixture was refluxed for 4 h and then cooled to room temperature. The precipitate was collected by filtration, washed with benzene and dried. The filtrates were concentrated in vacuo and purified by flash column chromatograph (Biotage Flash 40M) eluted with EtOAc:hexane (1:1) to give the second batch of product (total 5.3 g, 54%).

Example 101

Preparation of Compound 101

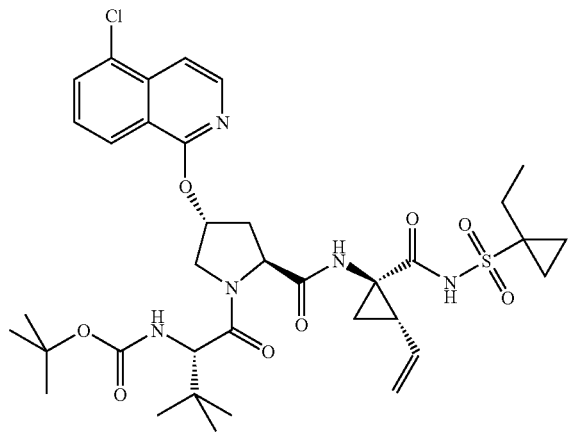
Compound 101

Compound 101 was prepared by following Steps 1 through 5 described in Example 100 except that the following modifications were made:

Step 1–3:

2-Chlorocinnamic acid (25.0 g) was used as starting material and 14.6 g (59%) of product was obtained.

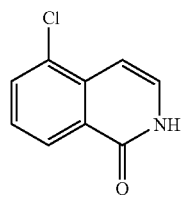

$^1$H NMR (400 MHz, CD$_3$OD) δ ppm 7.22 (d, J=7.3 Hz, 1H), 7.42 (t, J=7.8 Hz, 1H), 7.73 (d, J=7.8 Hz, 1H), 8.34 (d, J=8.1 Hz, 1H), 10.61 (s, 1H); MS 180 (M+H)$^+$.

Step 4:

5-Chloro-2H-isoquinolin-1-one (Product of Step 3, 14.6 g) was used as starting material and 8.28 g (53%) of product was obtained.

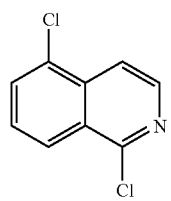

$^1$H NMR (400 MHz, CDCl$_3$) δ ppm 7.60 (dd, J=8. 6, 7.6 Hz, 1H), 7.83 (m, 1H), 8.00 (d, J=5.9 Hz, 1H), 8.29 (dt, J=8.9, 1.0 Hz, 1H), 8.38 (d, J=5.9 Hz, 1H); MS 198 (M+H)$^+$.

Step 5:

1,5-Dichloro-isoquinoline (Product of Step 4, 20 mg) was used as starting material and 24 mg (32%) of compound 101 was obtained. $^1$H NMR (400 MHz, CD$_3$OD) δ ppm 0.96 (m, 5H), 1.03 (s, 9H), 1.21 (s, 9H), 1.42 (m, 1H), 1.52 (m, 2H), 1.85 (m, 2H), 1.97 (m, 1H), 2.27 (m, 2H), 2.65 (dd, J=13.57, 6.97 Hz, 1H), 4.07 (d, J=11.49 Hz, 1H), 4.22 (s, 1H), 4.54 (m, 2H), 5.12 (d, J=10.03 Hz, 1H), 5.28 (d, J=17.12 Hz, 1H), 5.71 (m, 1H), 5.88 (s, 1H), 7.48 (t, J=7.83 Hz, 1H), 7.63 (d, J=5.38 Hz, 1H), 7.81 (d, J=7.34 Hz, 1H), 8.11 (d, J=6.11 Hz, 1H), 8.19 (d, J=8.31 Hz, 1H); MS 746 (M+H)$^+$.

Example 102

Preparation of Compound 102

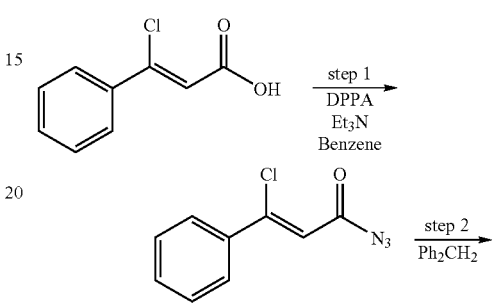

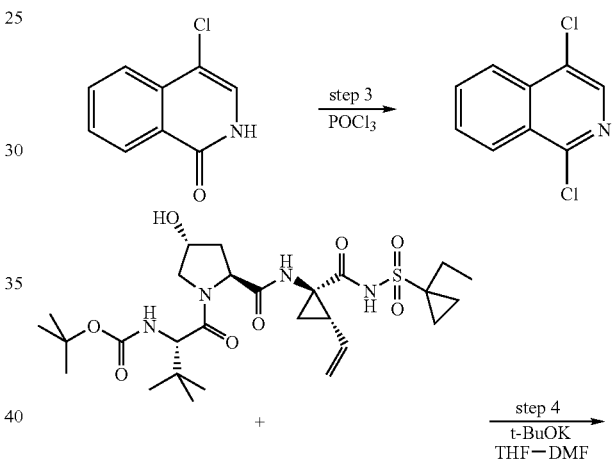

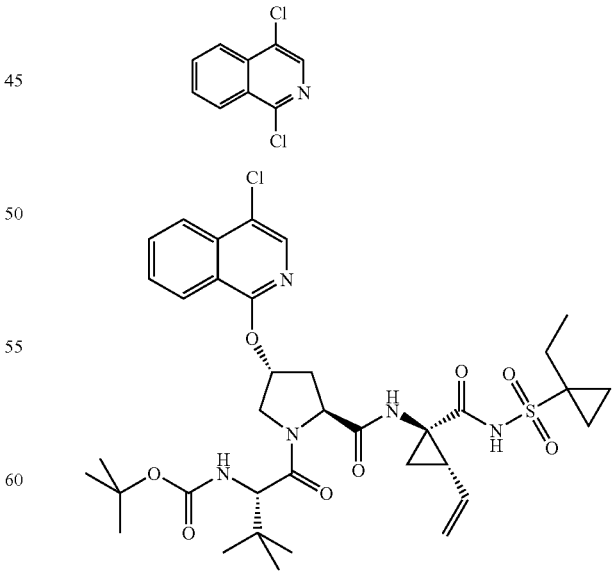
Compound 102

75

Step 1:

A solution of β-chlorocinnamic acid (11.0 g, 60 mmol), diphenylphosphoryl azide (15.7 g, 57 mmol)), and triethylamine (10 ml) in benzene (80 ml) was stirred for 1 h. The reaction mixture was concentrated in vacuo at <50° C. and purified by flash column chromatograph (Biotage Flash 40M) eluted with 10% EtOAc in hexane to give the desired product (4.1 g, 34%).

Step 2:

A solution of 3-chloro-3-phenyl-acryloyl azide (Product of Step 1, 4.1 g, 19.7 mmol) in diphenylmethane (40 ml) was heated up slowly and refluxed for 4 h. After cooling to room temperature, the precipitate was collected by filtration, washed with hexane and dried. The filtrates were concentrated in vacuo and purified by flash column chromatograph (Biotage Flash 40M) eluted with EtOAc:hexane (1:1) to give the second batch of product (total 3.1 g, 89%). $^1$H NMR (400 MHz, CD$_3$OD) δ ppm 7.34 (s, 1H), 7.52 (t, J=7.58 Hz, 1H), 7.77 (t, J=7.46 Hz, 1H), 7.90 (d, J=8.07 Hz, 1H), 8.39 (d, J=8.07 Hz, 1H), 11.37 (s, 1H); MS 180 (M+H)$^+$.

Step 3:

A solution of 4-chloro-2H-isoquinolin-1-one (Product of Step 2, 3.1 g, 17 mmol) in POCl$_3$ (20 mL) was refluxed for 4 h. After cooling and concentration, the residue was extracted with CHCl$_3$ (50 ml) and neutralized with 1N NaOH. The organic layer was washed with brine, dried over MgSO$_4$ and concentrated in vacuo. The crude product was purified by flash column chromatograph (Biotage Flash 40M) eluted with 5% EtOAc in hexane to give the product (2.3 g, 66%). $^1$H NMR (400 MHz, CDCl$_3$) δ ppm 7.77 (ddd, J=8.31, 7.09, 1.22 Hz, 1H), 7.88 (ddd, J=8.31, 7.09; 1.22 Hz, 1H), 8.23 (d, J=8.31 Hz, 1H), 8.34 (s, 1H), 8.36 (d, J=8.56 Hz, 1H); MS 198 (M+H)$^+$.

Step 4:

A solution of 1,4-dichloro-isoquinoline (Product of Step 3, 20 mg, 0.1 mmol) and 2(S)-[1 (R)-(1-ethyl-cyclopropane-sulfonylaminocarbonyl)-2(S)-vinyl-cyclopropylcarbamoyl]-N-[N-Boc-amino-(S)-t-butyl-acetyl]-4(R)-hydroxy-pyrrolidine (58 mg, 0.1 mmol) in DMF (1 ml) was cooled to −78° C. and t-BuOK (1.0 M in THF, 0.75 ml) was added. The resulting mixture was warmed to room temperature and stirred overnight. The reaction was quenched with aqueous NH$_4$Cl and extracted with EtOAc. The organic layer was washed with brine, dried over MgSO$_4$ and concentrated in vacuo. The crude product was purified by Prep HPLC to give compound 102 (29 mg, 39%). $^1$H NMR (400 MHz, CD$_3$OD) δ ppm 0.96 (m, 5H), 1.03 (s, 9H), 1.21 (s, 9H), 1.42 (m, 1H), 1.53 (m, 2H), 1.85 (m, 2H), 1.98 (m, 1H), 2.27 (m, 2H), 2.64 (dd, J=13.45, 6.85 Hz, 1H), 4.08 (m, 1H), 4.22 (s, 1H), 4.54 (m, 2H), 5.12 (d, J=10.27 Hz, 1H), 5.29 (d, J=17.12 Hz, 1H), 5.71 (m, 1H), 5.85 (s, 1H), 7.64 (t, J=7.34 Hz, 1H), 7.86 (m, 1H), 8.10 (m, 2H), 8.26 (d, J=8.07 Hz, 1H); MS 768 (M+Na)$^+$.

76

Example 103

Preparation of Compound 103

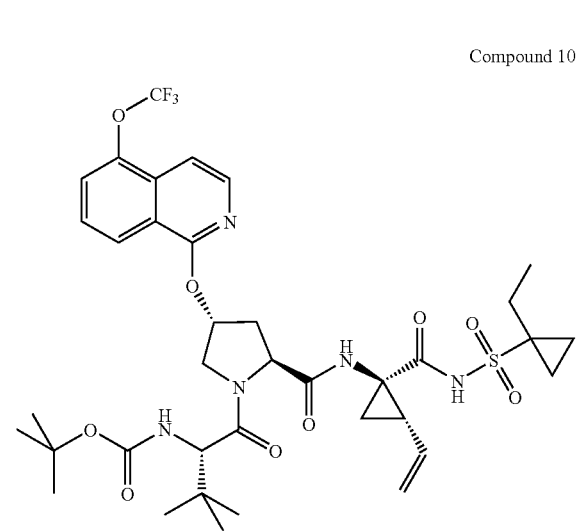

Compound 103

Compound 103 was prepared by following Steps 1 through 4 described in Example 102 except that the following modifications were made:

Step 1–2:

2-Trifluormethoxycinnamic acid (11.6 g) was used as starting material and 5.1 g (44%) of product was obtained.

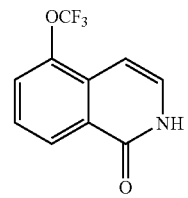

$^1$H NMR (400 MHz, CD$_3$OD) δ ppm 6.79 (d, J=7.3 Hz, 1H), 7.29 (d, J=7.3 Hz, 1H), 7.57 (t, J=8.1 Hz, 1H), 7.70 (d, J=7.8 Hz, 1H), 8.30 (d, J=8.1 Hz, 1H)., MS 230 (M+H)$^+$.

Step 3:

5-trifluoromethoxy-2H-isoquinolin-1-one (Product of Step 2, 4.58 g) was used as starting material and 4.35 g (88%) of product was obtained.

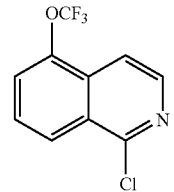

$^1$H NMR (400 MHz, CDCl$_3$) δ ppm 7.66 (m, 2H), 7.87 (d, J=5.9 Hz, 1H), 8.31 (m, 1H), 8.37 (d, J=5.9 Hz, 1H); MS 248 (M+H)$^+$.

Step 4:

1-Chloro-5-trifluoromethoxy-isoquinoline (Product of Step 3, 25 mg) was used as starting material and 28 mg (35%) of compound 103 was obtained. ¹H NMR (400 MHz, CD₃OD) δ ppm 0.96 (m, 5H), 1.04 (s, 9H), 1.19 (s, 9H), 1.42 (m, 1H), 1.52 (m, 2H), 1.85 (m, 2H), 1.97 (m, 1H), 2.28 (m, 2H), 2.65 (dd, J=13.69, 7.09 Hz, 1H), 4.07 (dd, J=11.98, 2.69 Hz, 1H), 4.21 (s, 1H), 4.56 (m, 2H), 5.12 (d, J=10.27 Hz, 1H), 5.29 (d, J=17.12 Hz, 1H), 5.71 (m, 1H), 5.89 (s, 1H), 7.49 (d, J=5.87 Hz, 1H), 7.58 (t, J=8.07 Hz, 1H), 7.69 (d, J=7.34 Hz, 1H), 8.12 (d, J=6.11 Hz, 1H), 8.22 (d, J=8.31 Hz, 1H); MS 818 (M+Na)⁺.

Example 104

Preparation of Compound 104

Compound 104

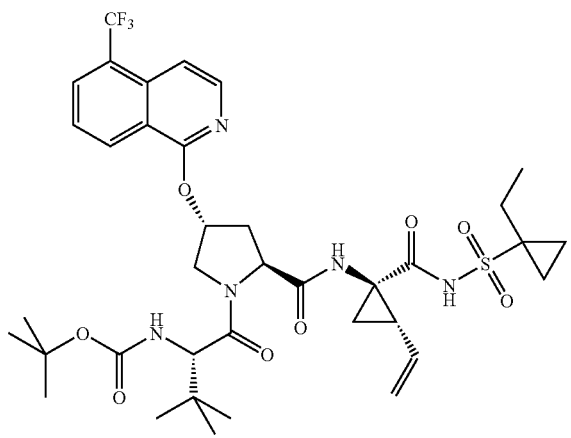

Compound 104 was prepared by following Steps 1 through 4 described in Example 102 except that the following modifications were made:

Step 1–2:

2-Trifluormethylcinnamic acid (10.0 g) was used as starting material and 5.0 g (50%) of product was obtained.

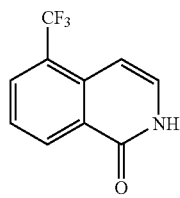

¹H NMR (400 MHz, CD₃OD) δ ppm 6.83 (m, 1H), 7.33 (d, J=7.58 Hz, 1H), 7.63 (t, J=7.83 Hz, 1H), 8.09 (d, J=7.58 Hz, 1H), 8.57 (d, J=8.07 Hz, 1H).

Step 3:

5-Trifluoromethyl-2H-isoquinolin-1-one (Product of Step 2, 4.4 g) was used and 3.5 g (73%) of product was obtained.

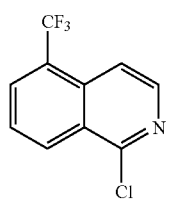

¹H NMR (400 MHz, CDCl₃) δ ppm 7.75 (t, J=7.95 Hz, 1H), 7.90 (m, 1H), 8.12 (d, J=7.34 Hz, 1H), 8.41 (d, J=6.11 Hz, 1H), 8.60 (d, J=8.56 Hz, 1H).

Step 4:

1-Chloro-5-trifluoromethyl-isoquinoline (Product of Step 3, 23 mg) was used as starting material and 24 mg (31%) of compound 104 was obtained. ¹H NMR (400 MHz, CD₃OD) δ ppm 0.96 (m, 5H), 1.03 (s, 9H), 1.17 (s, 9H), 1.47 (m, 3H), 1.92 (m, 3H), 2.29 (m, 2H), 2.66 (dd, J=13.08, 7.21 Hz, 1H), 4.07 (d, J=11.00 Hz, 1H), 4.20 (s, 1H), 4.57 (m, 2H), 5.12 (d, J=10.27 Hz, 1H), 5.28 (d, J=16.87 Hz, 1H), 5.71 (m, 1H), 5.90 (s, 1H), 7.54 (s, 1H), 7.65 (m, 1H), 8.15 (m, 2H), 8.51 (d, J=7.83 Hz, 1H); MS 802 (M+Na)⁺.

Example 105

Preparation of Compound 105

Compound 105

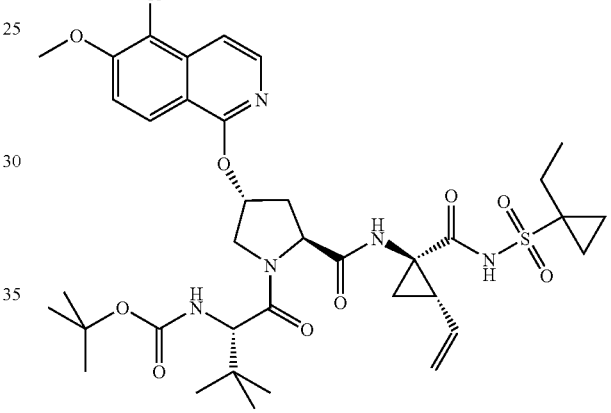

Compound 105 was prepared by following Steps 1 through 4 described in Example 102 except that the following modifications were made:

Step 1–2:

2-Chloro-3-methoxycinnamic acid (658 mg) was used as starting material and 360 mg (54%) of product was obtained.

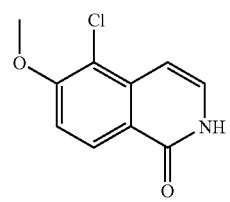

¹H NMR (400 MHz, CD₃OD) δ ppm 4.02 (s, 3H), 6.91 (d, J=7.34 Hz, 1H), 7.23 (d, J=7.58 Hz, 1H), 7.35 (d, J=9.05 Hz, 1H), 8.27 (d, J=9.05 Hz, 1H).

Step 3:

5-Chloro-6-methoxy-2H-isoquinolin-1-one (Product of Step 2, 350 mg) was used and 300 mg (80%) of product was obtained.

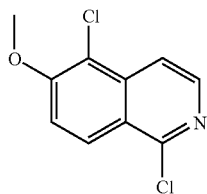

¹H NMR (400 Hz, CDCl₃) δ ppm 4.09 (s, 3H), 7.43 (d, J=9.29 Hz, 1H), 7.93 (d, J=6.11 Hz, 1H), 8.30 (m, 2H); MS 229 (M+H)⁺.

Step 4:

1,5-Dichloro-6-methoxy-isoquinoline (Product of Step 3, 23 mg) was used as starting material and 19 mg (25%) of compound 105 was obtained. ¹H NMR (400 MHz, CD₃OD) δ ppm 0.97 (m, 5H), 1.03 (s, 9H), 1.21 (s, 9H), 1.43 (m, 1H), 1.52 (m, 2H), 1.85 (m, 2H), 1.96 (m, 1H), 2.27 (m, 2H), 2.63 (dd, J=13.21, 6.85 Hz, 1H), 4.06 (m, 4H), 4.21 (s, 1H), 4.47 (d, J=11.25 Hz, 1H), 4.57 (m, 1H), 5.12 (d, J=10.52 Hz, 1H), 5.29 (d, J=16.87 Hz, 1H), 5.71 (m, 1H), 5.85 (s, 1H), 7.40 (d, J=8.80 Hz, 1H), 7.55 (d, J=5.62 Hz, 1H), 8.01 (d, J=6.11 Hz, 1H), 8.21 (d, J=8.80 Hz, 1H); MS 776 (M+H)⁺.

Example 106

Preparation of Compound 106

Compound 106

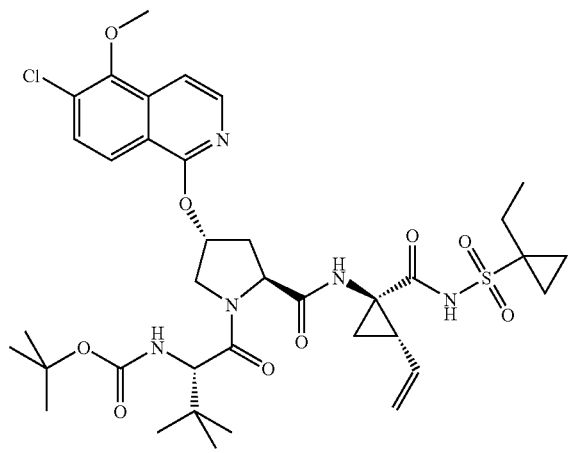

Compound 106 was prepared by following Steps 1 through 4 described in Example 102 except that the following modifications were made:

Step 1–2:

3-Chloro-2-methoxycinnamic acid (4.24 g) was used as starting material and 2.4 g (57%) of product was obtained.

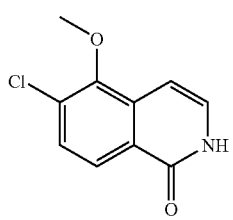

¹H NMR (400 MHz, CD₃OD) δ ppm 3.93 (s, 1H), 6.85 (d, J=7.34 Hz, 1H), 7.24 (d, J=7.34 Hz, 1H), 7.52 (d, J=8.80 Hz, 1H), 8.03 (d, J=8.80 Hz, 1H); MS 210 (M+H)⁺.

Step 3:

6-Chloro-5-methoxy-2H-isoquinolin-1-one (Product of Step 2, 2.1 g) was used and 1.9 g (83%) of product was obtained.

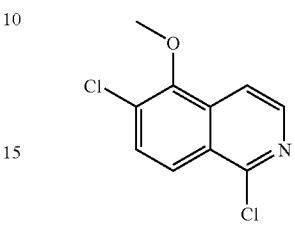

¹H NMR (400 Hz, CDCl₃) δ ppm 4.03 (s, 2H), 7.63 (d, J=9.05 Hz, 1H), 7.86 (d, J=5.14 Hz, 1H), 8.06 (d, J=9.05 Hz, 1H), 8.32 (d, J=5.62 Hz, 1H); MS 229 (M+H)⁺.

Step 4:

1,6-Dichloro-5-methoxy-isoquinoline (Product of Step 3, 23 mg) was used as starting material and 28 mg (36%) of compound 106 was obtained. ¹H NMR (400 MHz, CD₃OD) δ ppm 0.96 (m, 5H), 1.03 (s, 9H), 1.21 (s, 9H), 1.42 (m, 1H), 1.52 (m, 2H), 1.85 (m, 2H), 1.96 (m, 1H), 2.27 (m, 2H), 2.63 (dd, J=13.69, 7.09 Hz, 1H), 3.98 (s, 3H), 4.05 (dd, J=12.47, 2.20 Hz, 1H), 4.20 (s, 1H), 4.47 (d, J=11.74 Hz, 1H), 4.56 (dd, J=9.90, 7.46 Hz, 1H), 5.12 (d, J=10.27 Hz, 1H), 5.29 (d, J=16.87 Hz, 1H), 5.71 (m, 1H), 5.86 (s, 1H), 7.48 (d, J=8.80 Hz, 1H), 7.52 (d, J=6.11 Hz, 1H), 7.96 (d, J=9.05 Hz, 1H), 8.06 (d, J=6.11 Hz, 1H); MS 776 (M+H)⁺.

Example 107

Preparation of Compound 107

Compound 107

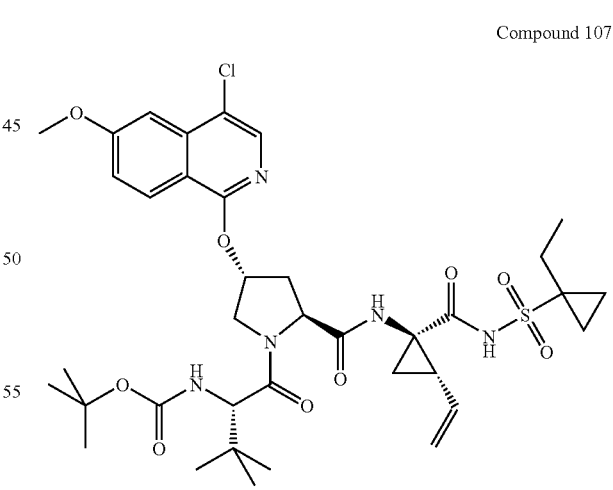

Compound 107 was prepared by following Steps 1 through 4 described in Example 102 except that the following modifications were made:

Step 1–2:

A mixture of 6-methoxy-2H-isoquinolin-1-one (700 mg) and NCS (532 mg) in MeCN (10 ml) was refluxed for 3 h. Filtration gave 600 mg (72%) of the desired product.

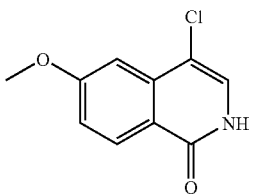

¹H NMR (400 MHz, CD₃OD) δ ppm 3.96 (s, 1H), 7.19 (dd, J=8.80, 2.45 Hz, 1H), 7.28 (d, J=2.45 Hz, 1H), 7.34 (s, 1H), 8.25 (d, J=9.05 Hz, 1H); MS 210 (M+H)⁺.

Step 3:
4-Chloro-6-methoxy-2H-isoquinolin-1-one (Product of Step 2, 500 mg) was used as starting material and 400 mg of product was obtained.

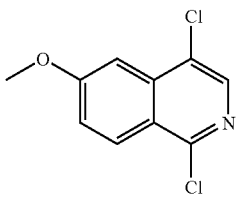

¹H NMR (400 Hz, CDCl₃) δ ppm 4.01 (s, 3H), 7.35 (d, J=2.45 Hz, 1H), 7.41 (d, J=2.45 Hz, 1H), 8.24 (d, J=9.29 Hz, 1H), 8.27 (s, 1H); MS 229 (M+H)⁺.

Step 4:
1,4-Dichloro-6-methoxy-isoquinoline (Product of Step 3, 42 mg) was used as starting material and 70 mg (45%) of compound 107 was obtained. ¹H NMR (400 MHz, CD₃OD) δ ppm 0.95 (m, 14H), 1.23 (s, 9H), 1.47 (m, 3H), 1.88 (m, 3H), 2.24 (m, 2H), 2.62 (m, J=13.69, 7.09 Hz, 1H), 3.97 (s, 3H), 4.04 (m, J=8.80 Hz, 1H), 4.22 (m, 1H), 4.52 (m, 2H), 5.12 (d, J=10.27 Hz, 1H), 5.28 (d, J=16.87 Hz, 1H), 5.71 (m, 1H), 5.81 (s, 1H), 7.19 (dd, J=9.05, 2.20 Hz, 1H), 7.38 (d, J=1.96 Hz, 1H), 8.00 (s, 1H), 8.15 (d, J=9.05 Hz, 1H); MS 776 (M+H)⁺.

Example 108

Preparation of Compound 108

Compound 108

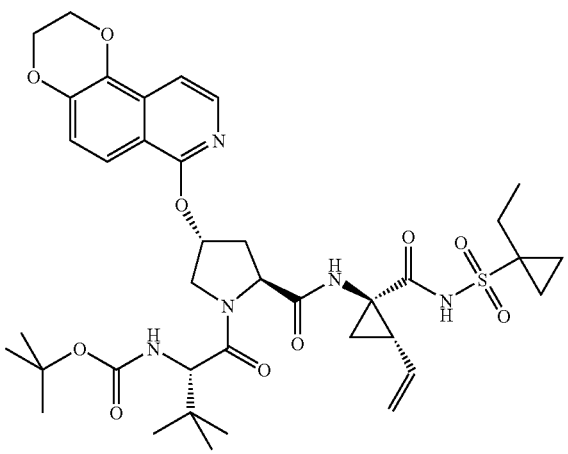

Compound 108 was prepared by following Steps 1 through 4 described in Example 102 except that the following modifications were made:

Step 1–2:
3-(2,3-Dihydro-benzo[1,4]dioxin-5-yl)-acrylic acid (4.12 g) was used as starting material and 2.2 g (53%) of product was obtained.

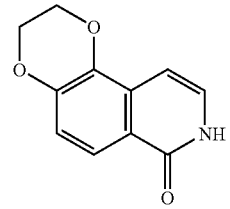

¹H NMR (400 MHz, CD₃OD) δ ppm 4.37 (m, 4H), 6.83 (d, J=7.09 Hz, 1H), 7.02 (d, J=8.80 Hz, 1H), 7.12 (d, J=7.34 Hz, 1H), 7.79 (d, J=8.80 Hz, 1H); MS 204 (M+H)⁺.

Step 3:
2,3-Dihydro-7H-1,4-dioxa-7-aza-phenanthren-8-one (Product of Step 2, 2.05 g) was used as starting material and 1.5 g (68%) of product was obtained.

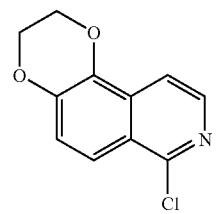

¹H NMR (400 Hz, CDCl₃) δ ppm 4.42 (m, 4H), 7.24 (d, J=9.05 Hz, 1H), 7.77 (d, J=5.87 Hz, 1H), 7.84 (d, J=9.05 Hz, 1H), 8.18 (d, J=5.87 Hz, 1H); MS 222 (M+H)⁺.

Step 4:
8-Chloro-2,3-dihydro-1,4-dioxa-7-aza-phenanthrene (Product of Step 3, 22 mg) was used as starting material and 29 mg (38%) of compound 108 was obtained. ¹H NMR (400 MHz, CD₃OD) δ ppm 0.96 (m, 5H) 1.04 (s, 9H) 1.25 (s, 9H) 1.48 (m, 3H) 1.84 (m, 2H) 1.96 (m, 1H) 2.25 (m, 2H) 2.63 (dd, J=13.69, 7.83 Hz, 1H) 4.06 (m, 1H) 4.22 (s, 1H) 4.43 (m, 5H) 4.54 (dd, J=10.03, 7.83 Hz, 1H) 5.12 (d, J=10.03 Hz, 1H) 5.28 (d, J=17.12 Hz, 1H) 5.71 (m, 1H) 5.82 (s, 1H) 7.07 (d, J=8.80 Hz, 1H) 7.48 (d, J=5.87 Hz, 1H) 7.74 (d, J=9.29 Hz, 1H) 7.89 (d, J=6.36 Hz, 1H); MS 770 (M+H)⁺.

Example 109 and 110

Preparation of Compound 109 and 110

Compound 109

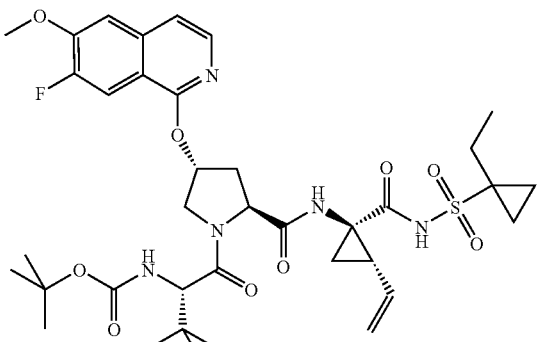

Compound 110

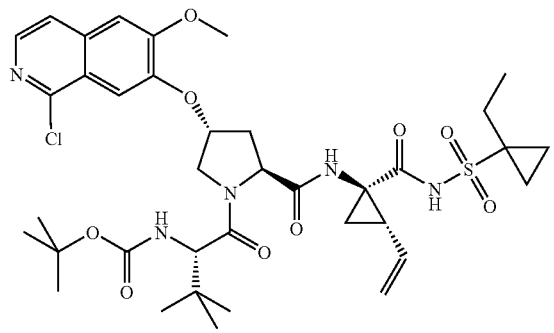

Compound 109 and compound 110 were prepared by following Steps 1 through 4 described in Example 102 except that the following modifications were made:

Step 1–2:
4-Fluoro-3-methoxycinnamic acid (19.6 g) was used as starting material and 9.5 g (48%) of product was obtained.

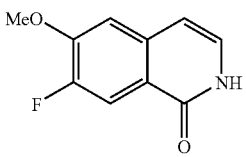

$^1$H NMR (400 MHz, CD$_3$COCD$_3$) δ ppm 4.00 (s, 1H), 6.49 (d, J=7.34 Hz, 1H), 7.19 (d, J=7.09 Hz, 1H), 7.29 (d, J=8.07 Hz, 1H), 7.86 (d, J=11.74 Hz, 1H).

Step 3:
7-Fluoro-6-methoxy-2H-isoquinolin-1-one (Product of Step 2, 9.0 g) was used as starting material and 7.0 g (70%) of product was obtained.

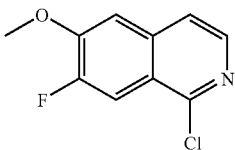

$^1$H NMR (400 MHz, CDCl$_3$) δ ppm 4.04 (s, 3H), 7.17 (d, J=8.07 Hz, 1H), 7.48 (d, J=5.62 Hz, 1H), 7.94 (d, J=11.49 Hz, 1H), 8.20 (d, J=5.62 Hz, 1H).

Step 4:
1-Chloro-7-fluoro-6-methoxy-isoquinoline (Product of step 3, 21 mg) was used as starting material and 9 mg (12%) of compound 109 and 24 mg (32%) of compound 110 were obtained.

Compound 109 $^1$H NMR (400 MHz, CD$_3$OD) δ ppm 1.00 (m, 14H), 1.25 (s, 9H), 1.47 (m, 3H), 1.84 (m, 2H), 1.97 (m, 1H), 2.25 (m, 2H), 2.61 (dd, J=13.82, 6.97 Hz, 1H), 4.00 (s, 3H), 4.04 (dd, J=11.37, 3.55 Hz, 1H), 4.22 (s, 1H), 4.44 (d, J=11.98 Hz, 1H), 4.55 (m, 1H), 5.12 (d, J=110.03 Hz, 1H), 5.28 (d, J=17.36 Hz, 1H), 5.71 (m, 1H), 5.83 (s, 1H), 7.28 (d, J=5.62 Hz, 1H), 7.37 (d, J=8.07 Hz, 1H), 7.76 (d, J=11.49 Hz, 1H), 7.91 (d, J=5.87 Hz, 1H); MS 760 (M+H)$^+$.

Compound 110 $^1$H NMR (400 MHz, Methanol-D4) δ ppm 0.95 (m, 5H), 1.02 (s, 9H), 1.30 (s, 9H), 1.51 (m, 3H), 1.84 (m, 2H), 1.97 (td, J=14.92, 7.34 Hz, 1H), 2.26 (m, 2H), 2.58 (dd, J=13.45, 6.60 Hz, 1H), 3.99 (s, 3H), 4.09 (dd, J=11.86, 2.81 Hz, 1H), 4.23 (s, 1H), 4.32 (d, J=11.74 Hz, 1H), 4.53 (dd, J=10.15, 6.72 Hz, 1H), 5.12 (d, J=10.39, 1.34 Hz, 1H), 5.29 (dd, J=17.12, 1.22 Hz, 1H), 5.39 (s, 1H), 5.72 (m, 1H), 7.43 (s, 1H), 7.64 (s, 1H), 7.72 (d, J=5.62 Hz, 1H), 8.10 (d, J=5.87 Hz, 1H); MS 776 (M+H)$^+$.

Example 111

Preparation of Compound 111

Compound 111

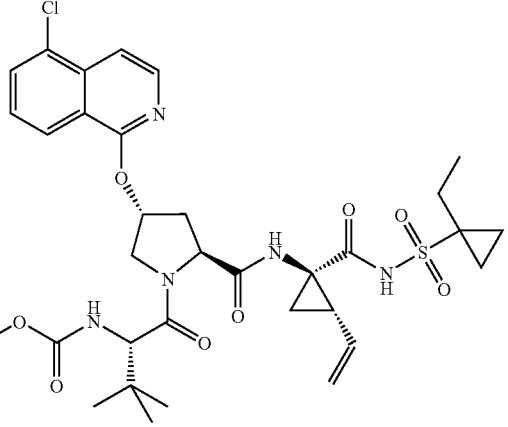

Compound 111 was prepared by following Steps 1 through 5 described in Example 100 except that, in step 5,1,5-dichloro-isoquinoline (20 mg) and (1(S)-{2(S)-[1(R)-(1-ethyl-cyclopropanesulfonylaminocarbonyl)-2(S)-vinyl-cyclopropylcarbamoyl]-4-hydroxy-pyrrolidine-1-carbonyl}-2,2-dimethyl-propyl)-carbamic acid isopropyl ester (57 mg) were used as starting materials and 20 mg (27%) of compound 111 was obtained. $^1$H NMR (400 MHz, CD$_3$OD) δ ppm 0.97 (m, 5H), 1.04 (s, 9H), 1.11 (d, J=6.11 Hz, 3H), 1.28 (s, 3H), 1.41 (m, 1H), 1.50 (m, 2H), 1.84 (m, 2H), 1.96 (m, 1H), 2.26 (m, 2H), 2.65 (dd, J=13.69, 7.09 Hz, 1H), 4.08 (dd, J=11.86, 3.55 Hz, 1H), 4.27 (s, 1H), 4.45 (m, 2H), 4.57 (dd, J=10.03, 7.34 Hz, 1H), 5.11 (d, J=10.27 Hz, 1H), 5.28 (d, J=17.12 Hz, 1H), 5.72 (m, 1H), 5.88 (s, 1H); 7.49 (t, J=7.95 Hz, 1H), 7.63 (d, J=6.11 Hz, 1H), 7.82 (d, J=7.34 Hz, 1H), 8.11 (d, J=6.11 Hz, 1H), 8.19 (d, J=8.56 Hz, 1H); MS 732 (M+H)$^+$.

Example 112

Preparation of Compound 112

Compound 112

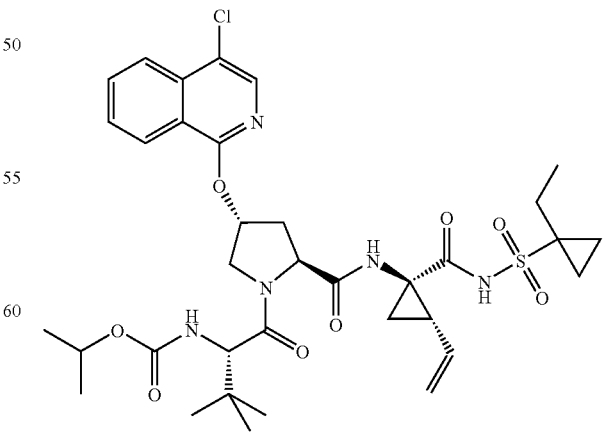

Compound 112 was prepared by following Steps 1 through 4 described in Example 102 except that, in step 4, (1(S)-{2(S)-[1(R)-(1-ethyl-cyclopropanesulfonylamino-carbonyl)-2(S)-vinyl-cyclopropylcarbamoyl]-4-hydroxy-pyrrolidine-1-carbonyl}-2,2-dimethyl-propyl)-carbamic acid isopropyl ester (57 mg) was used as starting material and 14 mg (19%) of compound 112 was obtained. $^1$H NMR (400 MHz, CD$_3$OD) δ ppm 0.96 (m, 5H), 1.04 (s, 9H), 1.09 (d, J=6.36 Hz, 3H), 1.27 (s, 3H), 1.39 (dd, J=9.54, 5.38 Hz, 1H), 1.50 (m, 2H), 1.83 (m, 2H), 1.95 (m, 1H), 2.26 (m, 2H), 2.63 (dd, J=13.82, 6.97 Hz, 1H), 4.05 (dd, J=11.74, 3.67 Hz, 1H), 4.26 (m, 1H), 4.43 (m, 2H), 4.56 (dd, J=10.03, 7.09 Hz, 1H), 5.10 (d, J=10.27 Hz, 1H), 5.27 (d, J=17.12 Hz, 1H), 5.69 (m, 1H), 5.84 (s, 1H), 6.87 (d, J=9.05 Hz, 1H), 7.63 (t, J=7.70 Hz, 1H), 7.85 (t, J=7.70 Hz, 1H), 8.05 (s, 1H), 8.10 (d, J=8.31 Hz, 1H), 8.25 (d, J=8.31 Hz, 1H); MS 732 (M+H)$^+$.

Example 113

Preparation of Compound 113

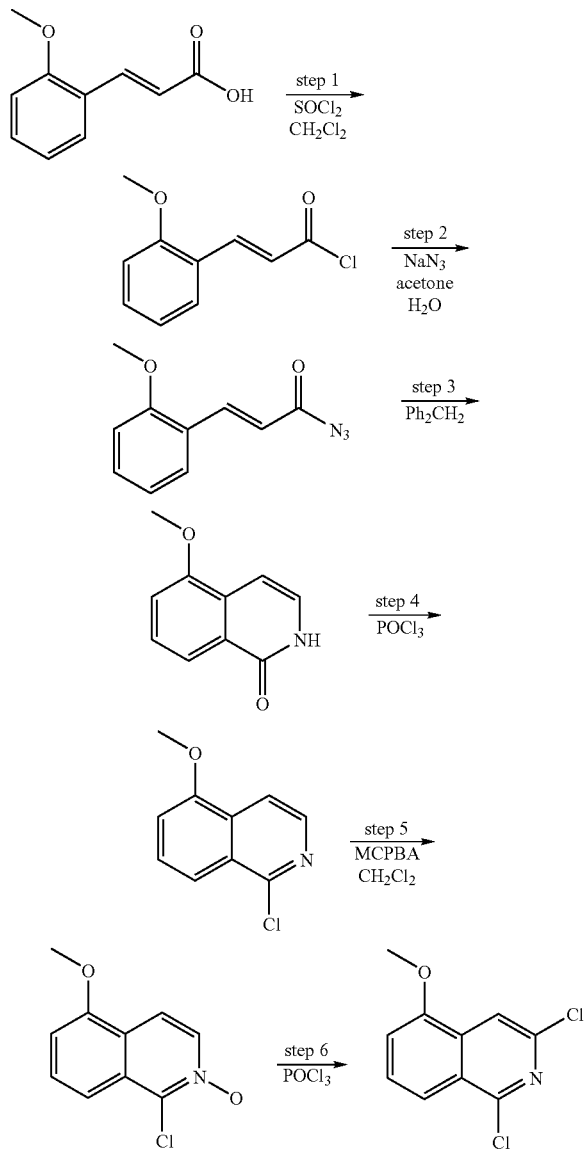

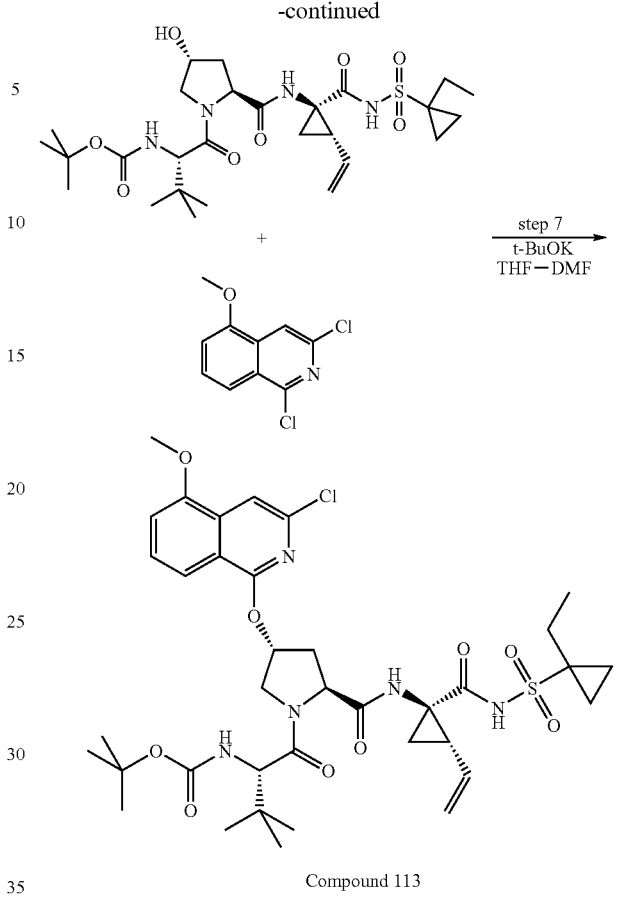

Compound 113

Step 1–4:

1-Chloro-5-methoxy-isoquinoline was prepared by the same Steps 1 through 4 described in Example 100.

Step 5:

To a cold solution of 1-chloro-5-methoxy-isoquinoline (Product of Step 4, 1.94 g, 10 mmol) in CH$_2$Cl$_2$ (30 ml) was added MCBPA (77%, 5.6 g, 25 mmol) and the resulting mixture was stirred at room temperature overnight. The reaction was quenched with 5N NaOH (5 ml). The organic layer was separated, washed with brine, dried over MgSO$_4$ and concentrated in vacuo. Purification by flash column chromatograph (Biotage Flash 40M) eluted with 5% EtOAc in hexane provided the desired product (0.5 g, 24%). MS 210 (M+H)$^+$.

Step 6:

A solution of 1-chloro-5-methoxy-isoquinoline 2-oxide (Product of Step 5, 0.5 g, 2.4 mmol) in POCl$_3$ (5 ml) was refluxed for 3 h. After cooling and concentration, the residue was extracted with CHCl$_3$ (50 ml) and neutralized with 1N NaOH. The organic layer was washed with brine, dried over MgSO$_4$ and concentrated in vacuo. The crude product was purified by flash column chromatograph (Biotage Flash 40M) eluted with 5% EtOAc in hexane to give the desired product (0.43 g, 80%). MS 228 (M+H)$^+$.

Step 7:

A solution of 1,3-dichloro-5-methoxy-isoquinoline (Product of Step 6, 23 mg, 0.1 mmol) and 2(S)-[1 (R)-(1-ethyl-cyclopropanesulfonylaminocarbonyl)-2(S)-vinyl-cyclopropylcarbamoyl]-N-[N-Boc-amino-(S)-t-butyl-acetyl]-4(R)-hydroxy-pyrrolidine (58 mg, 0.1 mmol) in DMF (1 ml) was cooled to −78° C. and t-BuOK (1.0 M in THF, 0.75 ml) was added. The resulting mixture was stirred at room temperature overnight. The reaction was quenched with aqueous NH₄Cl and extracted with EtOAc. The organic layer was washed with brine, dried over MgSO₄ and concentrated in vacuo. The crude product was purified by Prep HPLC to give compound 113 (27 mg, 35%). $^1$H NMR (400 MHz, CD₃OD) δ ppm 0.96 (m, 5H), 1.04 (s, 9H), 1.26 (s, 9H), 1.48 (m, 3H), 1.84 (m, 2H), 1.95 (m, 1H), 2.26 (m, 2H), 2.63 (dd, J=13.82, 6.97 Hz, 1H), 3.99 (s, 3H), 4.07 (m, 1H), 4.24 (s, 1H), 4.46 (d, J=11.98 Hz, 1H), 4.54 (dd, J=10.15, 7.21 Hz, 1H), 5.11 (d, J=10.52 Hz, 1H), 5.28 (d, J=17.12 Hz, 1H), 5.71 (m, 1H), 5.84 (s, 1H), 7.16 (d, J=7.58 Hz, 1H), 7.42 (t, J=8.07 Hz, 1H), 7.59 (s, 1H), 7.72 (d, J=8.31 Hz, 1H); MS 798 (M+Na)⁺.

Section C

Preparation of Compounds 200–220

Example 200

Preparation of Compound 200

Compound 200

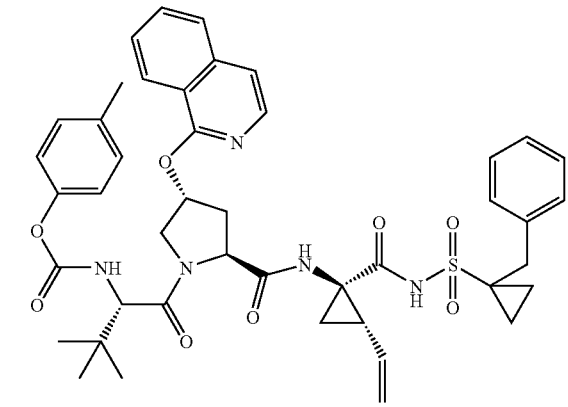

Scheme 1

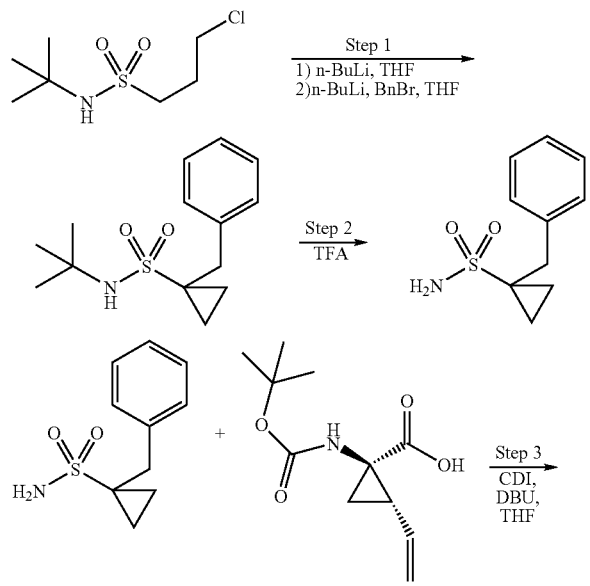

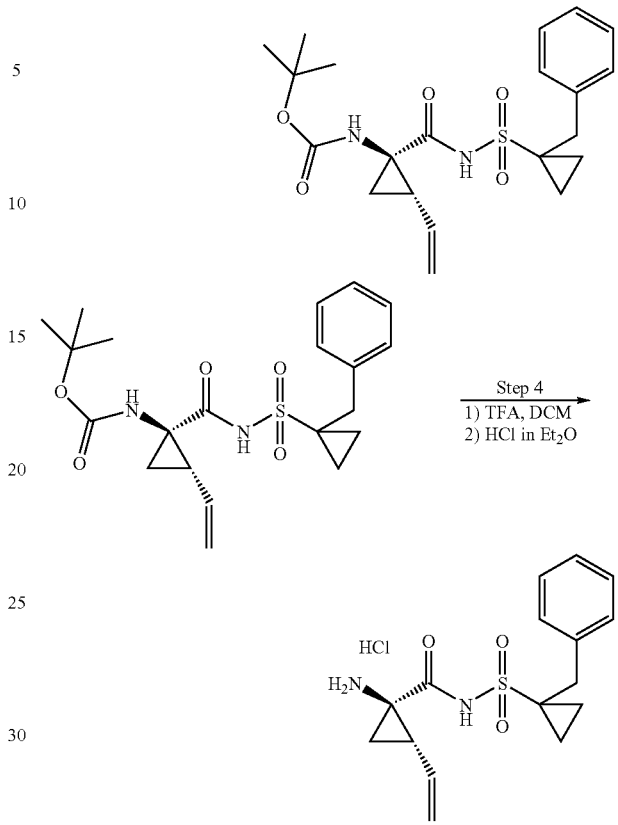

Step 1:

A solution of 3-chloro-propane-1-sulfonic acid tert-butylamide (9.34 g, 43.7 mmol) was chilled to −78° C. and treated with 2.5M n-butyllithium in hexanes (36.7 mL, 92 mmol) dropwise over 20 min. The mixture was stirred for an additional 10 min and was then allowed to warm to rt and stirred for 1.5 h. The mixture was then recooled to −78° C. and was again treated with 2.5M n-butyllithium in hexanes (19.2 mL, 48 mmol) dropwise over 15 min. The mixture was allowed to warm to rt and stirred for 2 h. The solution was again cooled to −78° C. and was treated with a solution of benzyl bromide (9.71 g, 56.8 mmol) in dry THF (10 mL) dropwise over 15 min. The mixture was then stirred at rt for 18 h. Saturated aqueous ammonium chloride (50 mL) was added, and the mixture was concentrated in vacuo. To the residue was added ethyl acetate (300 mL) and water (100 mL). The resulting bilayer was shaken and the two phases were separated. The organic phase was washed with water (2×100 mL) and brine (50 mL). The combined aqueous washes were back-extracted with ethyl acetate (150 mL), and the combined organics were dried over magnesium sulfate, filtered and concentrated in vacuo to give a waxy brown oil. Purification of the crude product by silica gel chromatography (10% ethyl acetate in hexanes) gave the desired product as a white powder (7.75 g, 66.4% yield): $^1$H NMR (CDCl₃) δ 0.72–0.74 (m, 2H), 1.26 (s, 9H), 1.34–1.36 (m, 2H), 3.26 (s, 2H), 3.69 (s, 1H), 7.19 (d, J=6.71 Hz, 2H), 7.23–7.26 (m, 1H), 7.29–7.31 (m, 2H); MS m/z 290 ((M+Na)+).

Step 2:

The product from Example 200, Step 1 (7.70 g, 28.8 mmol) was dissolved in TFA (75 mL) and the mixture was stirred for 1 h. The mixture was then concentrated in vacuo to give 6.19 g (quantitative yield) of the desired product as a white solid. This material was used in the next step without further purification: ¹H NMR (CD₃OD) δ 0.58–0.66 (m, 2H), 1.16–1.25 (m, 2H), 3.33 (s, 2H), 7.14–7.34 (m, 5H); MS m/z 212 (MH+).

Step 3:

A solution of 1(R)-tert-butoxycarbonylamino-2(S)-vinyl-cyclopropanecarboxylic acid (4.45 g, 19.6 mmol) and 1,1'-carbonyldiimidazole (3.97 g, 24.5 mmol) in dry THF (60 mL) was heated to boiling under reflux for 90 min. Upon cooling to rt, the mixture was treated sequentially with the product from Example 200, Step 2 (5.17 g, 24.5 mmol) and 1,8-diazabicyclo[5.4.0]undec-7-ene (6.26 g, 41.1 mmol). The resulting mixture was stirred at rt for 72 h, and was then concentrated in vacuo to a viscous brown oil. The residue was dissolved in ethyl acetate (300 mL) and was washed with 1N HCl (3×75 mL) and then with brine (75 mL). The organic was dried over anhydrous magnesium sulfate, filtered, and concentrated. Purification by flash silica gel chromatography (DCM, then 1% MeOH in DCM) gave 8.4 g (quantitative yield) of the desired product as an off-white solid: MS m/z 443 ((M+Na)+).

Step 4:

The product from Example 200, Step 3 (8.4 g, 19.6 mmol) was dissolved in a mixture of TFA (75 mL) and DCM (75 mL) and the resulting solution was stirred for 2.5 h at rt. Concentration in vacuo to an oily residue, followed by addition of 1N HCl in Et₂O (35 mL) gave a white solid which was isolated by filtration and dried in vacuo to give 6.30 g (90.2% yield) of the desired product as an off-white powder: ¹H NMR (CD₃OD) δ 0.66–0.83 (m, 2H), 1.41–1.50 (m, 1H), 1.60 (ddd, J=10.89, 6.31, 4.76 Hz, 1H), 1.71 (dd, J=10.06, 7.87 Hz, 1H), 2.17 (t, J=7.87 Hz, 1H), 2.35–2.47 (m, 1H), 3.33 (s, 2H), 5.37 (d, J=10.25 Hz, 1H), 5.48 (d, J=17.20 Hz, 1H), 5.78 (ddd, J=17.11, 10.15, 7.50 Hz, 1H), 7.13–7.20 (m, 2H), 7.24–7.35 (m, 3H); MS m/z 321 (MH+), 343 ((M+Na)+).

Scheme 2

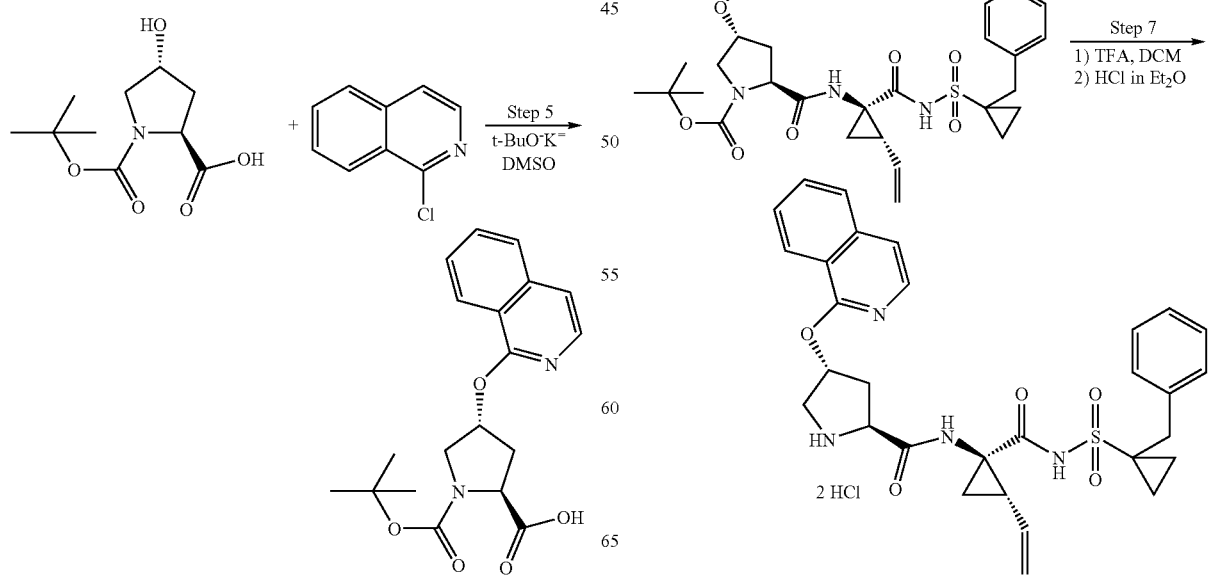

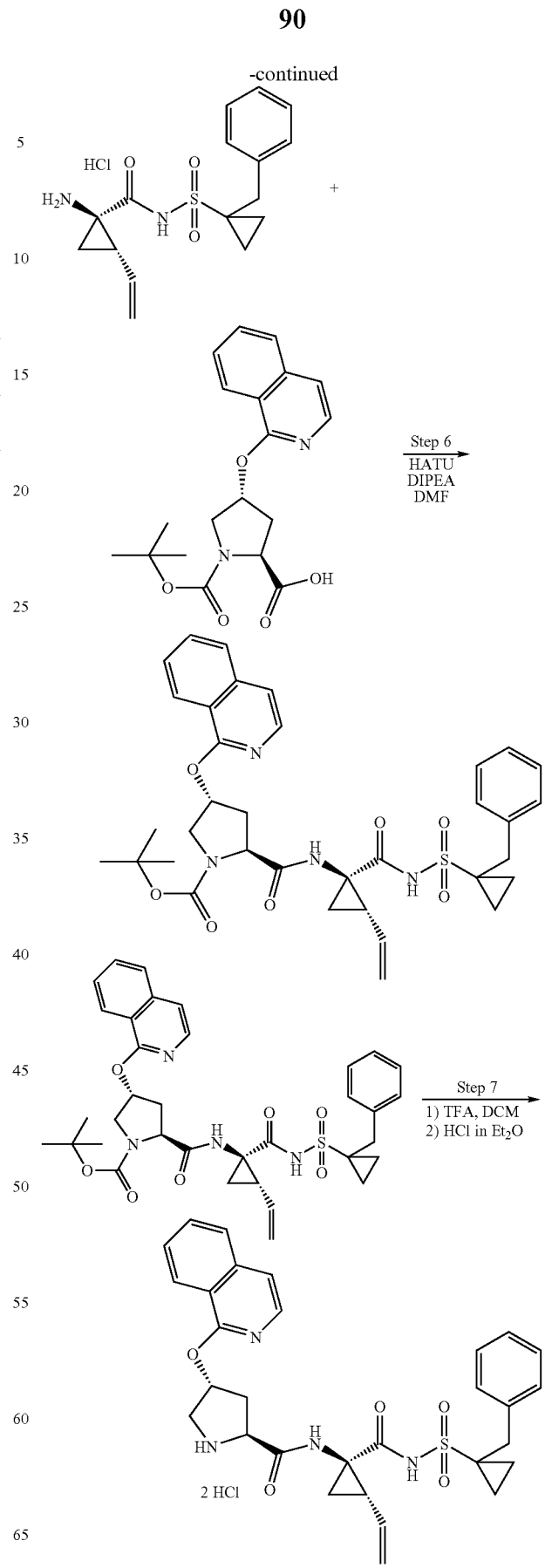

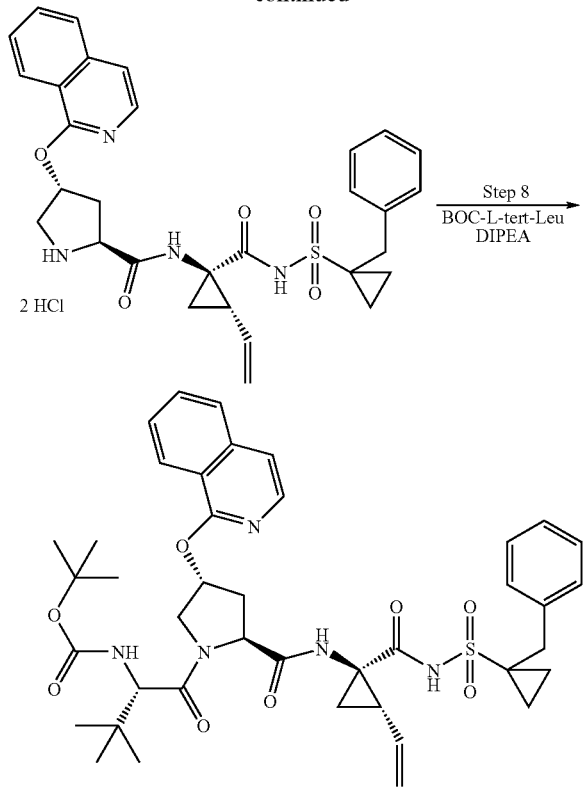

Step 5:

A stirred solution of Boc-L-4-hydroxyproline (12.3 g, 53.3 mmol) in DMSO (200 mL) was treated with solid potassium tert-butoxide (15.7 g, 133 mmol), and the resulting mixture was stirred for 100 min at rt. The reaction flask was lowered into a cool water bath and to the mixture was added solid 1-chloroisoquinoline (10.0 g, 58.1 mmol) in two batches over 30 min. The now deep red mixture was stirred for 3 h. The mixture was concentrated in vacuo to a brown residue and to it was added water (700 mL). The aqueous solution was washed successively with diethyl ether (3×250 mL) and then with ethyl acetate (2×200 mL). The aqueous solution was acidified with 1N aqueous HCl to pH=4, then the mixture was extracted with DCM (3×150 mL). The combined DCM extracts were dried over anhydrous magnesium sulfate, filtered, and concentrated in vacuo to give 16.48 g (86% yield) of a slightly orange solid which was approximately 94% pure; the major impurity appeared to be 1-hydroxyisoquinoline: $^1$H NMR (CD$_3$OD) δ 1.38–1.50 (m, 9H), 2.01 (s, 0.3H), 2.41–2.47 (m, 1H), 2.65 (s, 0.7H), 2.70–2.75 (m, 1H), 3.80–3.84 (m, 1H), 3.87 (d, J=4.58 Hz, 0.7H), 3.89 (d, J=4.58 Hz, 0.3H), 4.48 (t, J=7.93 Hz, 0.7H), 4.52 (t, J=7.93 Hz, 0.3H), 5.77–5.79 (m, 1H), 7.32–7.34 (m, 1H), 7.58 (t, J=7.48 Hz, 1H), 7.71 (t, J=7.63 Hz, 1H), 7.81 (d, J=7.94 Hz, 1H), 7.95 (d, J=6.10 Hz, 1H), 8.17–8.20 (m, 1H); MS m/z 359 (MH+), 739 ((2M+Na)+).

Step 6:

The product of Example 200, Step 4 (3.00 g, 8.41 mmol) was combined with the product of Example 200, Step 5 (3.21 g, 8.41 mmol), HATU (3.84 g, 10.1 mmol), DIPEA (3.26 g, 25.2 mmol) and DMF (75 mL) and the resulting solution was stirred at rt for 4.5 h. The mixture was concentrated in vacuo to a residue and was then redissolved in ethyl acetate (250 mL) and washed successively with pH=4 buffer (4×150 mL), water (100 mL) and brine (150 mL). The organic was dried over anhydrous magnesium sulfate, filtered and concentrated in vacuo. Purification by flash silica gel chromatography (40:1 DCM:MeOH), gave the product as 4.84 g (87.1% yield) of a beige foam solid: $^1$H NMR (CD$_3$OD) δ 0.58–0.65 (m, 2H), 1.41 (s, 9H), 1.43–1.46 (m, 2H), 1.50–1.53 (m, 1H), 1.91 (dd, J=8.09, 5.34 Hz, 1H), 2.26–2.35 (m, 2H), 2.58 (dd, J=13.73, 6.71 Hz, 1H), 3.33 (d, J=7.02 Hz, 2H), 3.82 (d, J=12.51 Hz, 1H), 3.87–3.90 (m, 1H), 4.45 (dd, J=9.61, 7.17 Hz, 1H), 5.17 (d, J=10.38 Hz, 1H), 5.36 (d, J=17.09 Hz, 1H), 5.77–5.84 (m, 2H), 7.16 (d, J=7.02 Hz, 2H), 7.22–7.25 (m, 1H), 7.27–7.30 (m, 2H), 7.32 (d, J=5.80 Hz, 1H), 7.58 (t, J=7.48 Hz, 1H), 7.71 (t, J=7.48 Hz, 1H), 7.81 (d, J=8.24 Hz, 1H), 7.95 (d, J=6.10 Hz, 1H), 8.18 (d, J=8.55 Hz, 1H); MS m/z 661 (MH+).

Step 7:

The product of Example 200, Step 6 (4.00 g, 6.05 mmol) was dissolved in 1,4-dioxane (50 mL) and the solution was treated with 4.0M HCl in 1,4-dioxane (15 mL). The mixture was stirred overnight at rt. The mixture was concentrated in vacuo and the resulting reddish-brown powder and placed under high vacuum. The yield was quantitative: $^1$H NMR (CD$_3$OD) δ 0.62–0.65 (m, 2H), 1.40–1.44 (m, 2H), 1.48–1.53 (m, 1H), 2.00 (dd, J=8.05, 5.49 Hz, 1H), 2.37–2.51 (m, 2H), 3.00 (dd, J=14.09, 7.50 Hz, 1H), 3.30 (d, J=1.83 Hz, 2H), 3.86–3.89 (m, 2H), 4.80 (dd, J=10.61, 7.32 Hz, 1H), 5.22 (dd, J=10.25, 1.46 Hz, 1H), 5.40 (dd, J=17.20, 1.46 Hz, 1H), 5.71 (ddd, J=17.11, 10.15, 8.60 Hz, 1H), 6.00 (t, J=3.29 Hz, 1H), 7.14 (d, J=1.46 Hz, 1H), 7.16 (d, J=1.83 Hz, 1H), 7.24–7.33 (m, 3H), 7.49 (d, J=6.22 Hz, 1H), 7.66–7.72 (m, 1H), 7.80–7.85 (m, 1H), 7.90–7.92 (m, 1H), 7.98 (d, J=6.22 Hz, 1H), 8.42 (d, J=8.42 Hz, 1H); MS m/z 561 (MH+).

Step 8:

The product of Example 200, Step 7 (1.90 g, 3.00 mmol) was combined with N-Boc-L-tert-leucine (0.763 g, 3.30 mmol), HATU (1.48 g, 3.90 mmol), DIPEA (1.55 g, 12.0 mmol) and DMF (50 mL) and the resulting solution was stirred at rt for 18 h. The mixture was concentrated in vacuo to a residue and was then redissolved in ethyl acetate (150 mL) and washed successively with pH=4 buffer (3×75 mL) and brine (50 mL). The organic was dried over anhydrous magnesium sulfate, filtered and concentrated in vacuo. Purification by flash silica gel chromatography (gradient: DCM, to 3% MeOH in DCM) gave 1.99 g (85.5% yield) of the desired product as an off-white foamy solid: $^1$H NMR (CD$_3$OD) δ 0.61–0.67 (m, 2H), 0.97 (s, 9H), 1.25 (s, 9H), 1.41–1.52 (m, 3H), 1.91–1.93 (m, 1H), 2.28–2.32 (m, 2H), 2.65 (dd, J=13.73, 7.32 Hz, 1H), 2.81 (s, 2H), 4.07 (dd, J=11.29, 3.36 Hz, 1H), 4.25 (d, J=9.16 Hz, 1H), 4.48 (d, J=11.29 Hz, 1H), 4.58 (dd, J=9.77, 7.63 Hz, 1H), 5.18 (d, J=10.07 Hz, 1H), 5.35 (d, J=17.40 Hz, 1H), 5.78 (ddd, J=17.01, 9.61, 9.38 Hz, 1H), 5.86 (s, 1H), 7.14–7.16 (m, 2H), 7.24–7.26 (m, 1H), 7.28–7.33 (m, 3H), 7.52 (t, J=7.63 Hz, 1H), 7.70 (t, J=7.48 Hz, 1H), 7.80 (d, J=7.93 Hz, 1H), 7.95–7.97 (m, 1H), 8.21 (d, J=8.55 Hz, 1H); MS m/z 774 (MH+).

Scheme 3

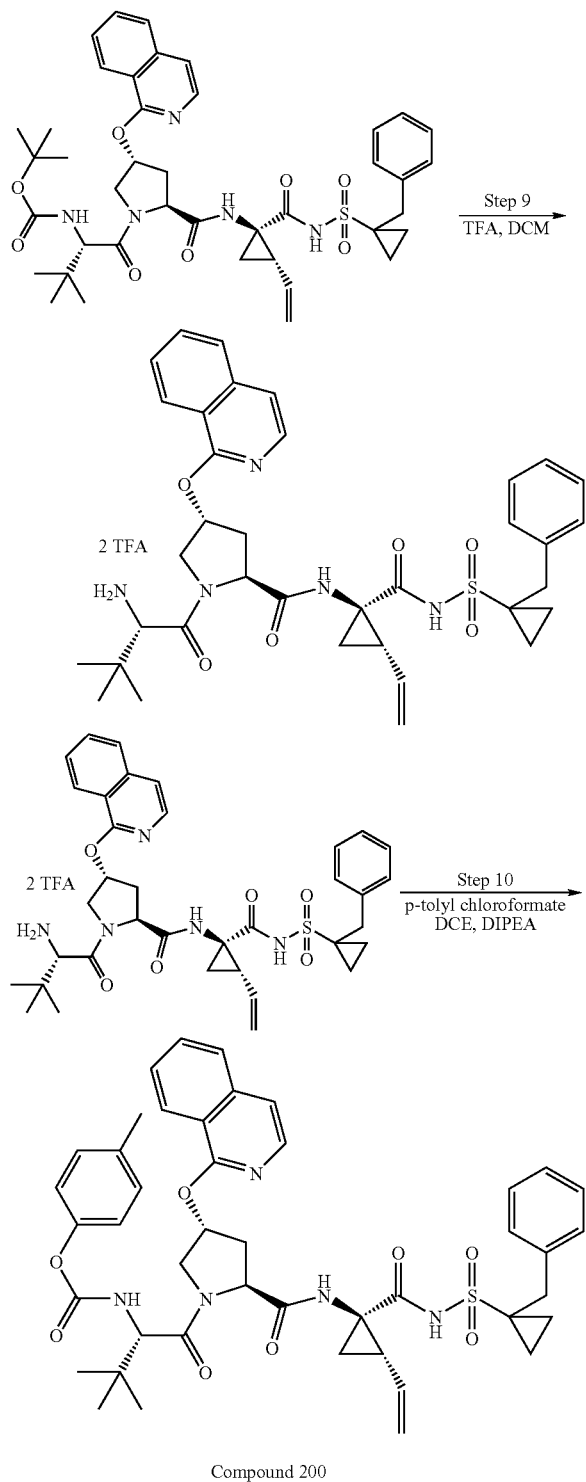

Compound 200

Step 9:

A solution of the product from Example 200, Step 8 (1.50 g, 1.94 mmol) in DCM (50 mL) and trifluoroacetic acid (50 mL) was stirred for 3 h at rt. The mixture was concentrated in vacuo to a viscous residue, and was then dissolved in 1,2-dichloroethane and again concentrated in vacuo to give the desired bis-trifluoroacetic acid salt product as an off-white glassy solid (quantitative). The material was used directly in the next step without purification: MS m/z 674 (MH+).

Step 10:

To a solution of the product from Example 200, Step 9 (125 mg, 0.138 mmol) in 1,2-dichloroethane (3 mL) was added p-tolyl chloroformate (30.5 mg, 0.180 mmol) and N,N-diisopropylethylamine (89.0 mg, 0.692 mmol). The mixture was agitated at rt for 72 h. The reaction mixture was washed with pH=4 buffer solution (3×3 mL), and the washes were back-extracted with 1,2-dichloroethane (3 mL). The organic phases were combined and concentrated in vacuo. The crude product was then dissolved in MeOH and purified by reverse phase preparative HPLC to give Compound 200 as a glassy yellow solid (81.0 mg, 72.6% yield): $^1$H NMR (CD$_3$OD) δ 0.64 (s, 2H), 1.04 (s, 9H), 1.08–1.12 (m, 1H), 1.41–1.48 (m, 3H), 1.93 (dd, J=8.05, 5.49 Hz, 1H), 2.27–2.34 (m, 5H), 2.63–2.69 (m, 1H), 3.78 (s, 1H), 4.09 (dd, J=11.71, 3.66 Hz, 1H), 4.37 (s, 1H), 4.43 (d, J=11.71 Hz, 1H), 4.60 (dd, J=10.06, 7.50 Hz, 1H), 5.18 (d, J=11.34 Hz, 1H), 5.34 (d, J=15.74 Hz, 1H), 5.72–5.81 (m, 1H), 5.85 (s, 1H), 6.78 (d, J=8.42 Hz, 2H), 7.07 (d, J=8.05 Hz, 2H), 7.14–7.17 (m, 2H), 7.22–7.32 (m, 4H), 7.37 (t, J=7.68 Hz, 1H), 7.68 (t, J=7.32 Hz, 1H), 7.78–7.81 (m, 1H), 7.92 (d, J=5.86 Hz, 1H), 8.17 (d, J=8.42 Hz, 1H); MS m/z 808 (MH+), m/z 806 (M–1).

Example 201

Preparation of Compound 201

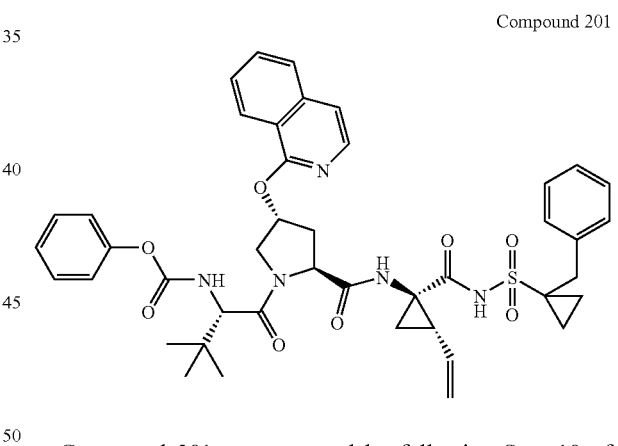

Compound 201

Compound 201 was prepared by following Step 10 of Example 200 except that phenyl chloroformate was used in place of p-tolyl chloroformate.

Step 10:

Modifications: 28 mg (0.18 mmol) phenyl chloroformate used, 69.7 mg product obtained as a yellow glassy solid (63.4% yield): $^1$H NMR (CD$_3$OD) δ 0.64 (s, 2H), 1.04 (s, 9H), 1.08–1.13 (m, 1H), 1.41–1.48 (m, 3H), 1.93 (dd, J=8.05, 5.49 Hz, 1H), 2.24–2.34 (m, 2H), 2.64–2.70 (m, 1H), 3.78 (s, 1H), 4.10 (dd, J=11.89, 3.84 Hz, 1 H), 4.37 (s, 1H), 4.44 (d, J=11.71 Hz, 1H), 4.61 (dd, J=10.06, 7.50 Hz, 1H), 5.16–5.20 (m, 1H), 5.34 (d, J=17.20 Hz, 1H), 5.72–5.81 (m, 1H), 5.85 (s, 1H), 6.91 (d, J=7.68 Hz, 2H), 7.14–7.19 (m, 3H), 7.25–7.32 (m, 6H), 7.37 (t, J=7.68 Hz, 1H), 7.67 (t, J=7.50 Hz, 1H), 7.77–7.80 (m, 1H), 7.92 (d, J=5.86 Hz, 1H), 8.18 (d, J=8.05 Hz, 1H); MS m/z 794 (MH+), m/z 792 (M–1).

Example 202

Preparation of Compound 202

Compound 202

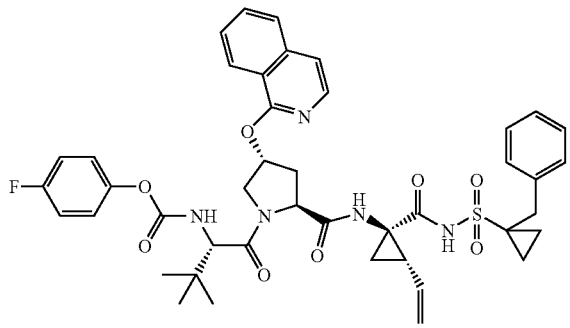

Compound 202 was prepared by following Step 10 of Example 200 except that 4-fluorophenyl chloroformate was used in place of p-tolyl chloroformate.

Step 10:

Modifications: 32 mg (0.18 mmol) 4-fluorophenyl chloroformate used, 71.6 mg product obtained as a glassy yellow solid (63.7% yield): $^1$H NMR (CD$_3$OD) δ 0.64 (s, 2H), 1.03 (s, 9H), 1.08–1.12 (m, 1H), 1.41–1.48 (m, 3H), 1.93 (dd, J=8.05, 5.49 Hz, 1H), 2.25–2.35 (m, 2H), 2.62–2.70 (m, 1H), 3.78 (s, 1H), 4.09 (dd, J=11.71, 3.66 Hz, 1H), 4.35 (s, 1H), 4.43 (d, J=11.71 Hz, 1H), 4.62 (dd, J=9.88, 7.32 Hz, 1H), 5.18 (d, J=11.34 Hz, 1H), 5.35 (d, J=17.20 Hz, 1H), 5.72–5.81 (m, 1H), 5.85 (s, 1H), 6.85–6.90 (m, 2H), 6.98 (t, J=8.60 Hz, 2H), 7.14–7.17 (m, 2H), 7.24–7.32 (m, 4H), 7.40 (t, J=7.50 Hz, 1H), 7.69 (t, J=7.14 Hz, 1H), 7.78–7.81 (m, 1H), 7.92 (d, J=6.22 Hz, 1H), 8.17 (d, J=8.05 Hz, 1H); MS m/z 812 (MH+), m/z 810 (M−1).

Example 203

Preparation of Compound 203

Compound 203

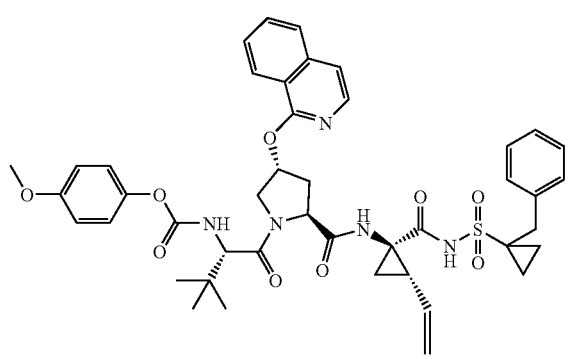

Compound 203 was prepared by following Step 10 of Example 200 except that 4-methoxyphenyl chloroformate was used in place of p-tolyl chloroformate.

Step 10:

Modifications: 33 mg (0.18 mmol) 4-methoxyphenyl chloroformate used, 80.2 mg product obtained as a yellow solid (70.3% yield): $^1$H NMR (CD$_3$OD) δ 0.64 (s, 2H), 103 (s, 9H), 1.07–1.12 (m, 1H), 1.41–1.48 (m, 3H), 1.93 (dd, J=8.05, 5.49 Hz, 1H), 2.25–2.35 (m, 2H), 2.63–2.70 (m, 1H), 3.77 (s, 3H), 3.78 (s, 1H), 4.09 (dd, J=11.53, 3.48 Hz, 1H), 4.36 (s, 1H), 4.43 (d, J=11.71 Hz, 1H), 4.61 (dd, J=9.88, 7.32 Hz, 1H), 5.18 (d, J=11.71 Hz, 1H), 5.35 (d, J=16.47 Hz, 1H), 5.72–5.81 (m, 1H), 5.85 (s, 1H), 6.80 (s, 4H), 7.14–7.17 (m, 2H), 7.24–7.32 (m, 4H), 7.40 (t, J=7.50 Hz, 1H), 7.68 (t, J=7.14 Hz, 1H), 7.78–7.81 (m, 1H), 7.92 (d, J=5.86 Hz, 1H), 8.18 (d, J=8.05 Hz, 1H); MS m/z 824 (MH+), m/z 822 (M−1).

Example 204

Preparation of Compound 204

Compound 204

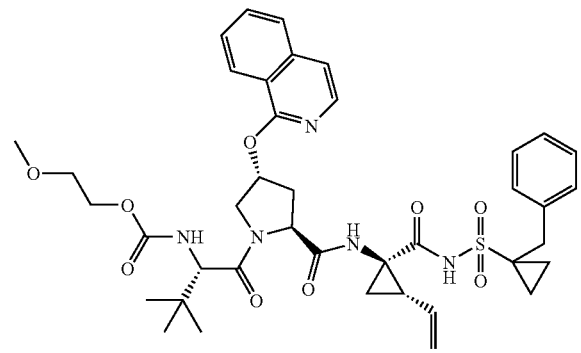

Compound 204 was prepared by following Step 10 of Example 200 except that chloroformic acid 2-methoxyethyl ester was used in place of p-tolyl chloroformate.

Step 10:

Modifications: 25 mg (0.18 mmol) chloroformic acid 2-methoxyethyl ester used, 73.3 mg product obtained as a yellow glassy solid (68.3% yield): $^1$H NMR (CD$_3$OD) δ 0.63 (s, 2H), 0.97 (s, 9H), 1.00–1.05 (m, 1H), 1.41–1.47 (m, 3H), 1.92 (dd, J=8.05, 5.49 Hz, 1H), 2.24–2.35 (m, 2H), 2.62–2.69 (m, 1H), 3.27 (s, 3H), 3.40–3.44 (m, 2H), 3.78 (s, 1H), 3.82–3.89 (m, 1H), 3.92–3.99 (m, 1H), 4.08 (dd, J=11.71, 3.66 Hz, 1H), 4.28–4.31 (m, 1H), 4.44 (d, J=11.71 Hz, 1H), 4.59 (dd, J=9.88, 7.32 Hz, 1H), 5.18 (dd, J=10.25, 1.46 Hz, 1H), 5.34 (dd, J=17.02, 1.65 Hz, 1H), 5.72–5.84 (m, 1H), 5.86 (s, 1H), 7.13–7.16 (m, 2H), 7.24–7.34 (m, 4H), 7.55 (t, J=7.50 Hz, 1H), 7.71 (t, J=7.14 Hz, 1H), 7.80–7.83 (m, 1H), 7.95–7.97 (m, 1H), 8.21 (d, J=8.42 Hz, 1H); MS m/z 776 (MH+), m/z 774 (M−1).

Example 205

Preparation of Compound 205

Compound 205

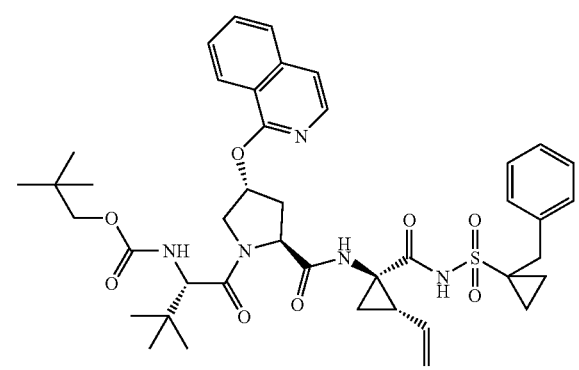

Compound 205 was prepared by following Step 10 of Example 200 except that neopentyl chloroformate was used in place of p-tolyl chloroformate.

Step 10:

Modifications: 27 mg (0.18 mmol) neopentyl chloroformate used, 67.1 mg product obtained as an off-white solid (61.5% yield): $^1$H NMR (CD$_3$OD) δ 0.64 (s, 2H), 0.83 (s, 9H), 0.98 (s, 9H), 1.01–1.05 (m, 1H), 1.42–1.48 (m, 3H), 1.92 (dd, J=8.05, 5.49 Hz, 1H), 2.24–2.35 (m, 2H), 2.61–2.68 (m, 1H), 3.39 (d, J=10.61 Hz, 1H), 3.53–3.56 (m, 1H), 3.78 (s, 1H), 4.08 (dd, J=11.53, 3.48 Hz, 1H), 4.29–4.33 (m, 1H), 4.45 (d, J=11.71 Hz, 1H), 4.59 (dd, J=10.06, 7.14 Hz, 1H), 5.18 (d, J=11.71 Hz, 1H), 5.35 (d, J=16.83 Hz, 1H), 5.73–5.85 (m, 1H), 5.86 (d, J=2.20 Hz, 1H), 7.14–7.16 (m, 2H), 7.24–7.34 (m, 4H), 7.53 (t, J=7.50 Hz, 1H), 7.70 (t, J=7.14 Hz, 1H), 7.80–7.83 (m, 1H), 7.95–7.97 (m, 1H), 8.19 (d, J=8.05 Hz, 1H); MS m/z 788 (MH+), m/z 786 (M−1).

Example 206

Preparation of Compound 206

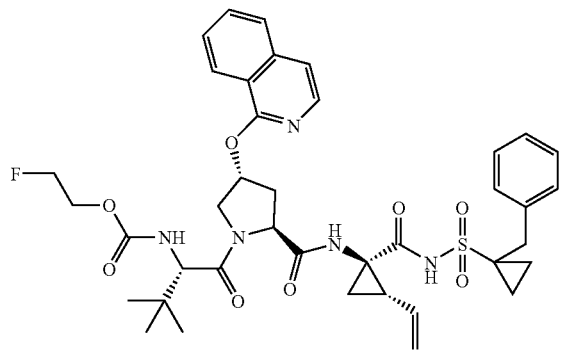

Compound 206

Compound 206 was prepared by following Step 10 of Example 200 except that 2-fluoroethyl chloroformate was used in place of p-tolyl chloroformate.

Step 10:

Modifications: 23 mg (0.18 mmol) 2-fluoroethyl chloroformate used, 75.1 mg product obtained as a yellow glassy solid (71.0% yield): $^1$H NMR (CD$_3$OD) δ 0.63 (s, 2H), 0.98 (s, 9H), 1.00–1.06 (m, 1H), 1.41–1.47 (m, 3H), 1.92 (dd, J=8.05, 5.49 Hz, 1H), 2.24–2.35 (m, 2H), 2.62–2.69 (m, 1H), 3.78 (s, 1H), 3.91–4.10 (m, 3H), 4.28–4.35 (m, 2H), 4.42–4.51 (m, 2H), 4.59 (dd, J=10.06, 7.14 Hz, 1H), 5.18 (dd, J=110.25, 1.46 Hz, 1H), 5.34 (dd, J=17.20, 1.46 Hz, 1H), 5.72–5.84 (m, 1H), 5.86 (s, 1H), 7.13–7.16 (m, 2H), 7.24–7.34 (m, 4H), 7.52–7.57 (m, 1H), 7.68–7.73 (m, 1H), 7.80–7.82 (m, 1H), 7.95–7.97 (m, 1H), 8.20 (d, J=8.42 Hz, 1H); MS m/z 764 (MH+), m/z 762 (M−1).

Example 207

Preparation of Compound 207

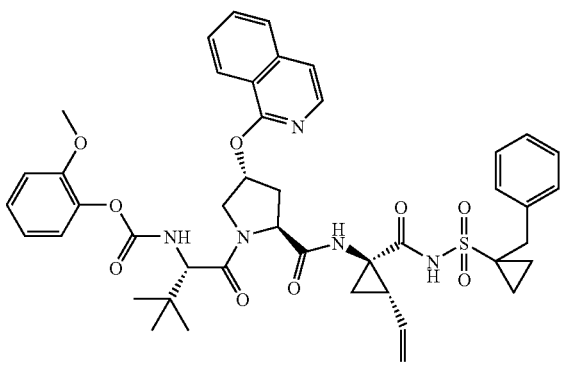

Compound 207

Compound 207 was prepared by following Step 10 of Example 200 except that 2-methoxyphenyl chloroformate was used in place of p-tolyl chloroformate.

Step 10:

Modifications: 33 mg (0.18 mmol) 2-methoxyphenyl chloroformate used, 77.7 mg product obtained as a yellow glassy solid (68.1% yield): $^1$H NMR (CD$_3$OD) δ 0.64 (s, 2H), 1.05 (s, 9H), 1.13–1.16 (m, 1H), 1.41–1.48 (m, 3H), 1.92 (dd, J=8.05, 5.12 Hz, 1H), 2.25–2.37 (m, 2H), 2.63–2.70 (m, 1H), 3.65 (s, 3H), 3.78 (s, 2H), 4.13 (dd, J=11.53, 3.48 Hz, 1H), 4.35–4.39 (m, 2H), 4.61 (dd, J=9.33, 7.50 Hz, 1H), 5.18 (d, J=11.34 Hz, 1H), 5.35 (d, J=16.83 Hz, 1H), 5.73–5.82 (m, 1H), 5.85 (s, 1H), 6.87 (d, J=3.66 Hz, 2H), 6.98 (d, J=8.42 Hz, 1H), 7.14–7.17 (m, 3H), 7.24–7.32 (m, 4H), 7.42 (t, J=7.50 Hz, 1H), 7.68 (t, J=7.32 Hz, 1H), 7.77–7.80 (m, 1H), 7.92 (d, J=5.49 Hz, 1H), 8.18 (d, J=8.05 Hz, 1H); MS m/z 824 (MH+), m/z 822 (M−1).

Example 208

Preparation of Compound 208

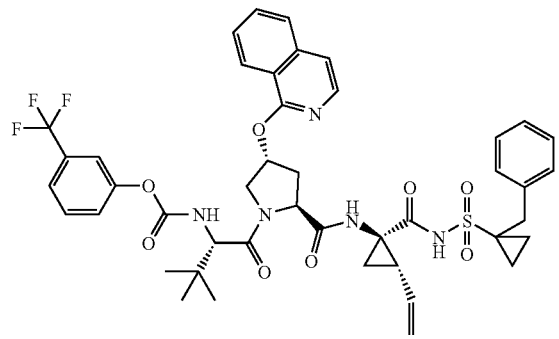

Compound 208

Compound 208 was prepared by following Step 10 of Example 200 except that 3-trifluoromethylphenyl chloroformate was used in place of p-tolyl chloroformate.

Step 10:

Modifications: 40 mg (0.18 mmol) 3-trifluoromethylphenyl chloroformate used, 45.2 mg product obtained as a slightly yellow glassy solid (37.9% yield): MS m/z 862 (MH+), m/z 860 (M−1).

Example 209

Preparation of Compound 209

Compound 209

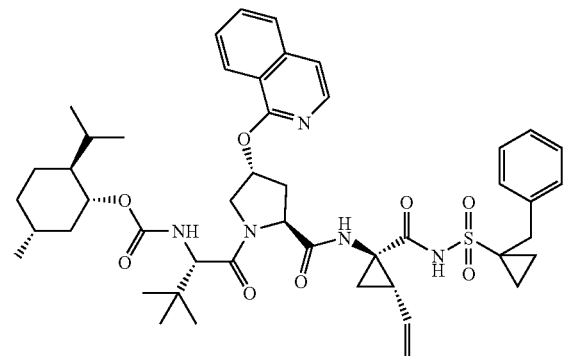

Compound 209 was prepared by following Step 10 of Example 200 except that 2-(−)-(1R)-menthyl chloroformate was used in place of p-tolyl chloroformate.

Step 10:

Modifications: 40 mg (0.18 mmol) (−)-(1R)-menthyl chloroformate used, 74.9 mg product obtained as an off-white solid (63.2% yield): MS m/z 856 (MH+), m/z 854 (M−1).

Example 210

Preparation of Compound 210

Compound 210

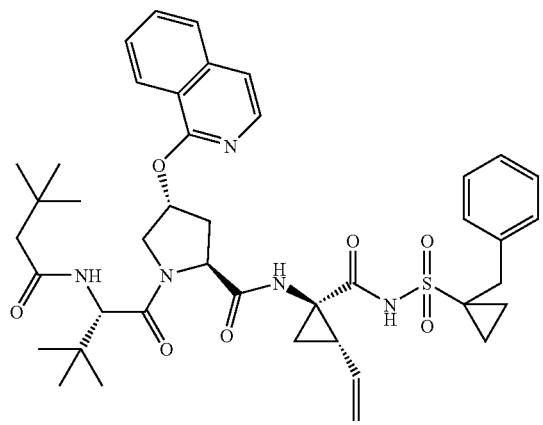

-continued

Scheme 1

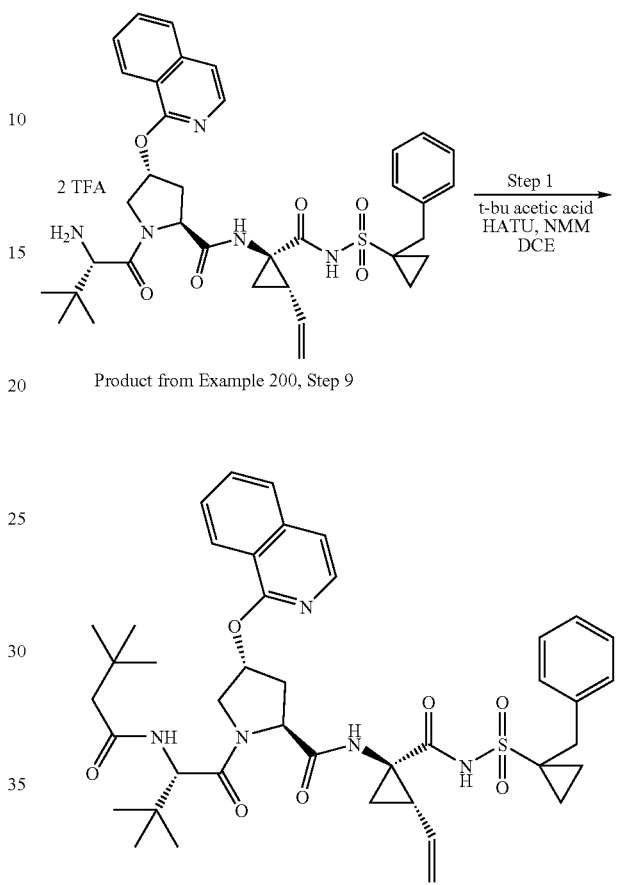

Product from Example 200, Step 9

Compound 210

Step 1:

A mixture of the product from Example 100, Step 9 (125 mg, 0.138 mmol), tert-butyl acetic acid (20.7 mg, 0.18 mmol), HATU (68 mg, 0.18 mmol) and N-methylmorpholine (55 mg, 0.55 mmol) in 1,2-dichloroethane was stirred for 24 h at rt. The reaction mixture was washed with pH=4 buffer solution (3×3 mL), and the washes were back-extracted with 1,2-dichloroethane (3 mL). The organic phases were combined and concentrated in vacuo. The crude product was then dissolved in MeOH and purified by reverse phase preparative HPLC to give the title compound (Compound 210) as a yellow glassy solid (60.7 mg, 56.8% yield): $^1$H NMR (CD$_3$OD) δ 0.59–0.69 (m, 2H), 0.82 (s, 9H), 0.98 (s, 9H), 1.02–1.06 (m, 2H), 1.42–1.52 (m, 3H), 1.92 (dd, J=8.23, 5.31 Hz, 1H), 1.99 (s, 2H), 2.23–2.35 (m, 2H), 2.60–2.67 (m, 1H), 4.11 (dd, J=11.89, 3.84 Hz, 1H), 4.43 (d, J=12.08 Hz, 1H), 4.57 (dd, J=10.25, 6.95 Hz, 1H), 4.63–4.67 (m, 1H), 5.18 (dd, J=10.25, 1.83 Hz, 1H), 5.34 (dd, J=17.20, 1.46 Hz, 1H), 5.73–5.82 (m, 1H), 5.85–5.88 (m, 1H), 7.14–7.16 (m, 2H), 7.24–7.33 (m, 4H), 7.53 (dt, J=7.50, 1.10 Hz, 1H), 7.71 (dt, J=7.50, 1.10 Hz, 1H), 7.78–7.82 (m, 1H), 7.95 (d, J=5.86 Hz, 1H), 8.17 (d, J=8.05 Hz, 1H); MS m/z 772 (MH+), m/z 770 (M−1).

Example 211

Preparation of Compound 211

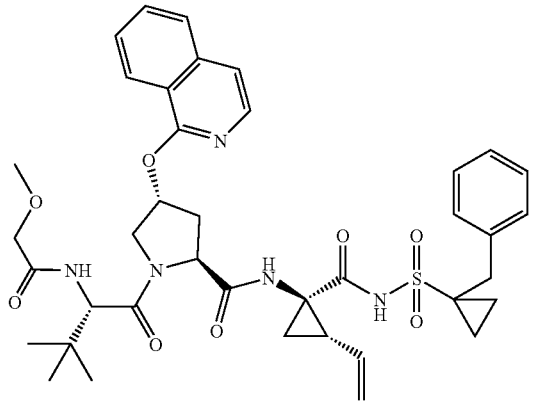

Compound 211

Compound 211 was prepared by following Step 1 of Example 210 except that methoxyacetic acid was used in place of tert-butyl acetic acid.

Step 1:

Modifications: 16 mg (0.18 mmol) methoxyacetic acid used, 65.8 mg product obtained as a yellow glassy solid (63.7% yield): $^1$H NMR (CD$_3$OD) δ 0.61–0.66 (m, 2H), 0.99 (s, 9H), 1.01–1.06 (m, 1H), 1.42–1.52 (m, 3H), 1.92 (dd, J=8.23, 5.31 Hz, 1H), 2.24–2.37 (m, 2H), 2.61–2.69 (m, 1H), 3.35 (s, 3H), 3.68 (d, J=15.00 Hz, 1H), 3.78 (s, 1H), 3.83 (d, J=115.00 Hz, 1H), 4.13 (dd, J=11.89, 3.84 Hz, 1H), 4.36 (d, J=12.08 Hz, 1H), 4.59 (d, J=10.06, 7.14 Hz, 1H), 4.65 (s, 1H), 5.18 (dd, J=10.25, 1.83 Hz, 1H), 5.35 (dd, J=17.20, 1.46 Hz, 1H), 5.80 (ddd, J=17.20, 10.25, 9.15 Hz, 1H), 5.86–5.89 (m, 1H), 7.15 (dd, J=7.68, 1.46 Hz, 2H), 7.24–7.34 (m, 4H), 7.56 (ddd, J=8.23, 6.95, 1.28 Hz, 1H), 7.71 (ddd, J=8.23, 6.95, 1.28 Hz, 1H), 7.80–7.83 (m, 1H), 7.96 (d, J=6.22 Hz, 1H), 8.16 (d, J=8.42 Hz, 1H); MS m/z 746 (MH+), m/z 744 (M−1).

Example 212

Preparation of Compound 212

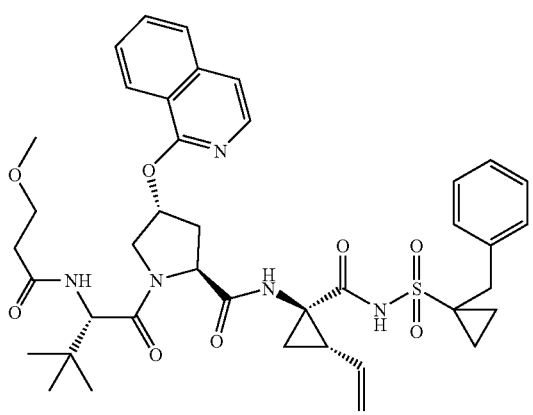

Compound 212

Compound 212 was prepared by following Step 1 of Example 210 except that methoxyprop ionic acid was used in place of tert-butyl acetic acid.

Step 1:

Modifications: 20 mg (0.18 mmol) methoxypropionic acid used, 73.9 mg product obtained as a yellow glassy solid (70.3% yield): $^1$H NMR (CD$_3$OD) δ 0.59–0.68 (m, 2H), 0.98 (s, 9H), 1.02–1.06 (m, 1H), 1.46 (m, 3H), 1.92 (dd, J=8.23, 5.31 Hz, 1H), 2.24–2.47 (m, 4H), 2.60–2.69 (m, 1H), 3.25 (s, 3H), 3.43–3.55 (m, 2H), 3.78 (s, 1H), 4.13 (dd, J=11.71, 4.03 Hz, 1H), 4.38 (d, J=11.71 Hz, 1H), 4.57 (dd, J=9.88, 7.32 Hz, 1H), 4.62 (s, 1H), 5.18 (dd, J=10.43, 1.65 Hz, 1H), 5.35 (dd, J=17.20, 1.46 Hz, 1H), 5.73–5.82 (m, 1H), 5.85–5.89 (m, 1H), 7.15 (dd, J=7.87, 1.28 Hz, 2H), 7.22–7.34 (m, 4H), 7.56 (ddd, J=8.23, 6.95, 1.28 Hz, 1H), 7.71 (ddd, J=8.23, 6.95, 1.28 Hz, 1H), 7.80–7.83 (m, 1H), 7.96 (d, J=5.86 Hz, 1H), 8.18 (d, J=8.42 Hz, 1H); MS m/z 760 (MH+), m/z 758 (M−1).

Example 213

Preparation of Compound 213

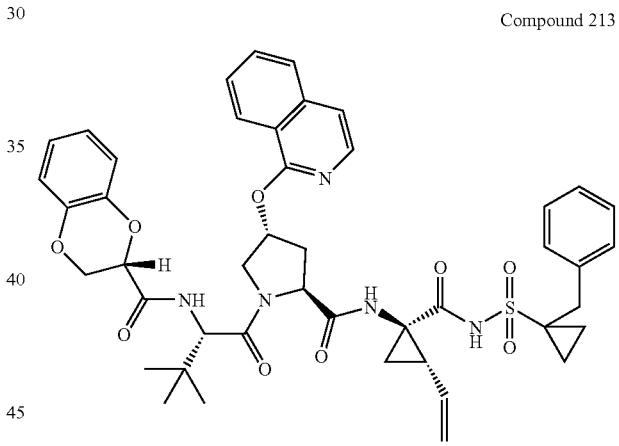

Compound 213

Compound 213 was prepared by following Step 1 of Example 210 except that (S)-1,4-benzodioxane-2-carboxylic acid was used in place of tert-butyl acetic acid.

Step 1:

Modifications: 33 mg (0.18 mmol) (S)-1,4-benzodioxane-2-carboxylic acid used, 72.4 mg product obtained as a yellow glassy solid (62.6% yield): $^1$H NMR (CD$_3$OD) δ 0.61–0.67 (m, 2H), 0.76 (s, 9H), 0.78–0.82 (m, 1H), 1.44–1.50 (m, 3H), 1.92 (dd, J=8.42, 5.49 Hz, 1H), 2.23–2.37 (m, 2H), 2.61–2.69 (m, 1H), 3.78 (s, 1H), 4.09–4.17 (m, 2H), 4.32–4.37 (m, 2H), 4.56–4.64 (m, 3H), 5.18 (dd, J=10.25, 1.83 Hz, 1H), 5.35 (dd, J=17.02, 1.28 Hz, 1H), 5.75–5.84 (m, 1H), 5.87–5.90 (m, 1H), 6.79–6.91 (m, 3H), 7.04–7.07 (m, 1H), 7.13–7.15 (m, 2H), 7.23–7.35 (m, 4H), 7.53–7.59 (m, 1H), 7.67–7.72 (m, 1H), 7.80–7.83 (m, 1H), 7.97 (d, J=5.86 Hz, 1H), 8.17 (d, J=8.42 Hz, 1H); MS m/z 836 (MH+), m/z 834 (M−1).

Example 215

Preparation of Compound 216

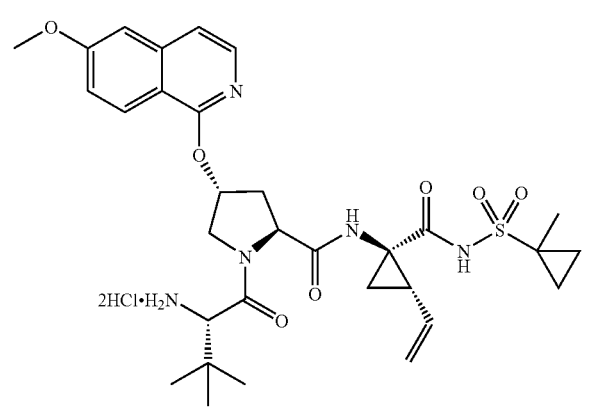

Compound 216

Scheme 1.

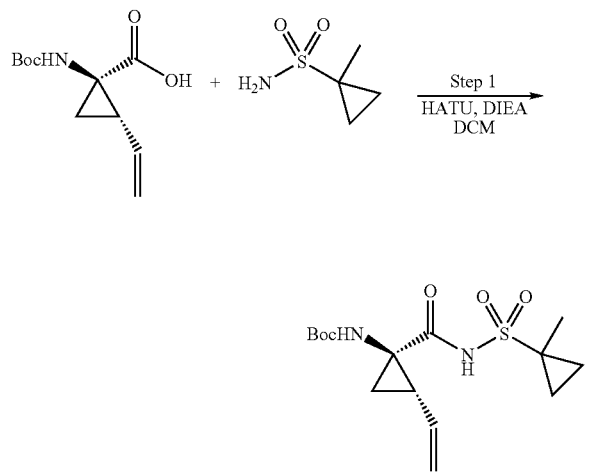

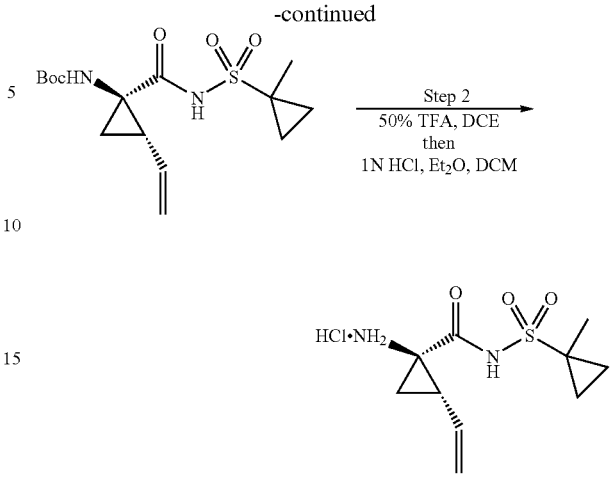

Step 1:
To a solution of 1R-tert-butoxycarbonylamino-2S-vinyl-cyclopropanecarboxylic acid (2.3 g, 10.11 mmol) in THF (40 mL) was added CDI (1.80 g, 11.6 mmol) and was heated to 85° C. for 30 min. After let cool to rt, the reaction mixture was treated with 1-methyl-cyclopropanesulfonam (1.64 g, 12.1 mmol) and DBU (3.08 g, 20.2 mmol). After stirring at rt for 16 h, the reaction was diluted with EtOAc (160 mL) and washed with 2×25 mL 1N HCl. The combined aqueous layer was extracted with 1×50 mL EtOAc. The combined organic layer was washed with $H_2O$ (50 mL), brine, dried over MgSO4 and concentrated to a light yellow solid product (2.75 g, 79%). The product was used as crude. MS m/z 367 (M+Na).

Step 2:
To a solution of the product from step 1 of Example 216 (2.66 g, 7.72 mmol) in DCM (15 mL) was added TFA (15 mL) and was stirring rt for 15 min. Solvent was concentrated. The resulting brown oil was redissolved in DCE (30 mL) and reconcentrated. It was then redissolved in DCM (15 mL) and treated with a solution of 1N HCl in $Et_2O$ (30 mL) dropwise. The light yellow precipitation product was obtained by cacuum filtration and washed with $Et_2O$ (2.2 g, quantatative yield). The product was used as crude: MS m/z 245 ($MH^+$).

Scheme 2

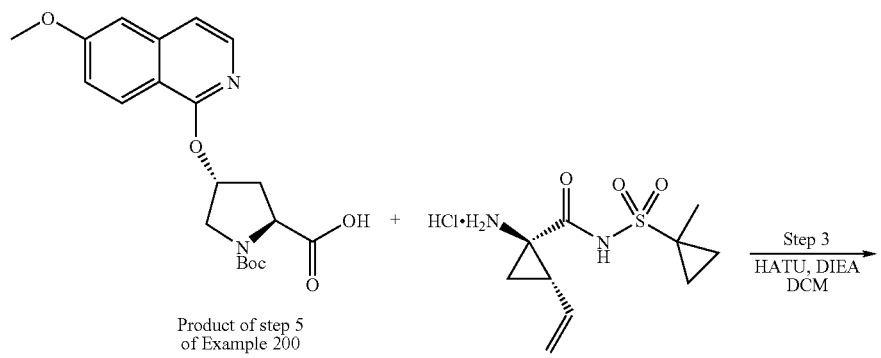

Product of step 5
of Example 200

-continued

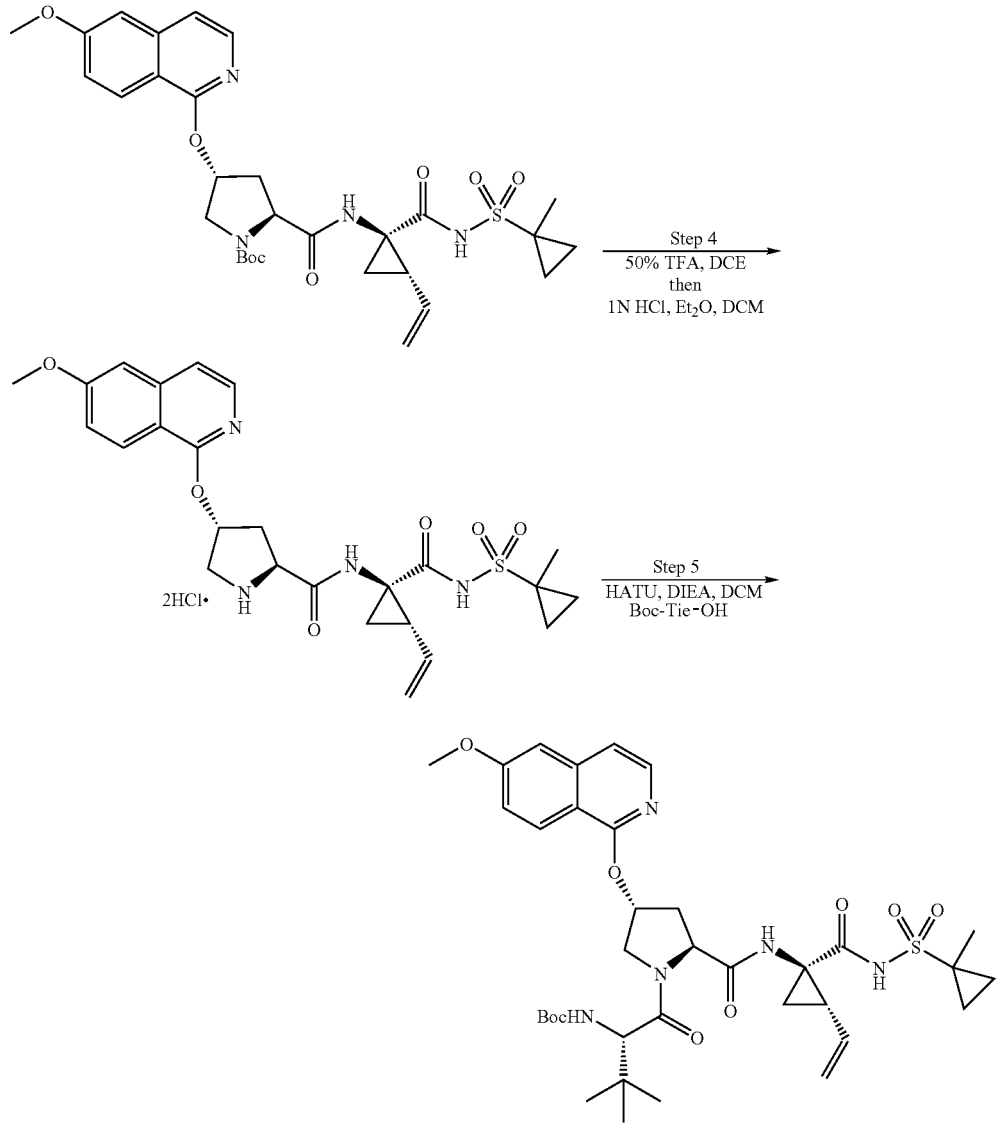

Compound 301

Step 3:

To a solution mixture of the product from Step 5 of Example 200 (1.70 g, 4.38 mmol), DIEA (1.42 g, 10.95 mmol) and the product from Step 2 of Example 216 (1.23 g, 4.38 mmol) in DCM (44 mL) was added HATU (2.16 g, 5.69 mmol). After stirring the reaction mixture at rt for 5 h, it was diluted with DCM (50 mL) and washed with 5% aqueous NaHCO$_3$ (25 mL). The aqueous layer was extracted with 1×25 mL DCM. The combined organic layer was washed with 5% aqueous citric acid (50 mL), H$_2$O (25 mL), brine, dried over MgSO$_4$ and concentrated. Crude product was purified by reverse phase prep-HPLC to give a white foam (1.78 mg, 66% yield): MS m/z 615 (MH$^+$).

Step 4:

To a solution of the product from step 3 of Example 216 (1.78 g, 2.90 mmol) in DCM (6 mL) was added TFA (6 mL) and was stirring rt for 20 min. Solvent was concentrated. The resulting brown oil was redissolved in DCE (50 mL) and reconcentrated. It was then redissolved in DCM (5 mL) and treated with a solution of 1N HCl in Et$_2$O (30 mL) dropwise. The brown precipitation product was obtained by cacuum filtration and washed with Et$_2$O (1.7 g, quantatative yield). The product was used as crude: MS m/z 515 (MH$^+$).

Step 5:

To a solution mixture of the product from Step 4 of Example 216 (1.25 g, 2.13 mmol), DIEA (1.10 g, 8.52 mmol) and Boc-L-Tle-OH (0.640, 2.76 mmol) in DCM (21 mL) was added HATU (1.21 g, 3.20 mmol). After stirring the reaction mixture at rt for 5 h, it was diluted with DCM (30 mL) and washed with 5% aqueous NaHCO$_3$ (15 mL). The aqueous layer was extracted with 1×25 mL DCM. The combined organic layer was washed with 5% aqueous citric acid (30 mL), H$_2$O (15 mL), brine, dried over MgSO$_4$ and concentrated. Crude product was purified by flash column chromatography to give Compound 301 as a white foam (1.24 g, 80% yield): MS m/z 728 (MH$^+$).

Scheme 3

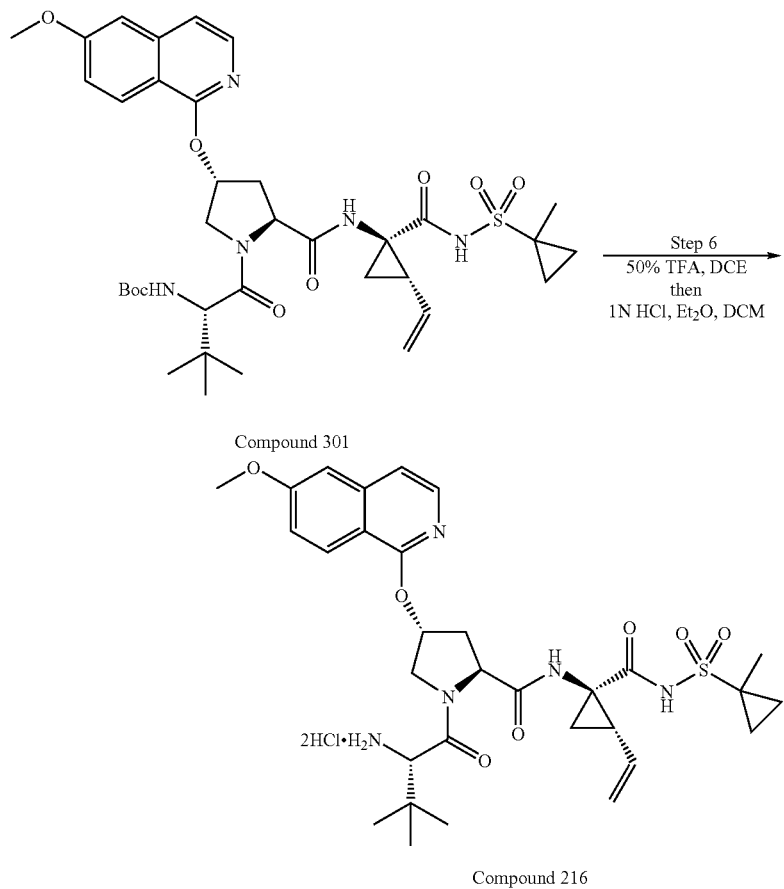

Compound 301

Compound 216

Step 6:
To a solution of Compound 301 (1.1 g, 1.51 mmol) in DCM (5 mL) was added TFA (5 mL) and was stirring rt for 20 min. Solvent was concentrated. The resulting brown oil was redissolved in DCE (15 mL) and reconcentrated. It was then redissolved in DCM (3 mL) and treated with a solution of 1N HCl in Et$_2$O (15 mL) dropwise. The brown precipitation product was obtained by cacuum filtration and washed with Et$_2$O (1.04 g, quantatative yield). The product was used as crude: MS m/z 628(MH$^+$).

Example 217

Preparation of Compound 217

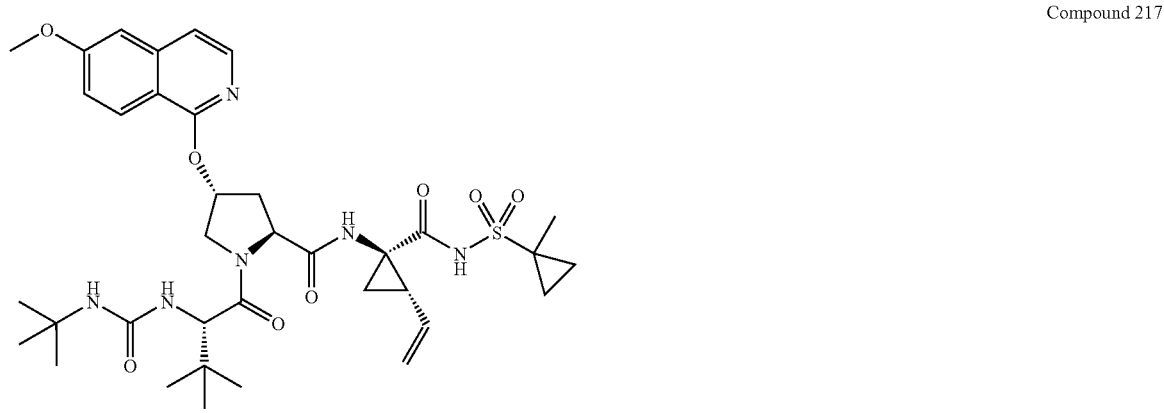

Compound 217

-continued
Scheme 1

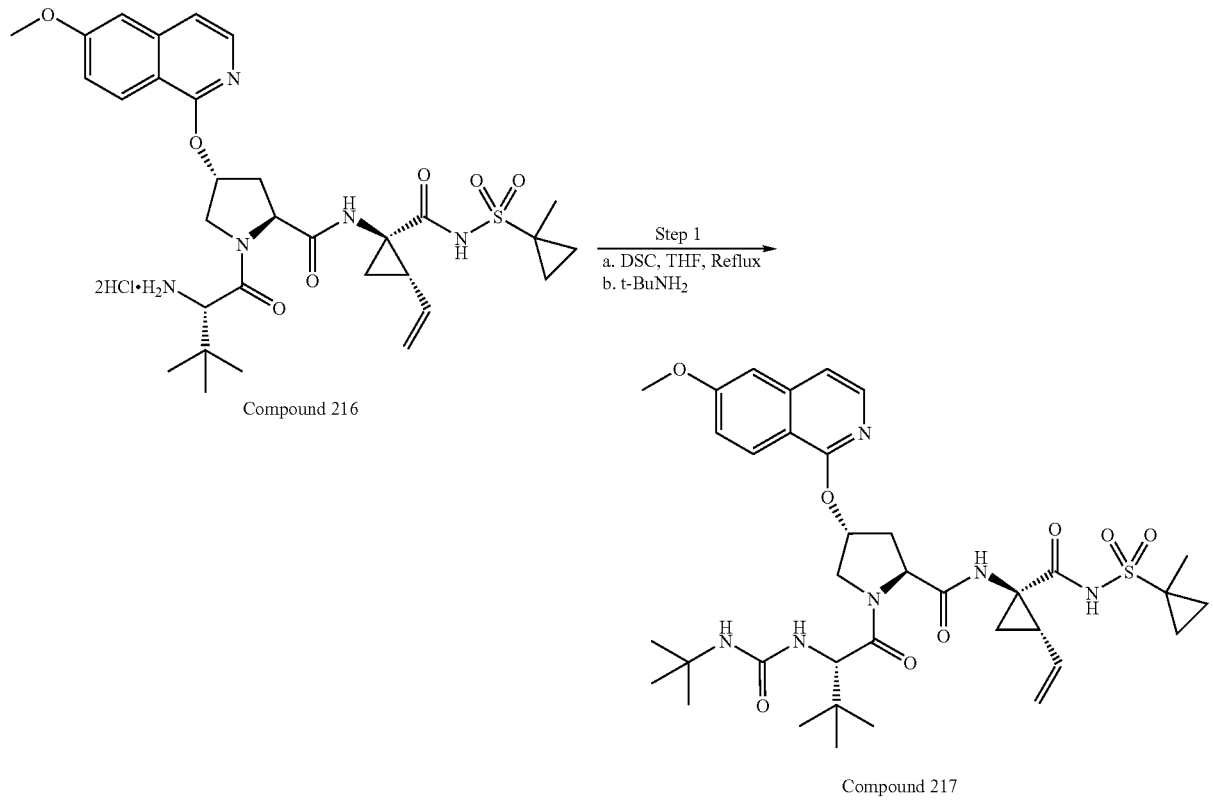

Compound 216

Step 1
a. DSC, THF, Reflux
b. t-BuNH₂

Compound 217

Step 1:
To a solution mixture of Compound 216 (0.102 g, 0.146 mmol) and DIEA (47.3 m g, 0.365 mmol) in THF (2 mL) was added DSC (55.9 mg, 0.218 mmol). The reaction mixture was irradiated in a microwave to 80° C. for 15 min. After let cooled to rt, the reaction was treated with tert-butylamine (0.107 g, 1.46 mmol). It was then stirred at rt for 1 h, concentrated and purified by reversed-phase prep-HPLC to give a white solid product (62.2 mg, 60% yield). MS m/Z 727 (MH$^+$).

Example 218

Preparation of Compound 218

Example 218

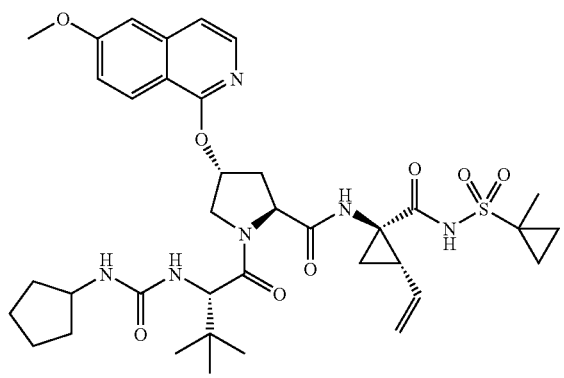

Compound 218 was prepared by the same methods as Compound 217 with the following modifications:

Modifications: cyclopentylamine was used as a starting material to give Compound 218 (57.5 mg, 53% yield): MS m/z 739 (MH$^+$).

Example 219

Preparation of Compound 219

Compound 219

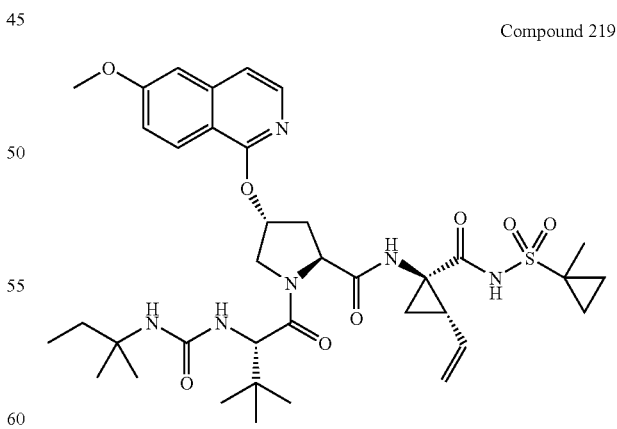

Compound 219 was prepared by the same methods as Compound 217 with the following modifications:

Modifications: Tert-amylamine was used as a starting material to give Compound 219 (58.3 mg, 54% yield): MS m/z 741 (MH$^+$).

Example 220

Preparation of Compound 220

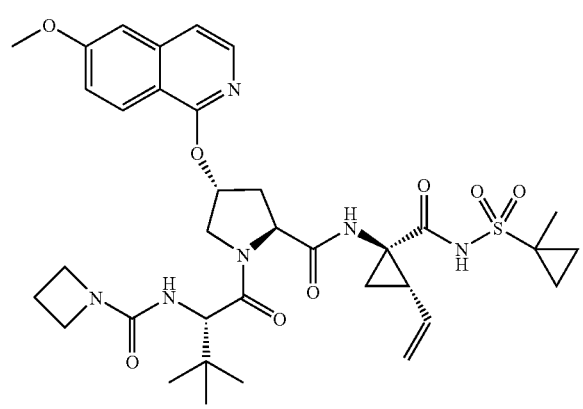

Compound 220

Compound 220 was prepared by the same methods as Compound 217 with the following modifications:

Modifications: Tert-amylamine was used as a starting material to give Compound 220 (10.0 mg, 20% yield): MS m/z 711 (MH+).

Section D

Preparation of Compounds 300–304

LC-MS Condition:
Columns:
 (Method A)—Xterra MS C18 S7 3.0×50 mm
 (Method B)—Xterra S7 3.0×50 mm
 (Method C)—Xterra S7 C18 3.0×50 mm
Solvent A: 10% MeOH-90% $H_2O$-0.1% TFA
Solvent B: 90% MeOH-10% $H_2O$-0.1% TFA
Gradient time: 2 min. (A, B, C)
Hold time: 1 min. (A, B, C)
Flow rate: 5 mL/min (A, B, C))

Example 300

Preparation of Compound 300 {1-[2-[1-(1-Ethyl-cyclopropanesulfonylaminocarbonyl)-2-vinyl-cyclopropylcarbamoyl]-4-(6-methoxy-isoquinolin-1-yloxy)-pyrrolidine-1-carbonyl]-2,2-dimethyl-propyl}-carbamic acid tert-butyl ester

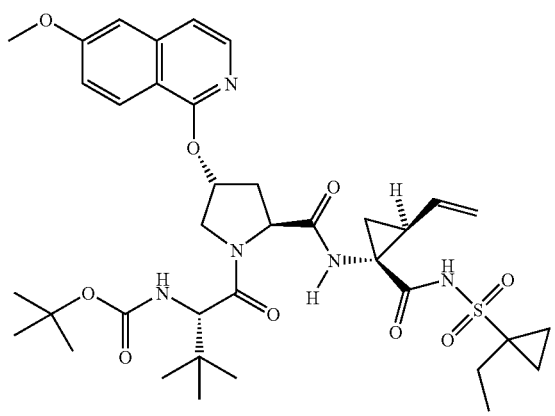

compound 300

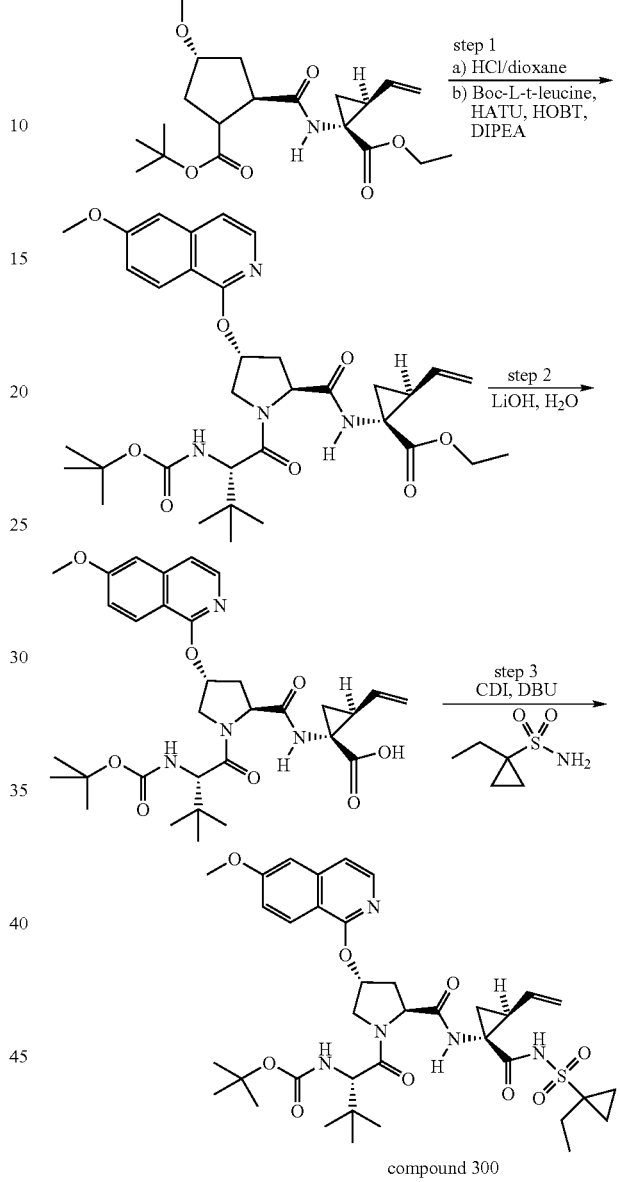

Step 1:

A slurry of P2 Boc-(4R)-(6-methoxy-isoquinoline-1-oxo)-S-proline]-P1(1R,2S Vinyl Acca)-COOEt (7.88 g, 14.99 mmol) in 4M HCl/dioxane (120 mL, 480 mmol) was stirred for 2 h, removed the solvent in vacuo and azeotroped with dry dioxane. To the residue was added DMF (75 mL), N-mehtylmorpholine (6.27 mL, 57.07 mmol), Boc-L-tert-leucine (5.20 g, 22.49 mmol), and HATU (8.53 g, 22.49 mmol). The reaction mixture was stirred at rt overnite and worked up by pouring the reaction mixture into ice water and adjusted to pH 5 with aqueous 1.0 N HCl and extracted with EtOAc. The extract was washed with $NaHCO_3$ (aq.), brine, dried ($MgSO_4$) and concentrated. The residue was purified over Biotage 65M column (EtOAc-hexanes: 5–100%) to provide the product (8.07 g, 84%): Retention time: 1.88 method C) MS m/z 639 (M++1).

Step 2:

To a suspension of the product (4.0 g, 6.26 mmol) of Step 1 of Example 384 {Boc-NH-P3 (L-tert-BuGly)-P2 [(4R)-(6-methoxyl-isoquinoline-1-oxo)-S-proline]-P1 (1R,2S Vinyl Acca)-COOEt} in THF (250 mL), CH₃OH (31 mL), and H₂O (125 mL) was added LiOH (2.4 g, 100.2 mmol). The reaction mixture was stirred for overnite and then adjusted to pH 7 with aqueous 1.0 N HCl. The organic solvents were removed in vacuo. The aqueous residue was acidified to pH 4 and extracted with EtOAc (2×).

The combined organic solvent was dried (Na₂SO₄/MgSO₄), and concentrated in vacuo to supply the product (3.79 g, 99%): ¹H NMR (methanol-d₄) δ ppm 1.05 (s, 9H), 1.25 (m, 1H), 1.29 (s, 9H), 1.46 (m, 1H), 1.72 (dd, J=8.24, 5.19 Hz, 1H), 2.23 (q, J=8.55 Hz, 1H), 2.68 (dd, J=13.89, 7.78 Hz, 1H), 3.94 (s, 3H), 4.05 (dd, J=11.60, 3.05 Hz, 1H), 4.23 (d, J=8.85 Hz, 1H), 4.46 (d, J=11.60 Hz, 1H), 4.63 (t, J=8.39 Hz, 1H), 5.10 (d, J=10.38 Hz, 1H), 5.29 (d, J=17.40 Hz, 1H), 5.85 (m, 2H), 7.10 (d, J=9.16 Hz, 1H), 7.19 (s, 1H), 7.26 (d, J=5.49 Hz, 1H), 7.91 (d, J=5.80 Hz, 1H), 8.12 (d, J=9.16 Hz, 1H). LC-MS (Retention time: 1.81 method C) MS m/z 611 (M⁺+1).

A solution of CDI (0.142 g, 0.87 mmol) and the product (0.400 g, 0.58 mmol) of Step 2 of Example 300 {BOCNH-P3(L-t-BuGly)-P2[(4R)-6-methoxy-sioquinoline-1-oxo)-S-proline]-P1(1R,2S Vinyl Acca)-CO₂H} in THF (8 mL) was heated at 70° C. for 60 min and allowed to cool down to rt. The reaction solution was evenly divided by syringe into four flask. To one of the flask was added 1-ethyl-cyclopropanesulfonamide (0.039 g, 0.26 mmol) and followed by the addition of a solution of neat DBU (0.048 mL, 0.32 mmol). The reaction was stirred for overnite, then filtered through syringe filter and purified by preparative HPLC (solvent B: 50% to 100%) and to provide the Comound 300 (0.0638 mg); ¹H NMR (500 MHz, Solvent: methanol-d₄) δ ppm 0.94 (m, 2H), 0.98 (t, J=7.48 Hz, 3H), 1.03 (d, J=3.66 Hz, 9H), 1.27 (s, 9H), 1.41 (dd, J=9.16, 5.49 Hz, 1H), 1.52 (m, 2H), 1.85 (m, 2H), 1.97 (m, 1H), 2.25 (m, 2H), 2.61 (dd, J=13.89, 7.17 Hz, 1H), 3.92 (s, 3H), 4.05 (m, 1H), 4.25 (s, 1H), 4.43 (d, J=12.21 Hz, 1H), 4.54 (m, 1H), 5.11 (d, J=10.38 Hz, 1H), 5.28 (d, J=17.09 Hz, 1H), 5.71 (m, 1H), 5.83 (s, 1H), 7.09 (d, J=8.85 Hz, 1H), 7.18 (s, 1H), 7.25 (d, J=5.80 Hz, 1H), 7.88 (d, J=5.80 Hz, 1H), 8.09 (d, J=9.46 Hz, 1H); LC-MS (Retention time: 1.92 method A), MS m/z 742 (M⁺+1).

Example 301

Preparation of Compound 301; (1-{4-(6-Methoxy-isoquinolin-1-yloxy)-2-[1-(1-methyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester compound 301

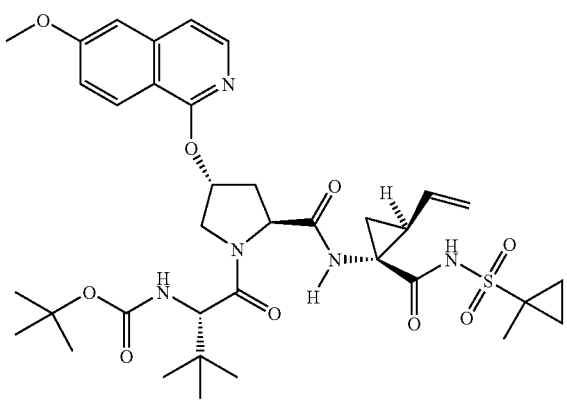

-continued

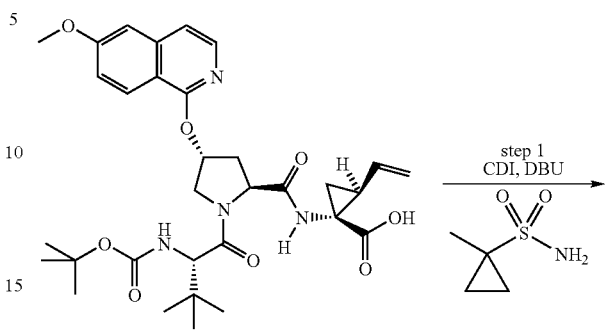

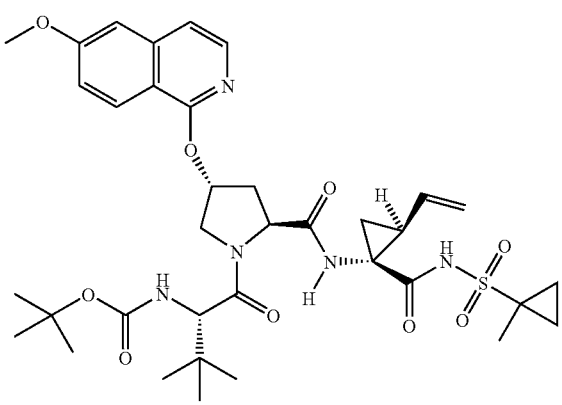

compound 301

Step 1:

Compound 301 was prepared in the same procedure as described in Step 3 of Example 300 in preparation of Compound 300 instead of 1-methyl-cyclopropanesulfonamide (0.039 g, 0.26 mmol), was used in the place of 1-ethyl-cyclopropanesulfonamide, but purified by combination of Prep-HPLC (solvent B: 40% to 100%) and P-TLC (MeOH/CH₂Cl₂: 0% to 5%) as a white foam (0.0721 g). ¹H NMR (500 MHz, Solvent: methanol-d₄) δ ppm 0.93 (m, 2H), 1.06 (s, 9H), 1.30 (s, 9H), 1.43 (dd, J=9.31, 5.34 Hz, 1H), 1.52 (s, 3H), 1.59 (m, 2H), 1.89 (m, 1H), 2.28 (m, 2H), 2.65 (dd, J=14.04, 7.32 Hz, 1H), 3.95 (s, 3H), 4.09 (m, 1H), 4.29 (d, J=9.46 Hz, 1H), 4.47 (d, J=11.29 Hz, 1H), 4.57 (m, 1H), 5.15 (d, J=10.68 Hz, 1H), 5.32 (d, J=16.79 Hz, 1H), 5.74 (m, 1H), 5.86 (s, 1H), 6.62 (d, J=9.16 Hz, 1H), 7.12 (d, J=8.85 Hz, 1H), 7.21 (s, 1H), 7.27 (d, J=5.49 Hz, 1H), 7.91 (d, J=6.10 Hz, 1H), 8.12 (d, J=9.16 Hz, 1H), LC-MS (Retention time: 1.86 method A), MS m/z 728 (M⁺+1).

Example 302

Preparation of Compound 302; (1-{4-(6-Methoxy-isoquinolin-1-yloxy)-2-[1-(1-propyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

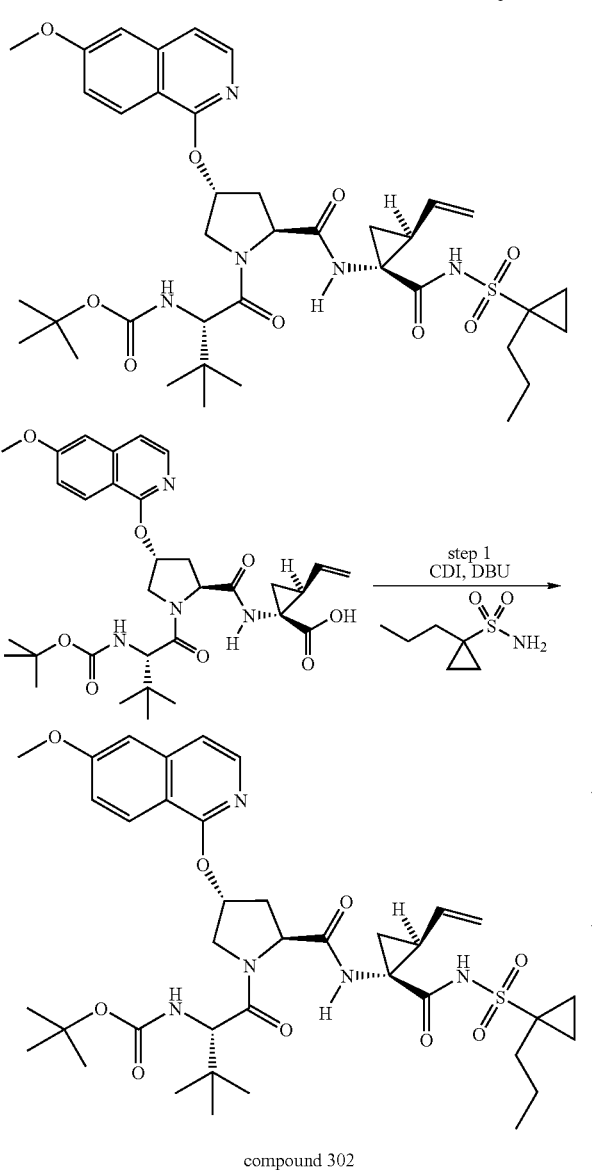

compound 302

Step 1:

Compound 302 was prepared in the same procedure as described in Step 3 of Example 300 in preparation of Compound 300 instead of 1-methyl-cyclopropanesulfonamide (0.039 g, 0.26 mmol), was used in the place of 1-ethyl-cyclopropanesulfonamide, and purified by Prep-HPLC (solvent B: 50% to 100%) as a white foam (0.0628 g). $^1$H NMR (500 MHz, Solvent: methanol-$d_4$) δ ppm 0.91 (t, J=7.32 Hz, 4H), 0.94 (m, 2H), 1.04 (s, 9H), 1.28 (s, 9H), 1.45 (m, 3H), 1.59 (m, 1H), 1.73 (m, 1H), 1.88 (m, 2H), 2.26 (m, 2H), 2.61 (dd, J=13.73, 7.32 Hz, 1H), 3.92 (s, 3H), 4.06 (m, 1H), 4.25 (s, 1H), 4.43 (d, J=12.21 Hz, 1H), 4.45 (m, 1H), 5.11 (d, J=10.07 Hz, 1H), 5.29 (d, J=18.01 Hz, 1H), 5.72 (m, 1H), 5.84 (s, 1H), 7.09 (d, J=8.85 Hz, 1H), 7.18 (s, 1H), 7.25 (d, J=6.10 Hz, 1H), 7.88 (d, J=6.10 Hz, 1H), 8.09 (d, J=8.85 Hz, 1H); LC-MS (Retention time: 1.97 method A), MS m/z 756 (M$^+$+1).

Example 303

Preparation of Compound 303; {1-[2-[1-(1-Benzyl-cyclopropanesulfonylaminocarbonyl)-2-vinyl-cyclopropylcarbamoyl]-4-(6-methoxy-isoquinolin-1-yloxy)-pyrrolidine-1-carbonyl]-2,2-dimethyl-propyl}-carbamic acid tert-butyl ester

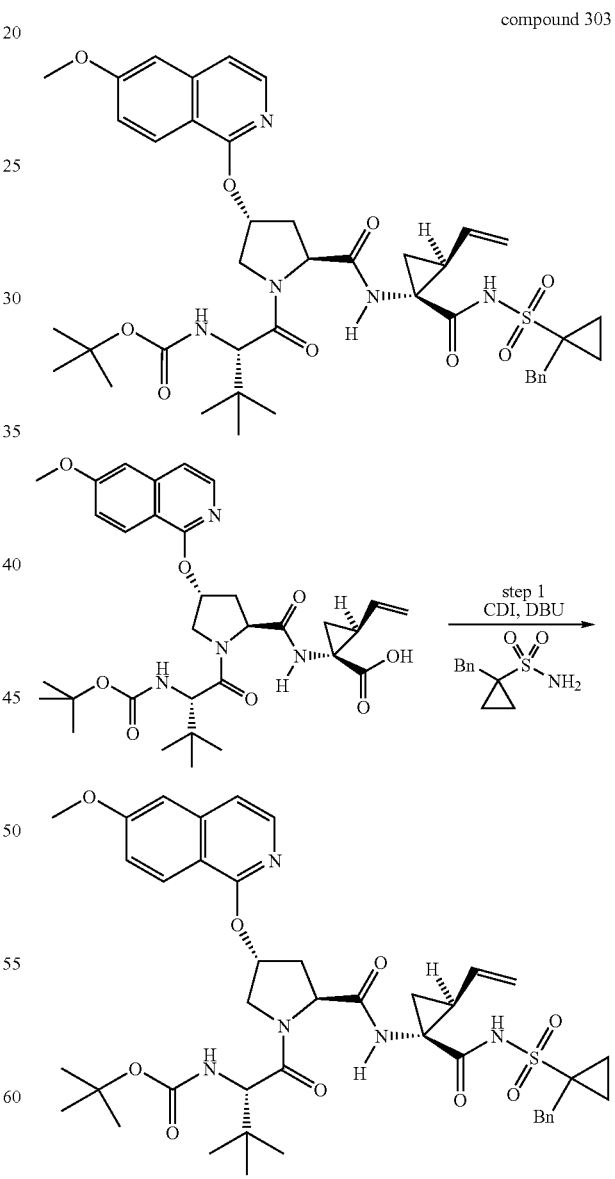

compound 303

Step 1:

Compound 303 was prepared in the same procedure as described in Step 3 of Example 300 in preparation of Compound 300 instead of 1-benzyl-cyclopropanesulfonamide (0.055 g, 0.26 mmol), was used in the place of 1-ethyl-cyclopropanesulfonamide, and purified by Prep-HPLC (solvent B: 50% to 100%) as a white foam (0.070 g). $^1$H NMR (500 MHz, Solvent: methanol-$d_4$) δ ppm 0.63 (m, 2H), 0.96 (s, 9H), 1.27 (s, 9H), 1.44 (m, 3H), 1.91 (m, 1H), 2.25 (m, 2H), 2.62 (dd, J=13.43, 7.02 Hz, 1H), 3.28 (d, J=13.73 Hz, 1H), 3.34 (m, 1H), 3.91 (s, 3H), 4.04 (m, 1H), 4.23 (s, 1H), 4.43 (d, J=11.90 Hz, 1H), 4.56 (m, 1H), 5.17 (d, J=10.07 Hz, 1H), 5.34 (d, J=17.09 Hz, 1H), 5.77 (m, 2H), 7.08 (d, J=8.85 Hz, 1H), 7.15 (m, 3H), 7.26 (m, 4H), 7.87 (d, J=6.10 Hz, 1H), 8.09 (d, J=8.85 Hz, 1H); LC-MS (Retention time: 2.03 method A), MS m/z 804 (M$^+$+1).

Example 304

Preparation of Compound 304; {1-[2-[1-(1-Chloro-cyclo-propanesulfonylaminocarbonyl)-2-vinyl-cyclopropylcarbamoyl]-4-(6-methoxy-isoquinolin-1-yloxy)-pyrrolidine-1-carbonyl]-2,2-dimethyl-propyl}-carbamic acid tert-butyl ester compound 304

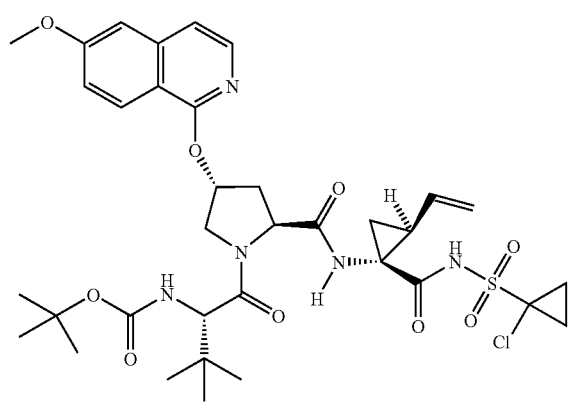

Scheme 1

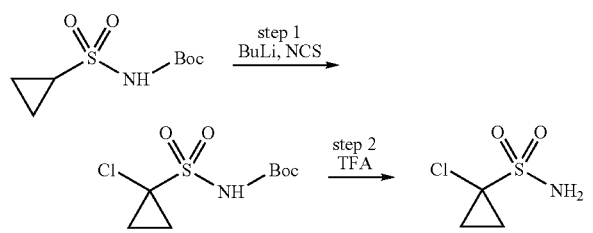

Step 1:

To a solution of cyclopropylsulfonylamine tert-butyl carbamate (1.0 g, 4.52 mmol) dissolved in THF (10 mL) cooled to −78° C., was added n-BuLi (6.4 mL, 10.2 mmol, 1.6 M in hexane) and the reaction mixture was stirred for 1 h. To this solution was added a THF (10 mL) solution of NCS (0.86 g, 6.34 mmol). After stirred for 5 min, the bath was changed to ice bath and the reaction mixture was stirred for 3 hrs at the temperature. The reaction mixture was diluted with ice water, the pH was adjusted to <4. The aqueous mixtire was extracted with EtOAc. The combined extracts were dried (MgSO$_4$), concentrated and purified by flash chromatography over SiO$_2$ using 0% to 60% EtOAc in hexanes as the eluent to afford 0.98 g (67%) of 1-chloro-cyclopropane-sulfonamide-tert-butylcarbamate as a white solid: $^1$H NMR (500 MHz, CDCl$_3$) δ ppm 1.51 (m, 11H), 2.01 (m, 2H), 7.60 (s, 1H).

Step 2:

A mixture of cyclopropylsulfonylamine tert-butyl carbamate 0.148 g 0.58 mmol) and TFA (1 mL) was stirred for 2.5 h at rt. Removed the solvent in vacuo to provide the product yield (0.09 g, 100%) as a light brown solid: $^1$H NMR (500 MHz, Methanol-$d_4$) δ ppm 1.38 (m, 2H), 1.70 (m, 2H).

Scheme 2

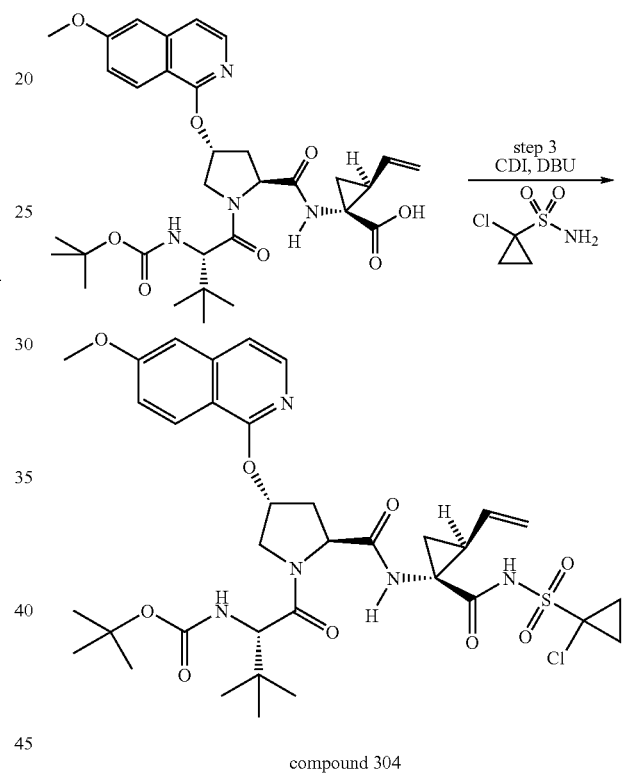

compound 304

Step 3:

A solution of the product (0.10 g, 0.16 mmol) of Step 2 of Example 300 in preparation of Compound 300 and CDI (0.037 mg, 0.229 mmol) in THF (2 mL) was heated at 70° C. for 60 min and allowed to cool down to rt. 1-Chlorocyclopropylsulfonamide (0.027 g, 0.14 mmol) and neat DBU (0.024 mL, 0.16 mmol) were added. The reaction mixture was stirred for overnite and directly purified by prep-HPLC to provided the product, Compound 304, (34.1 mg, %) as a light brown solid; $^1$H NMR (500 MHz, Solvent: methanol-$d_4$) δ ppm 1.03 (s, 9H), 1.27 (s, 9H), 1.46 (m, 3H), 1.86 (m, 1H), 1.98 (m, 2H), 2.29 (m, 2H), 2.61 (dd, J=13.73, 7.32 Hz, 1H), 3.92 (s, 3H), 4.05 (m, 1H), 4.24 (s, 1H), 4.55 (m, 1H), 5.13 (d, J=10.07 Hz, 1H), 5.29 (d, J=16.79 Hz, 1H), 5.70 (m, 1H), 5.82 (s, 1H), 7.08 (d, J=8.85 Hz, 1H), 7.17 (s, 1H), 7.24 (d, J=5.80 Hz, 1H), 7.88 (d, J=5.80 Hz, 1H), 8.09 (d, J=9.16 Hz, 1H); LC-MS (Retention time: 1.83 method B), MS m/z 748 (M$^+$+1).

Section E

Preparation of Compounds 400–401

Example 400

Preparation of Compound 400.

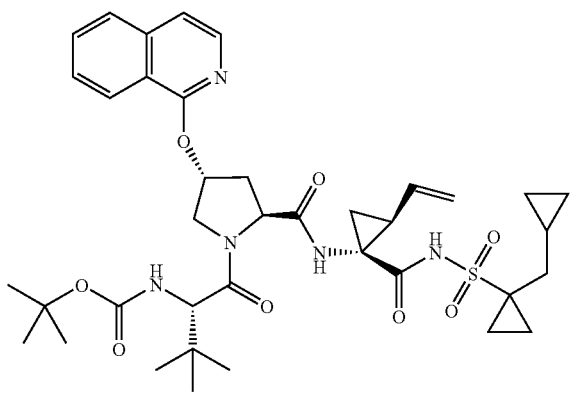

Compound 400

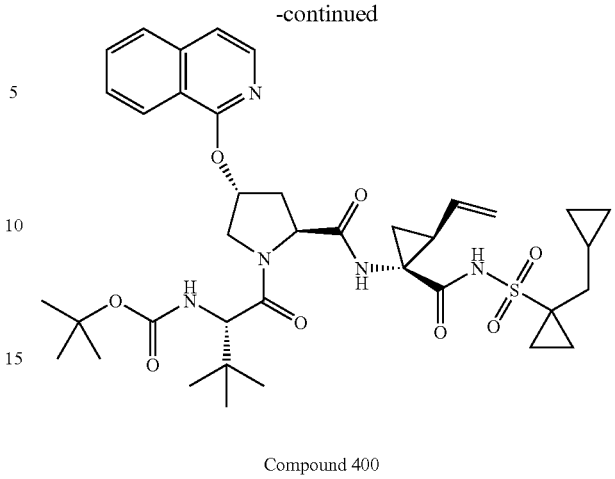

Compound 400

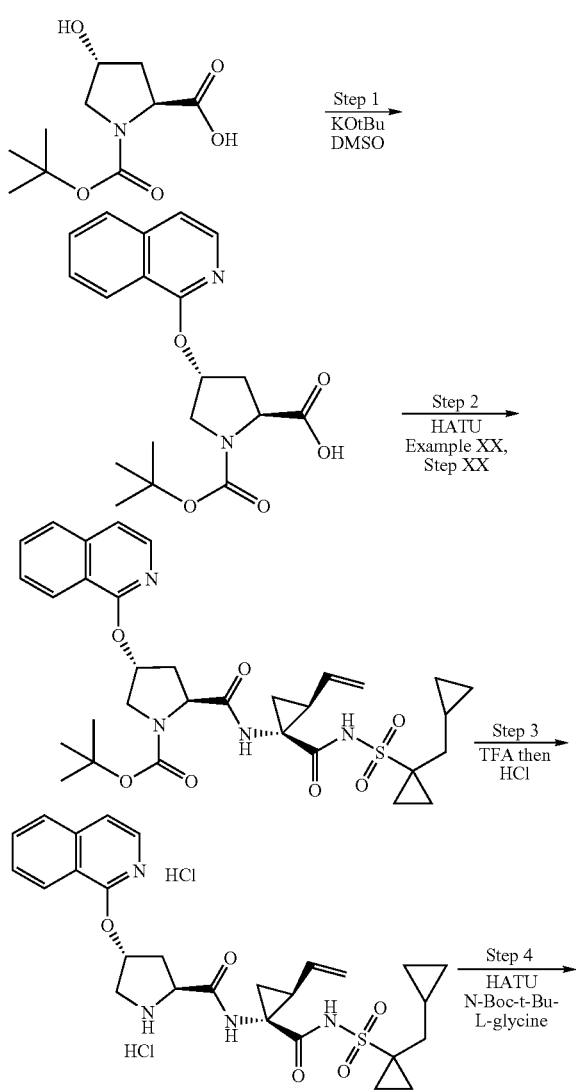

Scheme 1

Step 1:

To a solution of N-BOC-3-(R)-hydroxy-L-proline (231 mg, 1.0 mmol) in DMSO (10 mL) at the ambient temperature was added potassium tert-butoxide (336 mg, 3.0 mmol) in one portion. The formed suspension was stirred at this temperature for 30 min before being cooled to 10° C. 1-Chloro-isoquinoline (180 mg, 1.1 mmol) was added as solid in one portion and the final mixture was stirred at the ambient temperature for 12 h. Quenched with iced 5% citric acid (aq), extracted with EtOAC (100 mL). The aqueous phase was extracted with EtOAC again. The combined organic layers were washed with 5% citric acid (aq) and brine respectively, dried over MgSO$_4$, filtered. The filtrate was evaporated in vacuo to dryness to yield 329 mg (92%) of the desired product as an off-white foam. This material was used in the next step reaction as crude without further purification.

$^1$H NMR (CD$_3$OD) δ 1.42, 1.44 (rotamers, 9H), 2.39–2.44 (m, 1H), 2.68–2.72 (m, 1H), 3.80–3.87 (m, 2H), 4.44–4.52 (m, 1H), 5.78 (b, 1H), 7.32–7.33 (m, 1H), 7.58 (t, J=7.8 Hz, 1H),), 7.71 (t, J=7.5 Hz, 1H), 7.81 (d, J=8.0 Hz, 1H), 7.95 (d, J=6.0 Hz, 1H), 8.19 (d, J=8.0 Hz, 1H);

LC-MS (retention time: 1.61 min, method B), MS m/z 359 (M$^+$+H).

Step 2:

To a mixture of the product of Example 400, Step 1 (114 mg, 0.32 mmol), HATU (253 mg, 0.67 mmol), and the product of Example XX, Step XX (107 mg, 0.33 mmol) in CH$_2$Cl$_2$ (5 mL) was added DIPEA (129 mg, 1.0 mmol) at 0° C. After stirring at the ambient temperature for 12 h, the formed solution was diluted with CH$_2$Cl$_2$ (5 mL), washed with iced 5% citric acid (aq). The organic layer was washed with 5% citric acid (aq) and brine respectively, dried over MgSO$_4$, and filtered. The filtrate was evaporated in vacuo to dryness. The residue was purified by prep-HPLC to yield 86 mg (43%) of the desired product as a foam.

$^1$H NMR (CD$_3$OD) δ 0.09–0.10 (m 2H), 0.46–0.47 (m, 2H), 0.69–0.70 (m, 1H), 1.13–1.17 (m, 2H), 1.46 (s, 9H), 1.52–1.54 (m, 2H), 1.83–1.89 (m, 2H), 2.21–2.33 (m, 2H), 2.54–2.58 (m, 1H), 3.83–3.89 (m, 2H), 4.41–4.43 (m, 1H), 5.12 (d, J=10.5 Hz, 1H), 5.31 (d, J=15.0 Hz, 1H), 5.73–5.78 (m, 1H), 5.81 (b, 1H), 7.33–7.34 (m, 1H), 7.59 (t, J=7.8 Hz, 1H), 7.73 (t, J=7.5 Hz, 1H), 7.83 (d, J=8.0 Hz, 1H), 7.96 (d, J=6.0 Hz, 1H), 8.19 (d, J=8.0 Hz, 1H), 9.16 (b, 1H);

LC-MS (retention time: 1.86 min, method B), MS m/z 625 (M$^+$+H).

Step 3:

A solution of the product of Example 400, Step 2 (77 mg, 0.12 mmol) in DCM (1 mL) and TFA (1 mL) was stirred at room temperature for 1.5 h. The volatiles were removed in vacuo and the residue suspended in 1N HCl in diethyl ether (5 mL) and concentrated in vacuo. This procedure was repeated once. The resulting mixture was triturated from pentane and filtered to give the desired compound as a hygroscopic, off-white solid (65 mg, 91%).

LC-MS (retention time: 1.35 min, method B), MS m/z 525 (M$^+$+H).

Step 4:

To a mixture of the product of Example 400, Step 3 (65 mg, 0.12 mmol), HATU (66 mg, 0.17 mmol), and N-Boc-t-Butyl-L-glycine (32 mg, 0.14 mmol) in CH$_2$Cl$_2$ (2 mL) was added DIPEA (39 mg, 0.35 mmol) at 0° C. After stirring at the ambient temperature for 12 h, the formed solution was diluted with CH$_2$Cl$_2$ (5 mL), washed with iced 5% citric acid (aq). The organic layer was washed with 5% citric acid (aq) and brine respectively, dried over MgSO$_4$, and filtered. The filtrate was evaporated in vacuo to dryness. The residue was purified by prep-HPLC to yield 45 mg (53%) of Compound 400 as a white solid.

$^1$H NMR (CD$_3$OD) δ 0.04–0.12 (m 2H), 0.44–0.48 (m, 2H), 0.67–0.70 (m, 1H), 1.04 (s, 9H), 1.13–1.18 (m, 2H), 1.24 (s, 9H), 1.49–1.58 (m, 3H), 1.76–1.95 (m, 3H), 2.21–2.31 (m, 2H), 2.61–2.65 (m, 1H), 4.07–4.10 (m, 1H), 4.26–4.27 (m, 1H), 4.46–4.48 (m, 1H), 4.54–4.56 (m, 1H), 5.11 (d, J=10 Hz, 1H), 5.26 (d, J=20 Hz, 1H), 5.69–5.78 (m, 1H), 5.88 (b, 1H), 6.66–6.68 (b, 1H), 7.32–7.33 (m, 1H), 7.52 (t, J=7.8 Hz, 1H), 7.70 (t, J=7.5 Hz, 1H), 7.80 (d, J=8.0 Hz, 1H), 7.96 (d, J=6.0 Hz, 1H), 8.20 (d, J=8.0 Hz, 1H);

LC-MS (retention time: 1.92 min, method B), MS m/z 738 (M$^+$+H).

Example 401

Preparation of Compound 401.

Compound 401

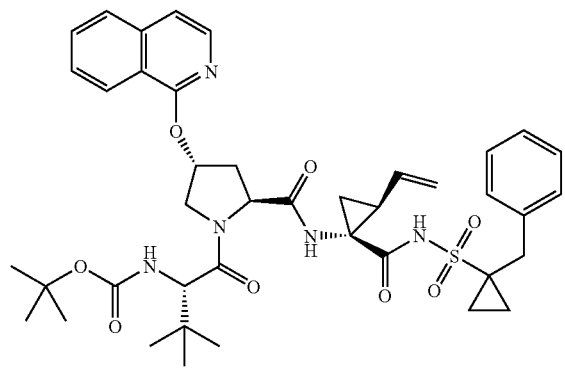

Scheme 2

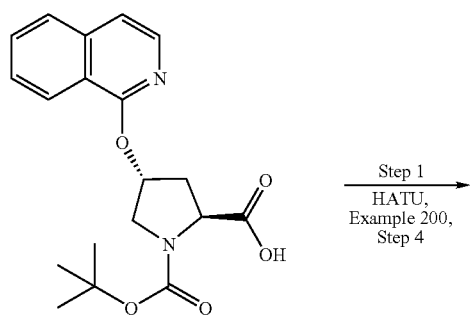

Step 1
HATU,
Example 200,
Step 4

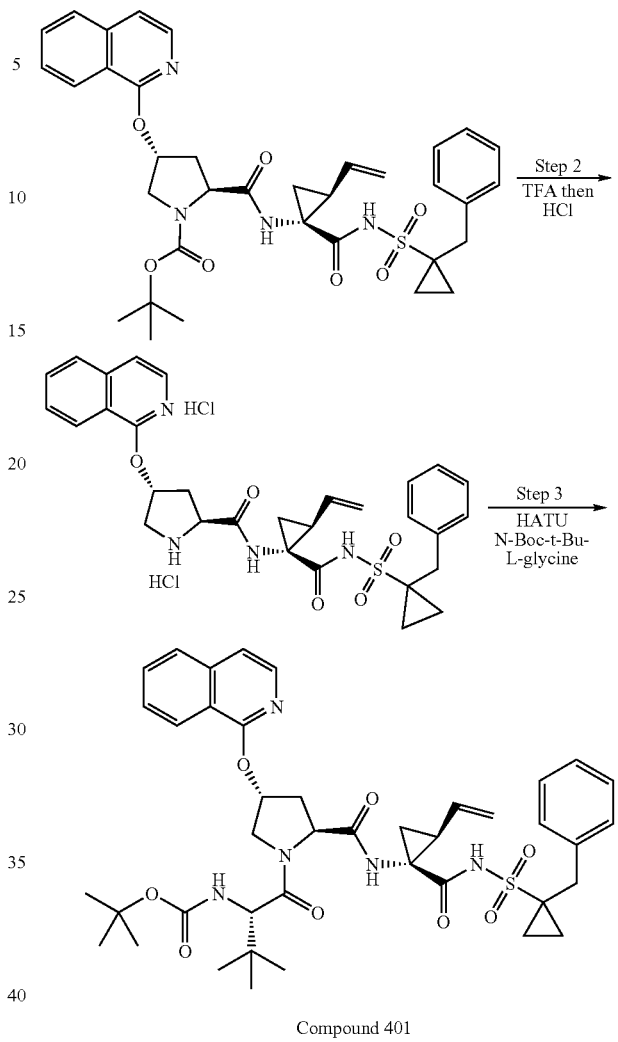

Step 2
TFA then
HCl

Step 3
HATU
N-Boc-t-Bu-L-glycine

Compound 401

Step 1:

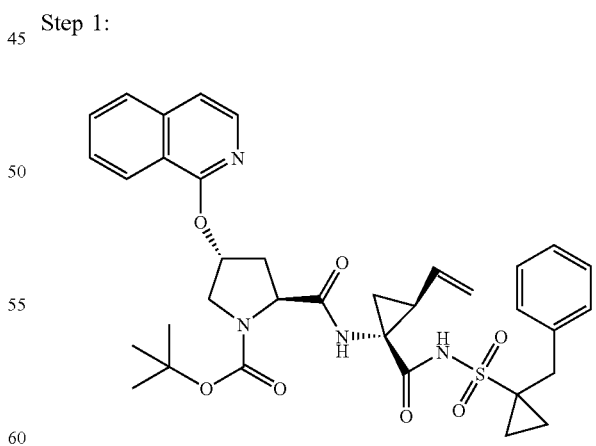

This product was prepared by the same procedure as described in Example 400, Step 2, except using the product of Example 200, Step 4 instead.

LC-MS (retention time: 1.66 min, method B), MS m/z 661 (M$^+$+H).

Step 2:

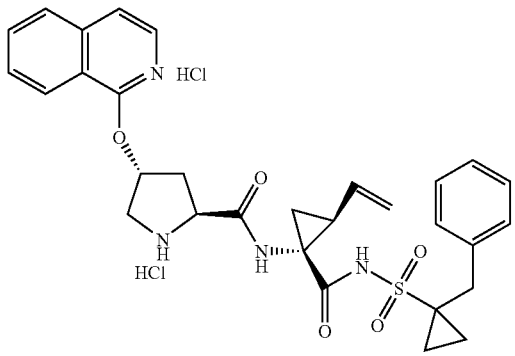

This product was prepared by the same procedure as described in Example 400, Step 3, except using the product of Example 401, Step 1 instead.

LC-MS (retention time: 1.21 min, method B), MS m/z 561 (M$^+$+H).

Step 3:

Compound 401 was prepared by the same procedure as described in Example 400, Step 4, except using the product of Example 401, Step 2 instead.

$^1$H NMR (CD$_3$OD) δ 0.61–0.67 (m, 2H), 0.96 (s, 9H), 0.99–1.02 (m, 2H), 1.25 (s, 9H), 1.44–1.48 (m, 3H), 1.90–1.94 (m, 1H), 2.25–2.30 (m, 2H), 2.62–2.69 (m, 1H), 4.04–4.10 (m, 1H), 4.24 (b, 1H), 4.46–4.50 (m, 1H), 4.54–4.58 (m, 1H), 5.18 (d, J=10 Hz, 1H), 5.34 (d, J=15 Hz, 1H), 5.76–5.81 (m, 1H), 5.86 (b, 1H), 7.13–7.26 (m, 2H), 7.25–7.30 (m, 4H), 7.32 (t, J=7.8 Hz, 1H), 7.79 (t, J=7.5 Hz, 1H), 7.80 (d, J=8.0 Hz, 1H), 7.96 (d, J=6.0 Hz, 1H), 8.21 (d, J=8.0 Hz, 1H), 9.08 (b, 1H);

LC-MS (retention time: 2.03 min, method B), MS m/z 774 (M$^+$+H).

Section F

Preparation of Compounds 500–502

Example 500

Preparation of Compound 500.

Compound 500

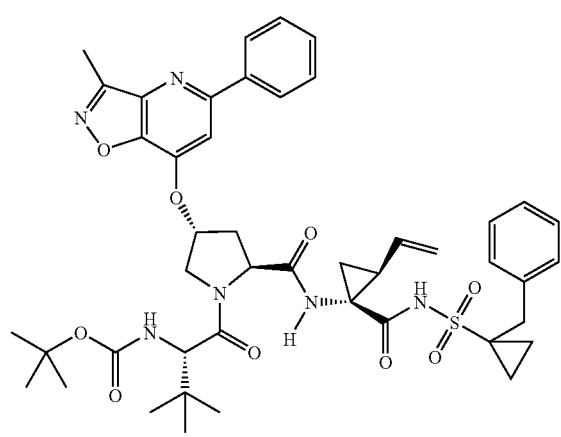

-continued

Scheme 1

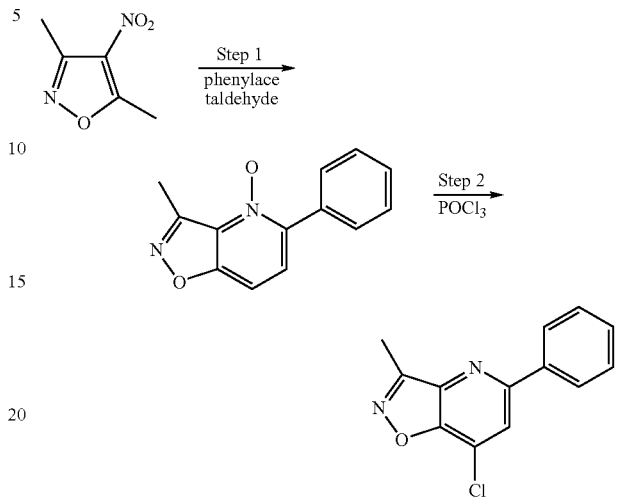

Step 1:

A mixture of 3,5-dimethyl-4-nitro-isoxazole (1.42 g, 10.0 mmol), phenylacetaldehyde (1.32 g, 1.0 mmol) in piperidine (1 mL) and ethanol (10 mL) was heated to reflux for 16 h. After cooling down to the ambient temperature, the product precipitated out was collected by filtration. The cake was washed with cold ethanol thoroughly to afford 1.20 g (53%) of the desired product as a white solid.

$^1$H NMR (CDCl$_3$) δ 2.87 (s, 3H), 7.46–7.50 (m, 3H), 7.56 (d, J=8.5 Hz, 1H), 7.7–7.80 (m, 2H);

LC-MS (retention time: 1.19 min, method B), MS m/z 227 (M$^+$+H).

Step 2:

A solution of 3-methyl-5-phenyl-isoxazolo[4,5-b]pyridine 4-oxide (1.00 g, 4.40 mmol) and POCl$_3$ (2.71 g, 17.7 mmol) in chloroform (10 mL) was heated to reflux for 1 h. After cooling down to the ambient temperature, the final solution was diluted with chloroform (50 mL) and washed with NaHCO$_3$ (aq.) (two 50 mL portions) and brine, dried over MgSO$_4$, filtered, evaporated. The residue was purified by flash chromatography (4:1 hexane-EtOAc) to afford 790 mg (73%) of the desired product as a white solid.

$^1$H NMR (CDCl$_3$) δ 2.72 (s, 3H), 7.46–7.54 (m, 3H), 7.91 (s, 1H), 8.00–8.03 (m, 2H);

LC-MS (retention time: 1.76 min, method B), MS m/z 245, 247 (M$^+$+H).

Scheme 2

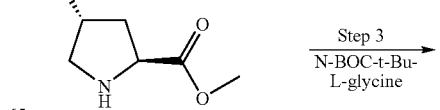

Step 3
N-BOC-t-Bu-
L-glycine

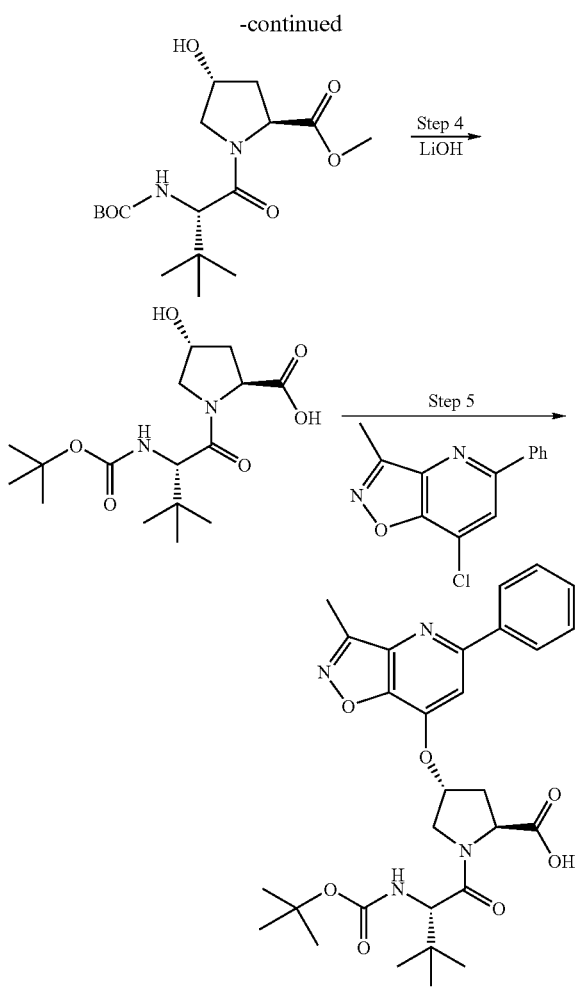

Step 3:

To a mixture of 4-hydroxy-pyrrolidine-2-carboxylic acid methyl ester (H-Hyp-OMe HCl) (1.81 g, 10.0 mmol), HATU (5.70 g, 15.0 mmol), and N-BOC-t-butyl-L-glycine (2.42 g, 10.5 mmol) in $CH_2Cl_2$ (100 mL) was added DIPEA (3.47 g, 31.0 mmol) at 0° C. After stirring at the ambient temperature for 12 h, the formed solution was diluted with $CH_2Cl_2$ (100 mL), washed with iced 5% citric acid (aq). The organic layer was washed with 5% citric acid, 1M NaOH, brine respectively, dried over $MgSO_4$, and filtered. The filtrate was evaporated in vacuo to provide 3.55 g (99%) of the desired product as an off-white foam. This product was used for the next reaction as crude without further purification.

$^1$H NMR ($CD_3OD$) δ 1.04 (s, 9H), 1.43 (s, 9H), 1.99–2.03 (m, 1H), 2.20–2.30 (m, 1H), 3.69 (s, 3H), 3.70–3.79 (m, 2H), 4.28 (b, 1H), 4.46 (b, 1H), 4.74–4.80 (m, 1H);

LC-MS (retention time: 1.28 min, method B), MS m/z 359 ($M^+$+H).

Step 4:

A mixture of the product of Example 500, Step 3 (3.55 g, 9.9 mmol) in THF (50 mL), MeOH (50 mL) and LiOH monohydrate (0.83 g, 19.9 mmol in 50 mL $H_2O$) was stirred at the ambient temperature over night. After removal of the volatiles in vacuo, the residue was dissolved in 0.1 M NaOH (100 mL). This aqueous solution was washed with ether (50 mL), acidified by 1M HCl to pH4. Extracted with EtOAc (100 mL). The organic layer was washed with 5% citric acid and brine, dried over $MgSO_4$, evaporated to dryness to give 3.20 g (95%) of the desired product as a white foam. This product was used as crude without further purification.

$^1$H NMR ($CD_3OD$) δ 1.02 (s, 9H), 1.43 (s, 9H), 2.01–2.09 (m, 1H), 2.25–2.32 (m, 1H), 3.70–3.85 (m, 2H), 4.26–4.30 (m, 1H), 4.46–4.51 (m, 2H), 6.37–6.41 (m, 1H);

LC-MS (retention time: 1.14 min, method B), MS m/z 345 ($M^+$+H).

Step 5:

To a solution of the product of Example 500, Step 4 (1.01 g, 2.93 mmol) in DMSO (30 mL) was added potassium tert-butoxide (1.02 g, 9.08 mmol). The formed solution was stirred at the ambient temperature for 1 h before addition of 7-chloro-3-methyl-5-phenyl-isoxazolo[4,5-b]pyridine (0.75 g, 3.08 mmol). The final solution was stirred for 12 h. Then was quenched with iced water, acidified with 1M HCl to pH 4, extracted with EtOAc (two 200 mL portions). The organic layers were washed with brine, dried over $MgSO_4$, filtered, evaporated. The residue was purified by prep-HPLC (60% B-100% B, 15 min gradient) to afford 305 mg (19%) of the desired product as a pale yellow solid.

$^1$H NMR ($CD_3OD$) δ 1.02 (s, 9H), 1.17 (s, 9H), 2.37–2.47 (m, 1H), 2.64 (s, 3H), 2.85–2.93 (m, 1H), 4.00–4.08 (m, 1H), 4.14 (b, 1H), 4.49–4.55 (m, 1H), 4.62–4.71 (m, 1H), 5.70 (m, 1H), 7.45–7.53 (m, 3H), 7.56 (s, 1H), 8.03–8.06 (m, 2H);

LC-MS (retention time: 1.89 min, method B), MS m/z 553 ($M^+$+H).

Scheme 3

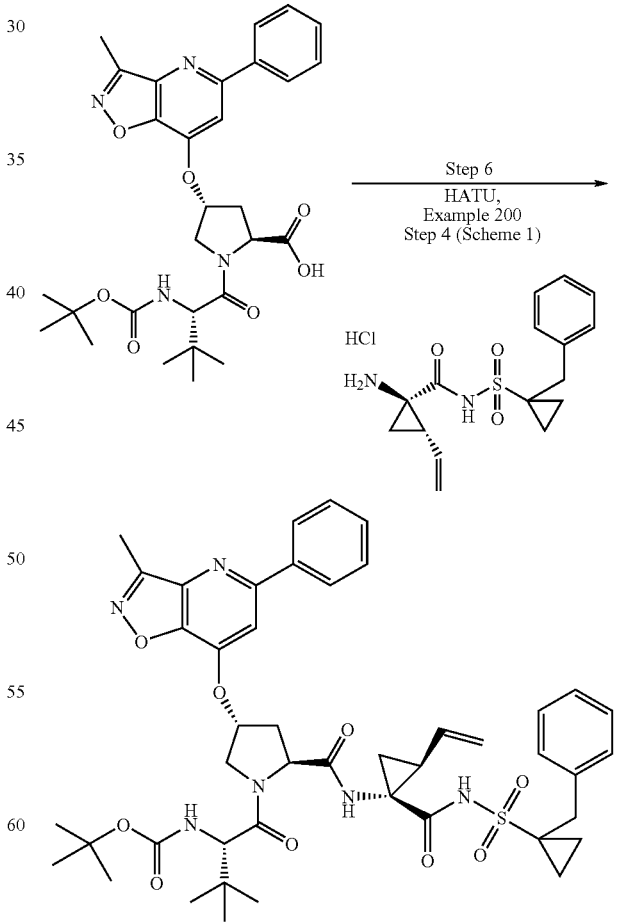

Compound 500

Step 6:

To a mixture of the product of Example 500, Step 5 (82 mg, 0.15 mmol), HATU (84 mg, 0.22 mmol), and the product of Example 200, Step 4 (58 mg, 0.16 mmol) in CH$_2$Cl$_2$ (5 mL) was added DIPEA (50 mg, 0.44 mmol) at 0° C. After stirring at the ambient temperature for 12 h, the formed solution was diluted with CH$_2$Cl$_2$ (15 mL), washed with iced 5% citric acid (aq). The organic layer was washed with 5% citric acid (aq) and brine respectively, dried over MgSO$_4$, and filtered. The filtrate was evaporated in vacuo to dryness. The residue was purified by prep-HPLC to yield 42 mg (33%) of Compound 500 as an off-white solid.

$^1$H NMR (CD$_3$OD) δ 0.62–0.67 (m, 2H), 0.95 (s, 9H), 0.99–1.02 (m, 2H), 1.19 (s, 9H), 1.44–1.47 (m, 3H), 1.91–1.94 (m, 1H), 2.27–2.37 (m, 2H), 2.62–2.68 (m, 4H), 4.08–4.10 (m, 1H), 4.17 (b, 1H), 4.49–4.51 (m, 1H), 4.57–4.60 (m, 1H), 5.19 (d, J=10 Hz, 1H), 5.36 (d, J=20 Hz, 1H), 5.70 (b, 1H), 5.77–5.83 (m, 1H), 7.14–7.15 (m, 2H), 7.24–7.31 (m, 3H), 7.47–7.50 (m, 3H), 7.57 (s, 1H), 8.04–8.06 (m, 2H), 9.16 (b, 1H);

LC-MS (retention time: 2.06 min, method B), MS m/z 855 (M$^+$+H).

Example 501

Preparation of Compound 501.

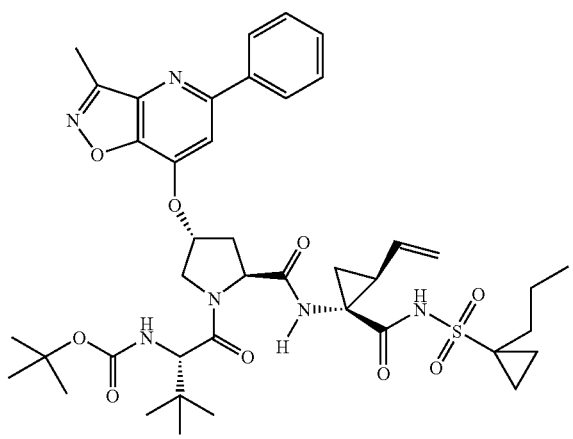

Compound 501

Scheme 1

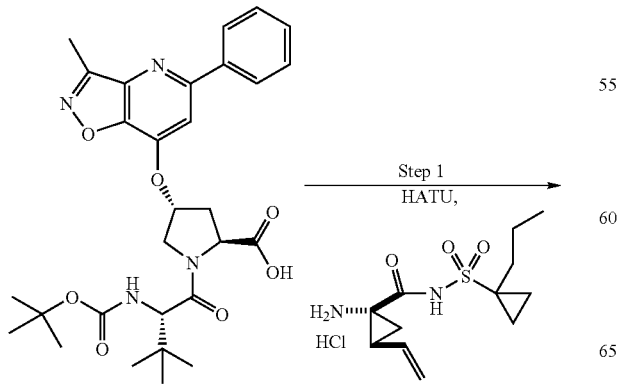

Step 1
HATU,

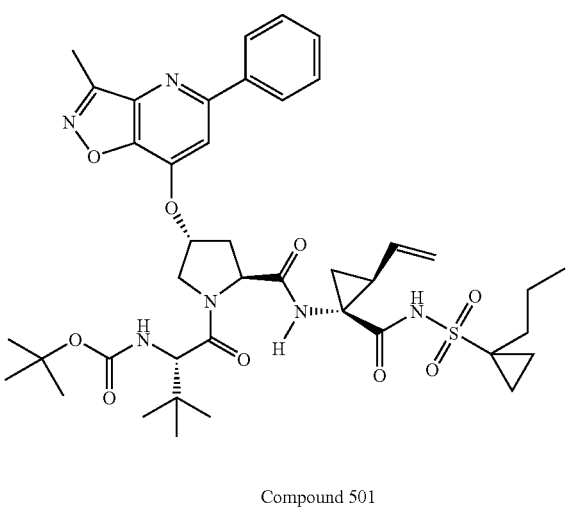

Compound 501

Compound 501 was prepared by the same procedure as described in Example 500, Step 6.

$^1$H NMR (CD$_3$OD) δ 0.90–0.92 (m, 5H), 1.02 (s, 9H), 1.21 (s, 9H), 1.43–1.47 (m, 4H), 1.58–1.61 (m, 1H), 1.70–1.76 (m, 1H), 1.84–1.92 (m, 2H), 2.22–2.27 (m, 1H), 2.32–2.38 (m, 1H), 2.62–2.68 (m, 4H), 4.10–4.12 (m, 1H), 4.19 (b, 1H), 4.47–4.50 (m, 1H), 4.55–4.58 (m, 1H), 5.12 (d, J=15 Hz, 1H), 5.30 (d, J=20 Hz, 1H), 5.68–5.76 (m, 2H), 7.46–7.52 (m, 3H), 7.58 (s, 1H), 8.05–8.06 (m, 2H), 9.24 (b, 1H);

LC-MS (retention time: 2.02 min, method B), MS m/z 807 (M$^+$+H).

Example 502

Preparation of Compound 502.

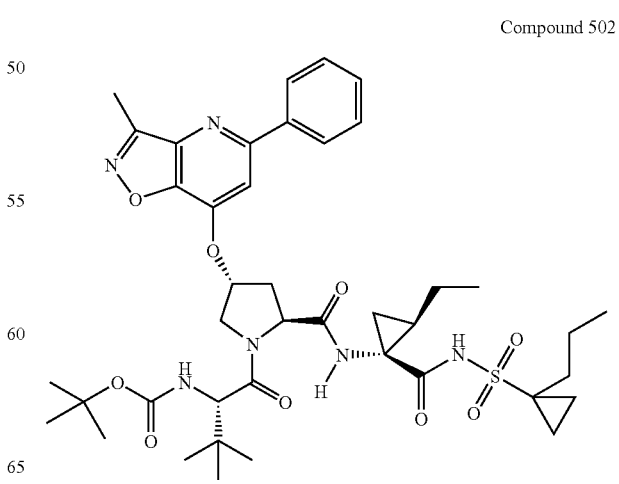

Compound 502

-continued
Scheme 1

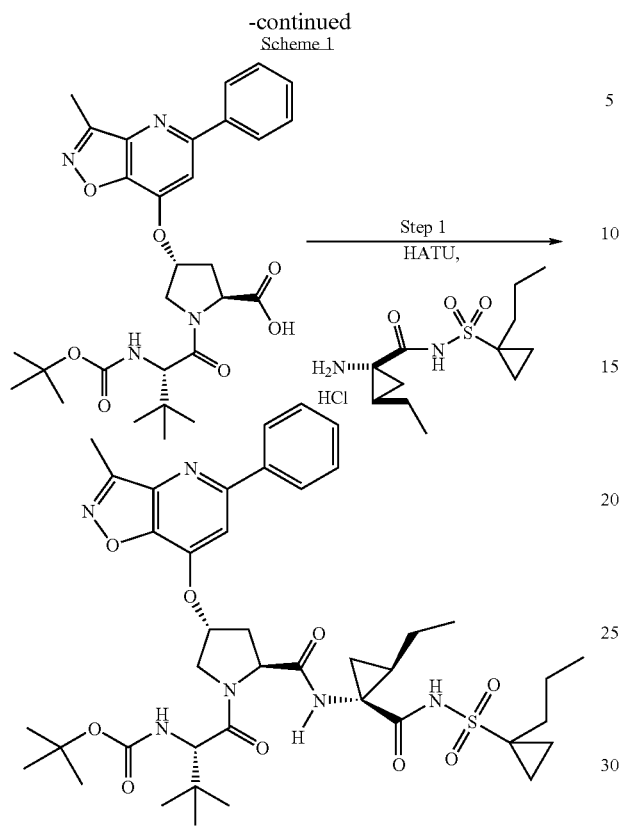

Compound 502

Compound 502 was prepared by the same procedure as described in Example 500, Step 6.

$^1$H NMR (CD$_3$OD) δ 0.90–1.00 (m, 9H), 1.02 (s, 9H), 1.20 (s, 9H), 1.41–1.58 (m, 6H), 1.71–1.78 (m, 1H), 1.91–2.00 (m, 1H), 2.34–2.39 (m, 1H), 2.62–2.64 (m, 4H), 4.11–4.16 (m, 1H), 4.19 (b, 1H), 4.47–4.59 (m, 2H), 5.71 (b, 1H), 7.46–7.51 (m, 3H), 7.57 (s, 1H), 8.04–8.06 (m, 2H); LC-MS (retention time: 1.96 min, method B), MS m/z 809 (M$^+$+H).

Section G
Preparation of Compounds 600–605

Example 600

Preparation of Compound 600

Compound 600

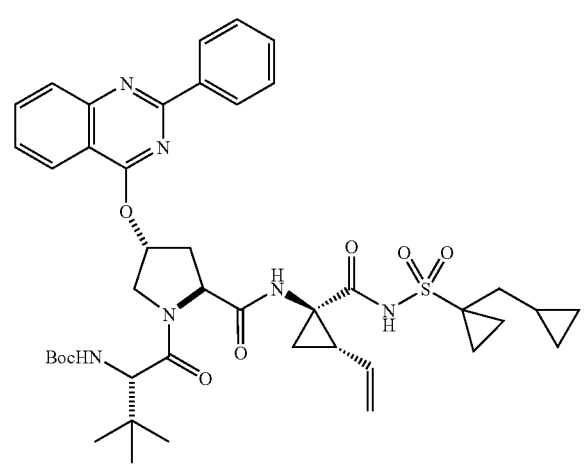

-continued
Scheme 1.

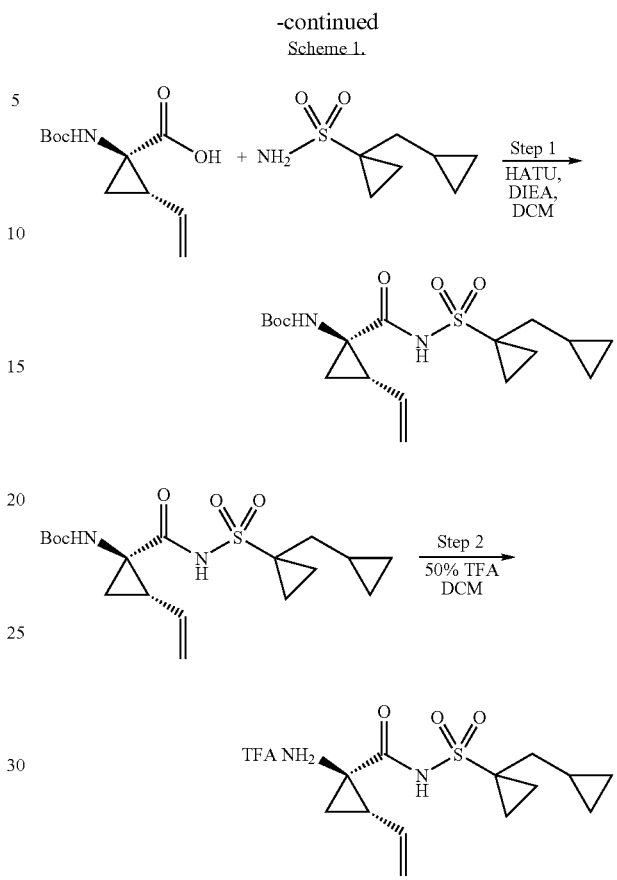

Step 1:

To a solution of 1R-tert-butoxycarbonylamino-2S-vinyl-cyclopropanecarboxylic acid (2.1 g, 9.24 mmol) in THF (26 mL) was added CDI (1.87 g, 11.6 mmol) and was heated to 78° C. for 45 min. After let cool to rt, the reaction mixture was treated with 1-cyclopropylmethyl-cyclopropanesulfonic acid amide (2.11 g, 12.01 mmol) and DBU (2.95 g, 19.4 mmol). After stirring at rt for 14 h, the reaction was diluted with EtOAc (50 mL) and washed with 4×50 mL 1N HCl. The combined aqueous layer was extracted with 3×50 mL EtOAc. The combined organic layer was with brine, dried over MgSO4 and concentrated to a light brown solid product (3.48 g, 98%). The product was used as crude. $^1$H NMR (500 MHz, CD$_3$OD) δ 0.07 (q, J=4.88 Hz, 2H) 0.44–0.48 (m, 2H) 0.68–0.72 (m, 1H) 1.14 (s, 2H) 1.28 (dd, J=9.46, 5.19 Hz, 1H) 1.43 (d, J=7.02 Hz, 1H) 1.46 (s, 9H) 1.49–1.53 (m, 2H) 1.81 (dd, J=7.78, 5.34 Hz, 1H) 1.86 (s, 2H) 2.16–2.20 (m, 1H) 5.08 (dd, J=10.38, 1.22 Hz, 1H) 5.27 (dd, J=17.24, 1.37 Hz, 1H) 5.51–5.55 (m, 1H).

Step 2:

To a solution of the product from step 1 of Example 600 (3.75 g, 9.75 mmol) in DCM (15 mL) was added TFA (15 mL) and was stirring rt for 20 min. Solvent was concentrated under vacuum to give viscous brown oil in quantitative yield. The product was used as crude: MS m/z 285 (MH$^+$).

Scheme 2

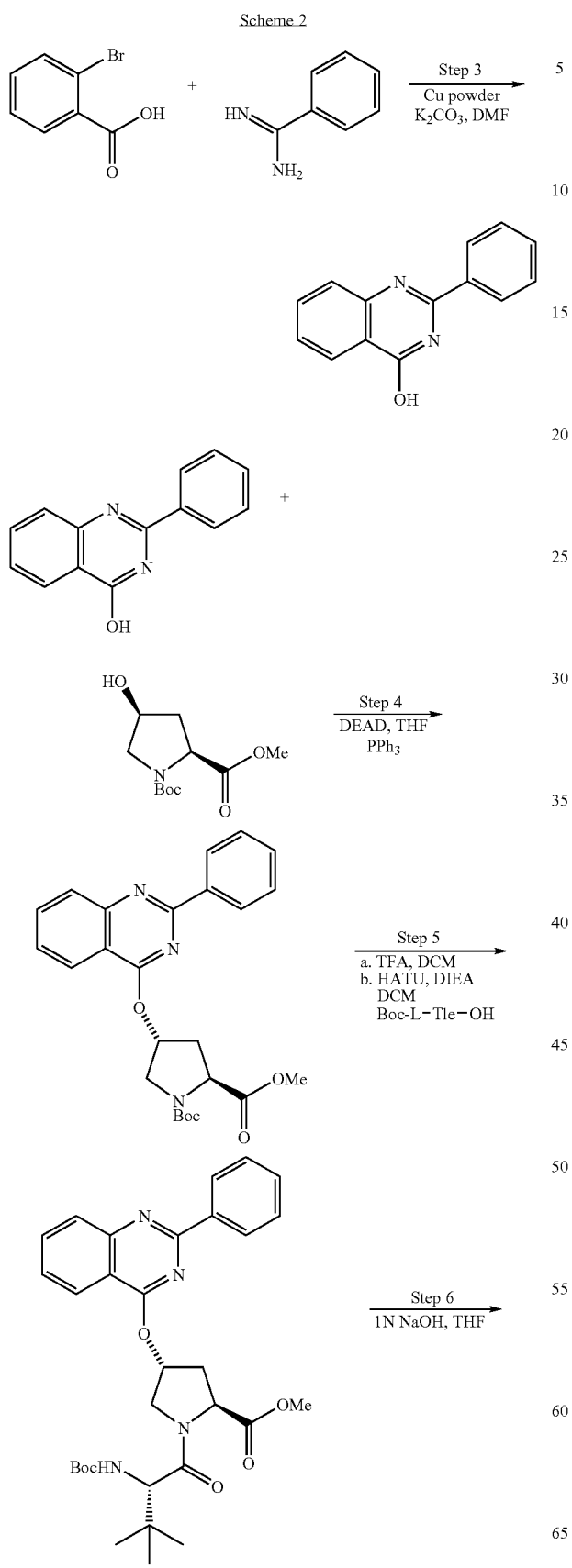

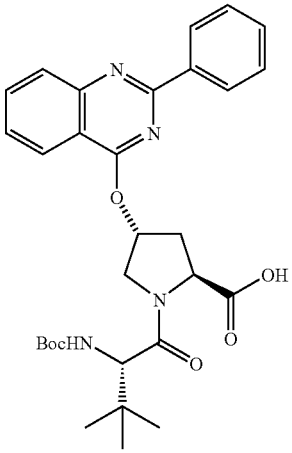

Step 3:

To a solution of 2-bromobenzoic acid (10 g, 49.75 mmol) in DMF (150 mL) in a medium pressure flask (Chemglass) was added benzamidine (8.6 g, 54.73 mmol), $K_2CO_3$ (20.6 g, 149.3 mmol), and copper powder (632 mg, 9.95 mmol). The reaction mixture was heated to 180° C. for 4 h. Copper and excess $K_2CO_3$ were removed by hot vacuum filtration through a celite pad and washed with hot MeOH. The filtrate was let cool to rt and the white pricipatation was obtained by vacuum fitration (7.5 g, 68% yield):

Step 4:

To a 0° C. slurry of Boc-cis-Hydroxyproline-OMe (5.0 g, 20.39 mmol) and the product from step 3 of Example 600 (4.53 g, 20.39 mmol) in THF (200 mL) was added $Ph_3P$ (6.42 g, 24.47 mmol) and diisopropyl azocarboxylate (4.95 g, 24.47 mmol) dropwise. After stirring at rt for 24 h, the reaction mixture was diluted with EtOAc (100 mL) washed with 2×50 mL of 10% aqueous $Na_2CO_3$, 2×50 mL $H_2O$. The aqueous layer was separated and back-extracted with 1×100 mL EtOAc. The combined organic layer was washed with brine, dried over $MgSO_4$ and concentrated to give a yellow viscous oil which was redissolved in minimal amount of EtOAc and hexanes to effect the precipitation of most of the $Ph_3PO$ by-product at 4° C. $Ph_3PO$ was removed by vacuum filtration and the liquid filtrate was concentrated. The resulting viscous oil was purified by a flash column chromatography ($SiO_2$, 4:1 hex:EtOAc) to give a white foam product (8.86 g, 97% yield):

Step 5:

a). The product from step 4 of Example 600 (4.05 g, 9.01 mmol) was dissolved in 50% TFA in DCM (45 mL) and stirred at rt for 20 min. The solvent was concentrated and the resulting brown viscous oil was dried in vacuo overnight. The product was used directly for the next reaction.

b) To a solution of the resulting brown viscous oil from step 5a of Example 600 (4.90 g, 7.39 mmol) and DIEA (3.83 g, 29.56 mmol) in DCM (50 mL) were added N-BOC L-tBuGly (1.88 g, 8.13 mmole), HATU (3.37 g, 8.87 mmol). After stirring at rt for 35 h, the reaction mixture was wahed with I N HCl (26 mL) and adjusted to pH=5 with saturated $NaHCO_3$. The aqueous layer was extracted with 3×50 mL DCM. The combined orgo layer was washed with saturated $NaHCO_3$ (50 mL), dried over MgSO4 and concentrated to give a viscous oil product. Pale yellow precipatation product (2.7 g, 65% yield) was obtained from a solution of 1:3 Et₂O:pentane.

Step 6:

To a solution of the product from step 5a of Example 600 (1.51 g, 2.68 mmol) in THF (20 mL) was added 1N NaOH (6.7 mL, 6.7 mmol). After stirring at rt for 24 h, the rection mixture was extracted with 1×25 ml Et₂O. The Et₂O layer was washed 2×5 mL H₂O. The combined aqueous layer was acidified with 1N HCl to pH=5 and extracted with 3×50 mL DCM. The combined DCM layer was dried over MgSO4, concentrated and and dried under vacuum to give a white solid product (1.2 g, 82% yield):

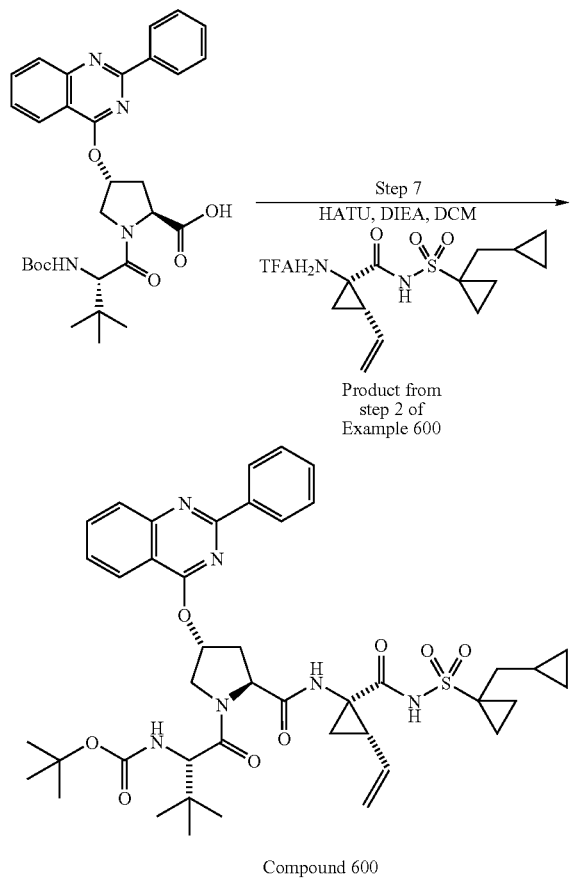

Scheme 3

Compound 600

Step 7:

To a solution of the product from step 6 of Example 600 (0.250 g, 0.456 mmol) and DIEA (0.177 g, 1.37 mmol) in DCM (5 mL) were added the product from step 2 of Example 600 (0.182 g, 0.456 mmol), HATU (0.225 g, 0.592 mmol). After stirring at rt for 14 h, the reaction mixture was wahed with 5% aqueous NaHCO₃ (5 mL), and 5% aqueous citric acid (5 mL). DCM (25 mL) was used to extrated the two aqueous layer, started with the NaHCO₃ layer. The combined orgo layer was dried over MgSO4 and concentrated to give a brown viscous oil which was purified by flash column chromatography to give a pale yellow solid nproduct (0.299 g, 80% yield): MS m/z 815 (MH⁺).

Example 601

Preparation of Compound 601

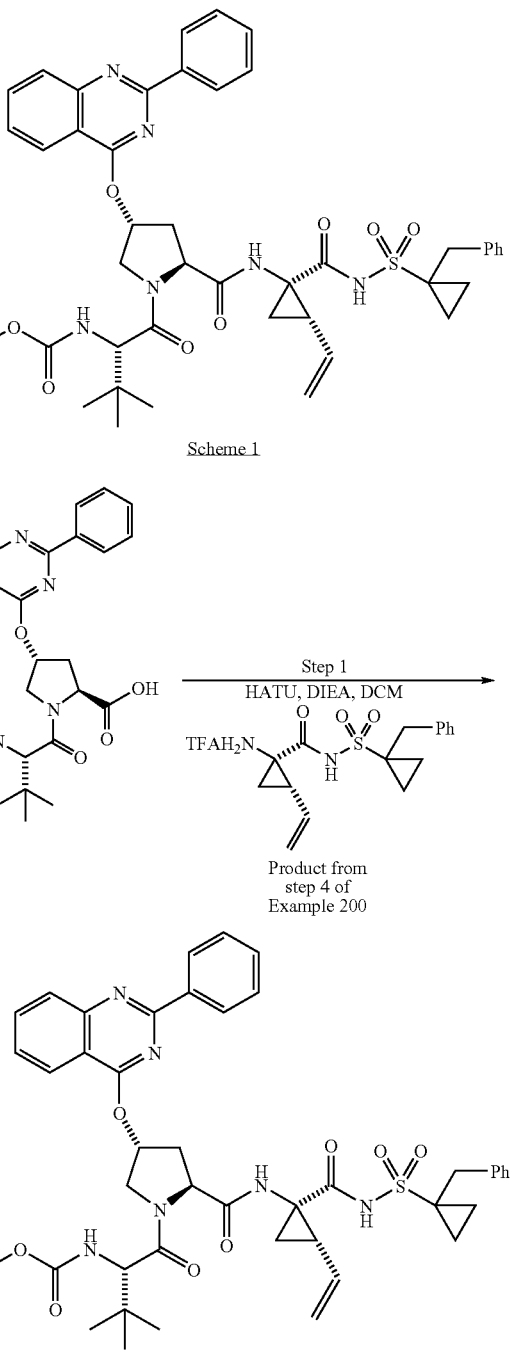

Scheme 1

Compound 601

Compound 601 was prepared by the same methods as Compound 600 with the following modifications:

Modifications: The product from step 4 of Example 200 was used as a starting material to give Compound 601 (0.309 g, 80% yield): MS m/z 851 (MH⁺).

Example 602
Preparation of Compound 602
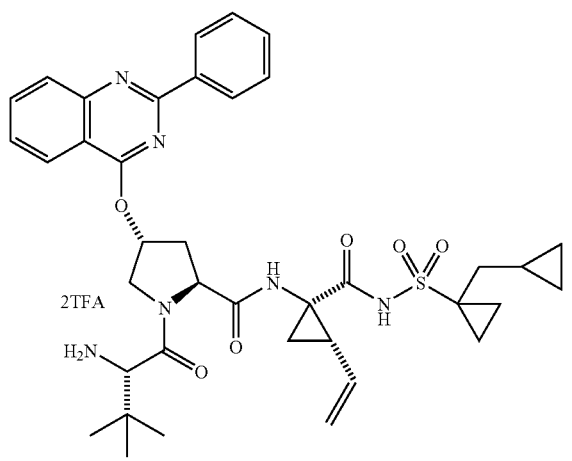
Compound 602
Scheme 1
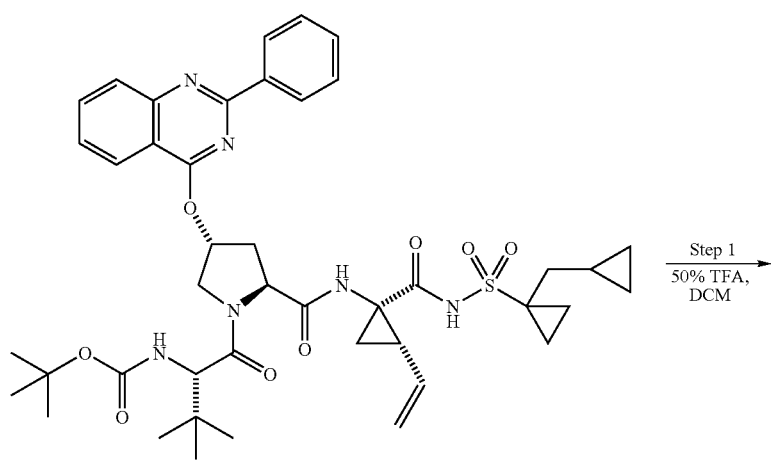
Compound 600
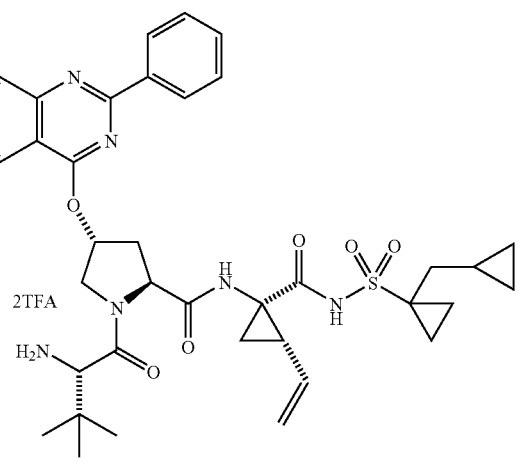
Compound 602

Step 1:
To a solution of Example 600 (0.245 g, 0.301 mmol) in DCM (1.5 mL) was added TFA (1.5 mL). After stirring rt for 15 min. reaction mixture was concentrated and dried under vacuum to give a light brow solid product (0.281 g, 99% yield). The product was used as crude: MS m/z 715 (MH$^+$).
Example 603
Preparation of Example 603
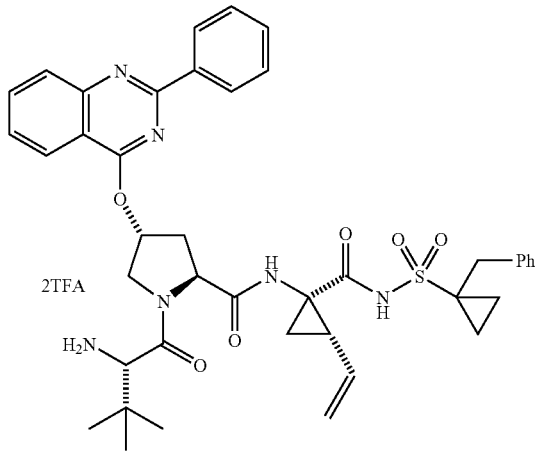
Compound 603
Scheme 1
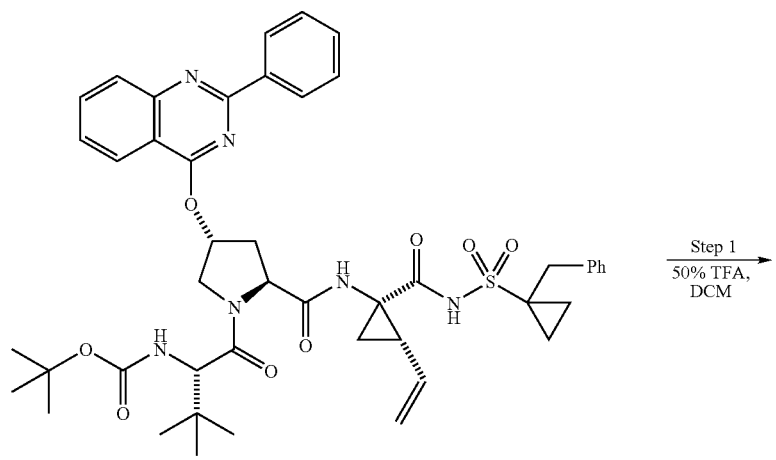
Compound 601
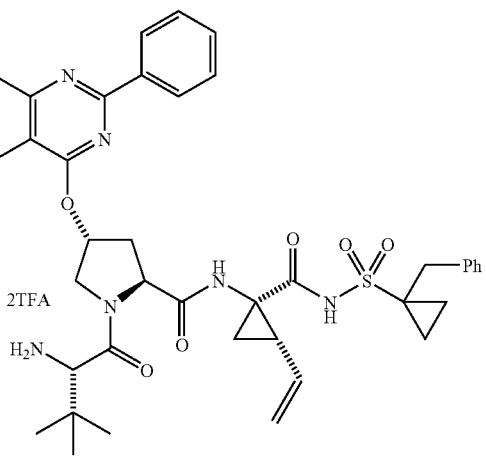
Compound 603

Compound 603 was prepared by the same methods as Compound 602 with the following modifications:
Modifications: Compound 601 was used as a starting material to give Compound 603 (0.290 g, quantatative yield): MS m/z 751 (MH$^+$).
Example 604
Preparation of Compound 604
Compound 604
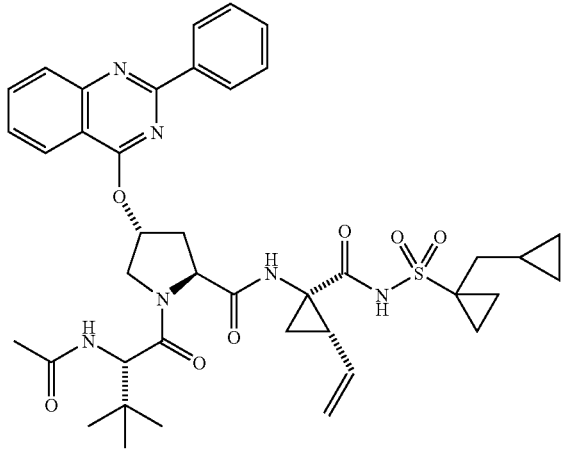
Scheme 1
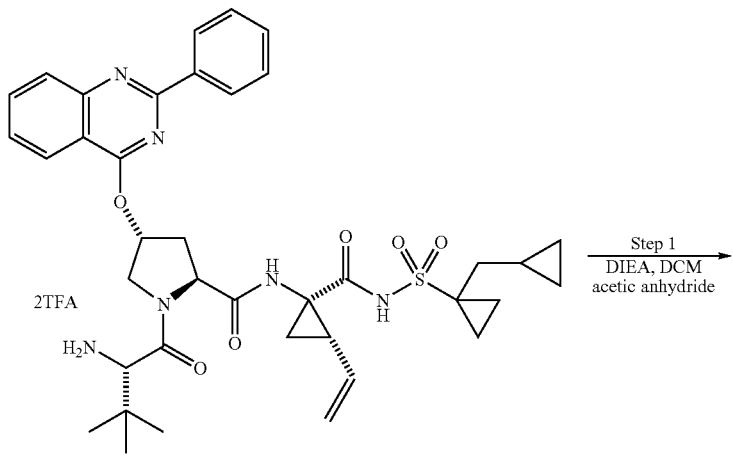
Compound 602
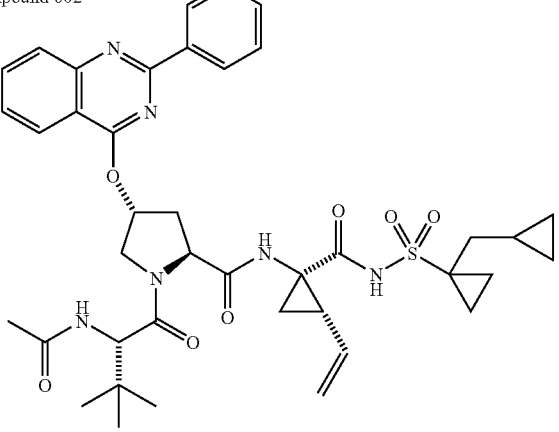
Compound 604

Step 1:
To a solution mixture of Compound 602 (50.0 mg, 0.053 mmol) and DIEA (28.0 mg, 0.212 mmol) in DCM (2 mL) was added acetic anhydride (21.7 mg, 0.212 mmol). After stirring at rt for 14 h, reaction was concentrated and purified by reversed phased prep-HPLC to give a white solid product (32.3 mg, 81% yield): MS m/z 757 (MH$^+$).
Example 605
Preparation of Compound 605
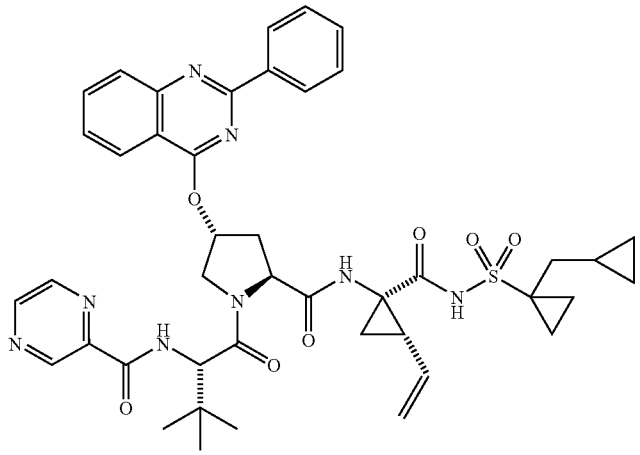
Compound 605
Scheme 1
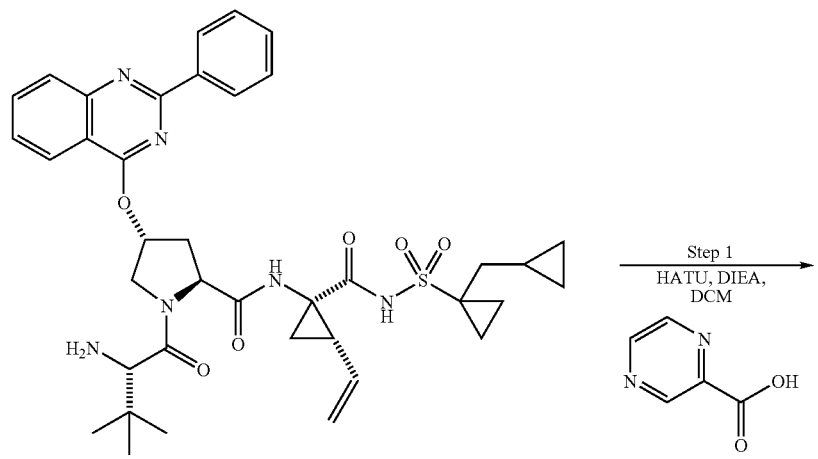
Compound 602
Step 1
HATU, DIEA,
DCM
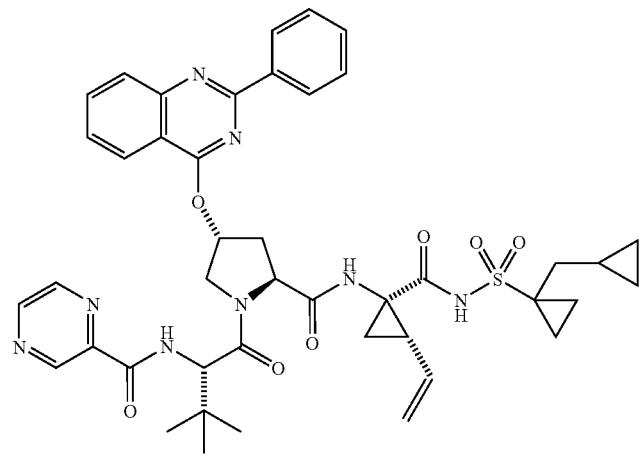
Compound 605

Compound 605 was prepared by the same methods as Compound 600 with the following modifications:

Modifications: Compound 602 and pyrazine-2-carboxylic acid were used as starting materials to give Compound 605 (38.2 m g, 88% yield): MS m/z 821 (MH$^+$).

Section H

Compounds 700–710

Compounds 700 ans 701 were prepared using the processes described herein. The preparation of the functionalized P2 Proline intermediate employed in the construction of Compound 700 and Compound 701 is described in CT-2723

Compound 700

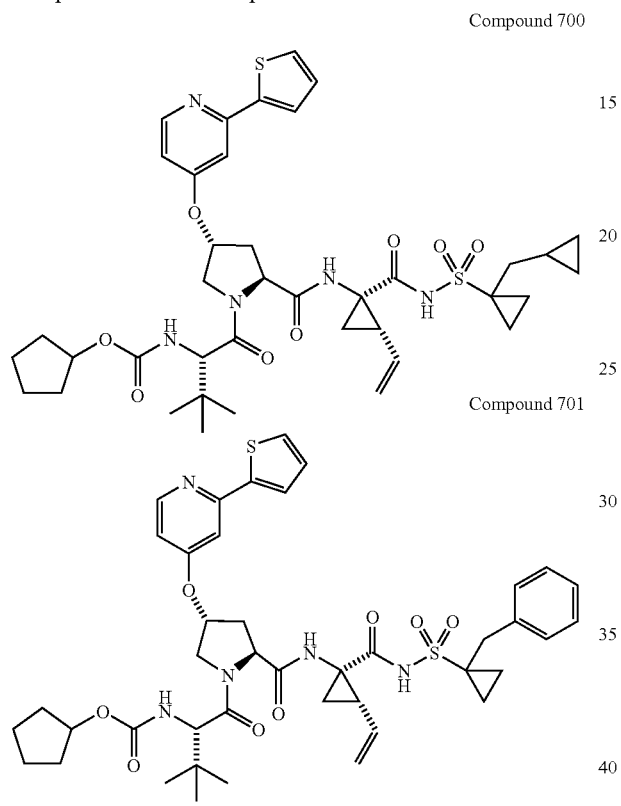

Compound 701

Section I

Preparation of Compound 800

Example 800

Preparation of Compound 800.

Compound 800

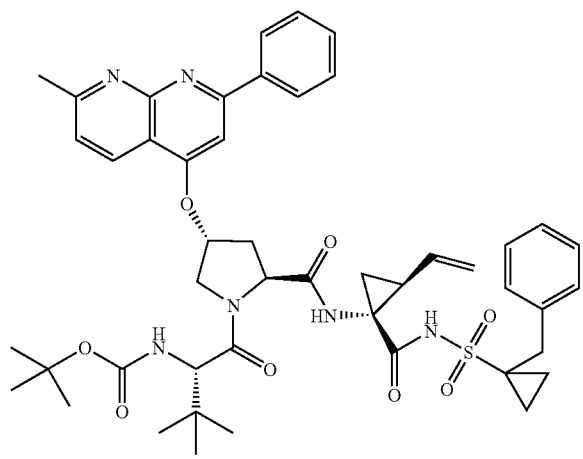

-continued

Scheme 1

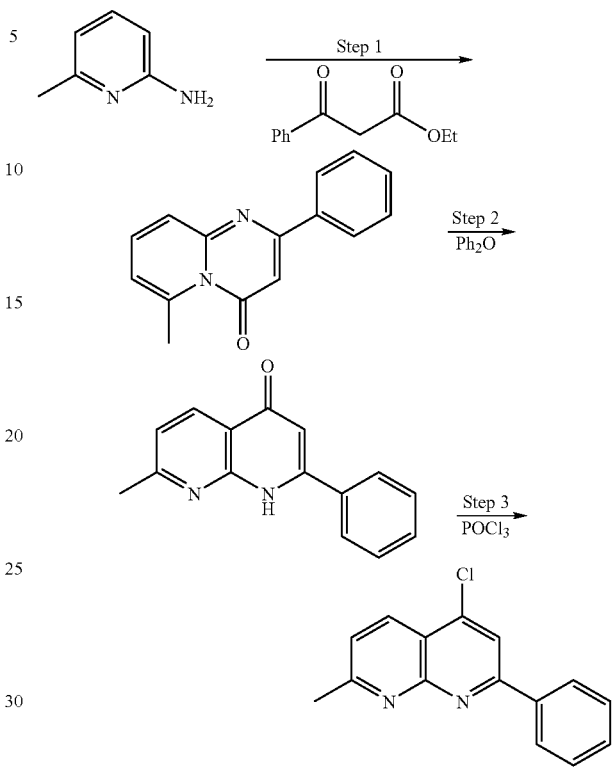

Step 1:

A mixture of 2-amino-6-methylpyridine (1.08 g, 10.0 mmol), ethyl benzoylacetate (2.30 g, 12.0 mmol) and polyphosphoric acid (6.00 g, 61.2 mmol) was heated to 110° C. for 5 h. After cooling to the ambient temperature, the mixture was poured into iced water (20 mL) and neutralized to pH 7 with 10 M NaOH. Extracted with CHCl$_3$. The organic layer was washed with brine, dried over MgSO$_4$, filtered, evaporated. The residue was purified by flash chromatography (1:1 hexane-EtOAc) to afford 510 mg (22%) of the desired product as a pale yellow solid.

$^1$H NMR (CDCl$_3$) δ 3.08 (s, 3H), 6.64 (d, J=7.0 Hz, 1H), 6.71 (s, 1H), 7.42–7.52 (m, 5H), 8.04–8.06 (m, 2H);

LC-MS (retention time: 1.21 min, method B), MS m/z 237 (M$^+$+H).

Step 2:

A solution of 6-methyl-2-phenyl-pyrido[1,2a]pyrimidin-4-one (489 mg, 2.07 mmol) in melted diphenyl ether (5 mL) was heated to gentle reflux for 5 h. After cooling to the ambient temperature, the formed suspension was diluted with diethyl ether (10 mL), filtered. The cake was washed with diethyl ether thoroughly to afford 450 mg (92%) of the desired product as a brownish solid.

LC-MS (retention time: 1.25 min, method B), MS m/z 237 (M$^+$+H).

Step 3:

A suspension of 7-methyl-2-phenyl-1H-[1,8]naphthyridin-4-one (450 mg, 1.91 mmol) in POCl$_3$ (10 mL) was heated to gentle reflux for 3 h. Evaporated in vacuo. The residue was was poured into iced water (20 mL) and neutralized to pH 10 with 10 M NaOH. Extracted with CHCl$_3$. The organic layer was washed with brine, dried over MgSO$_4$, filtered, evaporated. The residue was purified by flash chromatography (2:1 hexane-EtOAc) to afford 450 mg (92%) of the desired product as a pink solid.

$^1$H NMR (CD$_3$OD) δ 2.80 (s, 3H), 7.54–7.56 (m, 3H), 7.61 (d, J=8.4 Hz, 1H), 8.25–8.30 (m, 3H), 8.58 (d, J=8.4 Hz, 1H);

LC-MS (retention time: 1.39 min, method B), MS m/z 255, 257 (M$^+$+H).

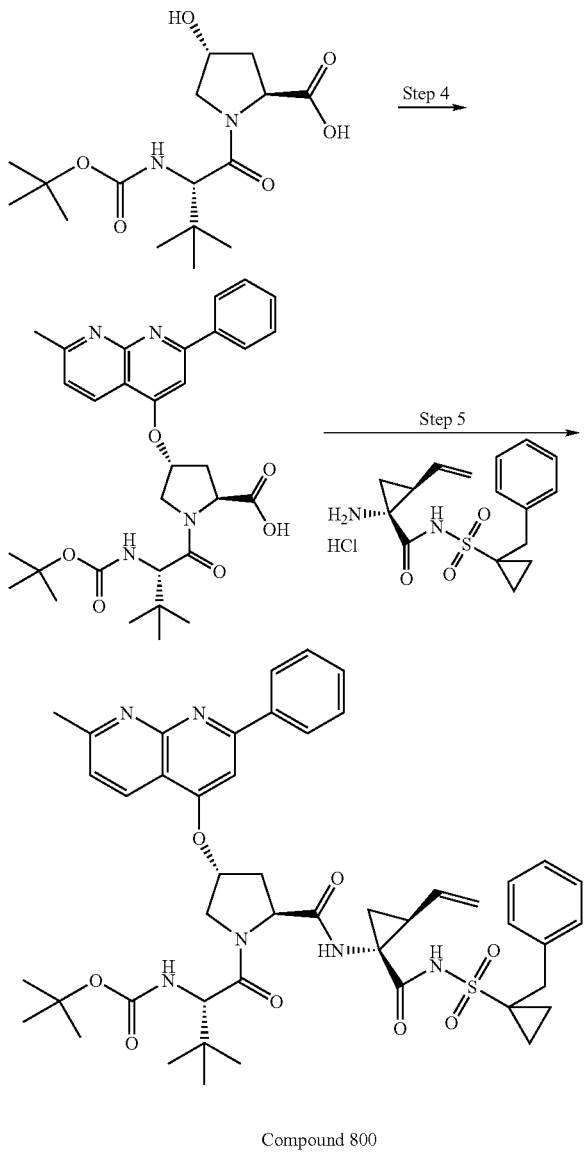

Scheme 2

Compound 800

Step 4:

This product was prepared by the same procedure as described in Example 500.

LC-MS (retention time: 1.55 min, method B), MS m/z 563 (M$^+$+H).

Step 5:

Compound 800 was prepared by the same procedure as described in Example 500, Step 6, except using the product of Example 800, Step 4 instead.

$^1$H NMR (CD$_3$OD) δ 0.64 (b, 2H), 0.98 (s, 9H), 1.26 (s, 9H), 1.45–1.47 (m, 3H), 1.91–1.94 (m, 1H), 2.28–2.32 (m, 2H), 2.71–2.77 (m, 4H), 4.08–4.10 (m, 1H), 4.21 (b, 1H), 4.56–4.61 (m, 2H), 5.17 (d, J=10 Hz, 1H), 5.32 (d, J=15 Hz, 1H), 5.63 (b, 1H), 5.73–5.79 (m, 1H), 7.14–7.15 (m, 2H), 7.24–7.30 (m, 3H), 7.41–7.43 (m, 1H), 7.53–7.55 (m, 4H), 8.22–8.24 (m, 2H), 8.56 (d, J=10 Hz, 1H);

LC-MS (retention time: 1.87 min, method B), MS m/z 865 (M$^+$+H).

The following conditions were used for LC/MS analysis.
Columns: Method A: YMC ODS-A C18 S7 (4.6×33 mm)
Method B: YMC Xterra ODS S7 (3.0×50 mm)
Method C: Xterra ms C18 (4.6×33 mm)
Method D: YMC ODS C18 S3 (4.6×33 mm)
Gradient: 100% solvent A/0% solvent B to 0% solvent A/100% solvent B
Gradient time: 3 min.
Hold Time: 1 min.
Flow Rate: 5 mL/min.
Detector Wavelength: 220 nm.
Solvents: Solvent A: 10% MeOH/90% water/0.1% TFA.
Solvent B: 90% MeOH/10% water/0.1% TFA.

The following conditions were used for prep-HPLC separation.
Columns: Phenomenex-Luna 30×100 mm, S5
Gradient: 60% solvent A/40% solvent B to 0% solvent A/100% solvent B
Gradient time: 15 min.
Stop Time: 20 min.
Flow Rate: 30 mL/min.
Detector Wavelength: 220 nm.
Solvents: Solvent A: 10% MeOH/90% water/0.1% TFA.
Solvent B: 90% MeOH/10% water/0.1% TFA.

Section J

Biological Studies

Recombinant HCV NS3/4A Protease Complex FRET Peptide Assay

The purpose of this in vitro assay was to measure the inhibition of HCV NS3 protease complexes, derived from the BMS strain, H77 strain or J4L6S strain, as described below, by compounds of the present invention. This assay provides an indication of how effective compounds of the present invention would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738–8743 (1997); AF054247, see Yanagi, M., St Claire, M., Shapiro, M., Emerson, S. U., Purcell, R. H. and Bukh, J, Virology 244 (1), 161–172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17): 5620–32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A protein complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8): 6758–69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride ($MgCl_2$), 1 μg/ml DnaseI, 5 mM β-Mercaptoethanol (βME), Protease inhibitor—Ethylenediamine Tetraacetic acid (EDTA) free (Roche), homogenized and incubated for 20 minutes (min) at 4° C. The homogenate was sonicated and clarified by ultra-centrifugation at 235000 g for 1 h at 4° C. Imidazole was added to the supernatant to a final concentration of 15 mM and the pH adjusted to 8.0. The crude protein extract was loaded on a Nickel—Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay was RET S1 (Resonance Energy Transfer Depsipeptide Substrate; AnaSpec, Inc. cat # 22991) (FRET peptide), described by Taliani et al. in Anal. Biochem. 240(2): 60–67 (1996). The sequence of this peptide is loosely based on the NS4A/NS4B natural cleavage site for the HCV NS3 protease except there is an ester linkage rather than an amide bond at the cleavage site. The peptide substrate was incubated with one of the three recombinant NS3/4A protease complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2–3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present invention in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel X1-fit software using the equation, $y=A+((B-A)/(1+((C/x)^{\wedge}D)))$.

All of the compounds tested were found to inhibit the activity of the NS3/4A protease complex with IC50's of 1.2 μM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present invention in inhibiting HCV NS3/4A protease complex as compared to other serine or cysteine proteases.

The specificities of compounds of the present invention were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (PCT Patent Application No. WO 00/09543) with some modifications to the serine protease assays. All enzymes were purchased from Sigma while the substrates were from Bachem.

Each assay included a 2 h enzyme-inhibitor pre-incubation at room temperature followed by addition of substrate and hydrolysis to ~30% conversion as measured on a Spectramax Pro microplate reader. Compound concentrations varied from 100 to 0.4 μM depending on their potency.

The final conditions for each assay were as follows:
50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with:
133 μM succ-AAA-pNA and 20 nM HNE or 8 nM PPE;
100 μM succ-AAPF-pNA and 250 pM Chymotrypsin.

100 mM NaHPO$_4$ (Sodium Hydrogen Phosphate) pH 6, 0.1 mM EDTA, 3% DMSO, 1 mM TCEP (Tris(2-carboxyethyl)phosphine hydrochloride), 0.01% Tween-20, 30 µM Z-FR-pNA and 5 nM Cathepsin B (enzyme stock activated in buffer containing 20 mM TCEP before use).

The percentage of inhibition was calculated using the formula:

[1−((UV$_{inh}$−UV$_{blank}$)/(UV$_{ctl}$−UV$_{blank}$))]×100

A non-linear curve fit was applied to the inhibition-concentration data, and the 50% effective concentration (IC$_{50}$) was calculated by the use of Excel X1-fit software.

Generation of HCV Replicon

An HCV replicon whole cell system was established as described by Lohmann V, Komer F, Koch J, Herian U, Theilmann L, Bartenschlager R., Science 285(5424): 110–3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was generated encoding the 5' internal ribosome entry site (IRES), the neomycin resistance gene, the EMCV (encephalomyocarditis viurs)-IRES and the HCV nonstructural proteins, NS3-NS5B, and 3' non-translated region (NTR). In vitro transcripts of the cDNA were transfected into the human hepatoma cell line, Huh7. Selection for cells constitutively expressing the HCV replicon was achieved in the presence of the selectable marker, neomycin (G418). Resulting cell lines were characterized for positive and negative strand RNA production and protein production over time.

FRET Assay

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before (1.5×10$^4$ cells/well) in 96-well tissue-culture sterile plates. Compound and no compound controls were prepared in DMEM containing 4% FCS, 1:100 Penicillin/Streptomysin, 1:100 L-glutamine and 5% DMSO in the dilution plate (0.5% DMSO final concentration in the assay). Compound/DMSO mixes were added to the cells and incubated for 4 days at 37° C. After 4 days, plates were rinsed thoroughly with Phosphate-Buffered Saline (PBS) (3 times 150 µl). The cells were lysed with 25 µl of a lysis assay reagent containing the FRET peptide (RET S1, as described for the in vitro enzyme assay). The lysis assay reagent was made from 5× cell Luciferase cell culture lysis reagent (Promega #E153A) diluted to 1× with distilled water, NaCl added to 150 mM final, the FRET peptide diluted to 10 µM final from a 2 mM stock in 100% DMSO. The plate was then placed into the Cytofluor 4000 instrument which had been set to 340 nm excitation/490 nm emission, automatic mode for 21 cycles and the plate read in a kinetic mode. EC$_{50}$ determinations were carried out as described for the IC$_{50}$ determinations.

Luciferase Assay

As a secondary assay, EC$_{50}$ determinations from the replicon FRET assay were confirmed in a luciferase reporter assay. Utilization of a replicon luciferase reporter assay was first described by Krieger et al (Krieger N, Lohmann V, and Bartenschlager R, J. Virol. 75(10): 4614–4624 (2001)). The replicon construct described for our FRET assay was modified by replacing the resistance gene neomycin with the Blasticidin-resistance gene fused to the N-terminus of the humanized form of *Renilla* luciferase (restriction sites Asc1/Pme1 used for the subcloning). The adaptive mutation at position 1179 (serine to isoleucine) was also introduced (Blight K J, Kolykhalov, A A, Rice, C M, Science 290 (5498): 1972–1974). The luciferase reporter assay was set up by seeding huh7 cells the night before at a density of 2×10$^6$ cells per T75 flask. Cells were washed the next day with 7.5 ml Opti-MEM. Following the Invitrogen protocol, 40 µl DMRIE-C was vortexed with 5 ml Opti-MEM before adding 5 µg HCV reporter replicon RNA. The mix was added to the washed huh7 cells and left for 4 h at 37° C. In the mean time, serial compound dilutions and no compound controls were prepared in DMEM containing 10% FCS and 5% DMSO in the dilution plate (0.5% DMSO final concentration in the assay). Compound/DMSO mixes were added to each well of a 24-well plate. After 4 h, the transfection mix was aspirated, and cells washed with 5 ml of Opti-MEM before trypsinization. Trypsinized cells were resuspended in 10% DMEM and seeded at 2×10$^4$ cells/well in the 24-well plates containing compound or no compound controls. Plates were incubated for 4 days. After 4 days, media was removed and cells washed with PBS. 100 µl 1×*Renilla* Luciferase Lysis Buffer (Promega) was immediately added to each well and the plates either frozen at −80° C. for later analysis, or assayed after 15 min of lysis. Lysate (40 µl) from each well was transferred to a 96-well black plate (clear bottom) followed by 200 µl 1×*Renilla* Luciferase assay substrate. Plates were read immediately on a Packard Top-Count NXT using a luminescence program.

The percentage inhibition was calculated using the formula below:

$$\% \text{ control} = \frac{\text{average luciferase signal in experimental wells (+compound)}}{\text{average luciferase signal in DMSO control wells (−compound)}}$$

The values were graphed and analyzed using XLFit to obtain the EC$_{50}$ value.

Compounds in accordance with the present invention were tested for biological activity as described above and found to have activities in the ranges as follow:

IC50 Activity Ranges (NS3/4A BMS Strain): A is 10–100 micromolar (µM); B is 1–10 µM; C is 0.1–1 µM; D is <0.1 µM EC50 Activity Range (for compounds tested): A is 10–100 µM; B is 1–10 µM; C is 0.1–1 µM; D is <0.1 µM Note that by using the Patent example number and the Patent compound number shown in Table 2, the structures of compounds can be found herein.

In accordance with the present invention, preferably the compounds have a biological activity (EC$_{50}$) of 100 µM or less, more preferably 1 µM or less and most preferably 100 nM or less.

TABLE 2

| Example number, Compound number | Biological activity | |
|---|---|---|
| | IC50 (uM) | EC50 (uM) |
| Ex 100, Cpd 100 | D | D |
| Ex 101, Cpd 101 | D | D |
| Ex 102, Cpd 102 | D | C |
| Ex 103, Cpd 103 | D | C |
| Ex 104, Cpd 104 | D | C |
| Ex 105, Cpd 105 | D | D |

TABLE 2-continued

Biological activity

| Example number, Compound number | IC50 (uM) | EC50 (uM) |
|---|---|---|
| Ex 106, Cpd 106 | D | D |
| Ex 107, Cpd 107 | D | D |
| Ex 108, Cpd 108 | D | D |
| Ex 109, Cpd 109 | D | D |
| Ex 110, Cpd 110 | D | D |
| Ex 111, Cpd 111 | D | D |
| Ex 112, Cpd 112 | D | C |
| Ex 113, Cpd 113 | D | C |
| Ex 217, Cmpd 217 | D | D |
| Ex 218, Cmpd 218 | D | D |
| Ex 219, Cmpd 219 | D | D |
| Ex 220, Cmpd 220 | D | C |
| Ex 201, Cmpd 201 | B | |
| Ex 200, Cmpd 200 | B | |
| Ex 202, Cmpd 202 | B | |
| Ex 203, Cmpd 203 | B | |
| Ex 204, Cmpd 204 | B | |
| Ex 205, Cmpd 205 | C | C |
| Ex 206, Cmpd 206 | C | |
| Ex 207, Cmpd 207 | B | |
| Ex 208, Cmpd 208 | B | |
| Ex 209, Cmpd 209 | A | B |
| Ex 210, Cmpd 210 | B | |
| Ex 211, Cmpd 211 | B | |
| Ex 212, Cmpd 212 | B | |
| Ex 213, Cmpd 213 | A | |
| Ex. 300. Cmpd 300 | D | D |
| Ex. 301. Cmpd 301 | D | D |
| Ex. 302 Cmpd 302 | D | D |
| Ex. 303 Cmpd 303 | C | C |
| Ex. 304 Cmpd 304 | D | D |
| Ex 400, Cmpd 400 | D | C |
| Ex 401, Cmpd 401 | C | C |
| Ex 500, Cmpd 500 | D | C |
| Ex 501, Cmpd 501 | D | C |
| Ex 502, Cmpd 502 | C | C |
| Ex 600, Cmpd 600 | D | D |
| Ex 601, Cmpd 601 | D | C |
| Ex 602, Cmpd 602 | C | B |
| Ex 603, Cmpd 603 | B | |
| Ex 604, Cmpd 604 | D | C |
| Ex 605, Cmpd 605 | C | B |
| Ex 700, Cmpd 700 | D | D |
| Ex 701, Cmpd 701 | D | C |
| Ex 800, Cmpd 800 | D | C |

Those skilled in the art will recognize that although the invention has been described above with respect to specific aspects, other aspects are intended to be within the scope of the claims which follow. All documents referenced herein are hereby incorporated by reference as if set out in full.

What is claimed is:

1. A compound having the formula

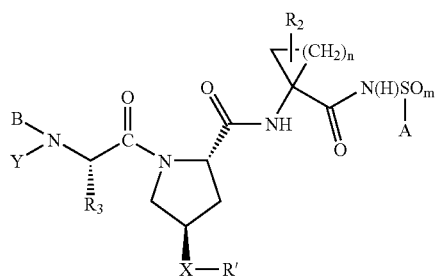

wherein:

(a) A is

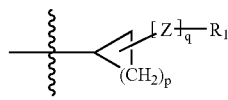

z is

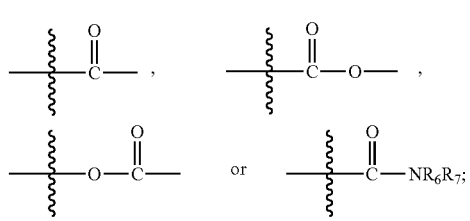

p is 1, 2 or 3;

q is 0 or 1;

$R_1$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het; or $R_1$ is trialkylsilane or halogen, provided q is 0;

(b) m is 1 or 2;

(c) n is 1 or 2;

(d) $R_2$ is H, $C_{1-6}$ alkyl, $C_{2-6}$ alkenyl or $C_{3-7}$ cycloalkyl, each optionally substituted with halogen;

(e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;

(g) B is H, $C_{1-6}$ alkyl, $R_4$—(C=O)—, $R_4$O(C=O)—, $R_4$—N($R_5$)—C(=O)—, $R_4$—N($R_5$)—C(=S)—, $R_4$SO$_2$—, or $R_4$—N($R_5$)—SO$_2$—;

(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, methoxy, CF$_3$, halogen, nitro, hydroxy, amido, (lower alkyl) amido, or amino optionally substituted with $C_{1-6}$ alkyl; (iv) Het; (v) bicyclo(1.1.1) pentane; or (vi) —C(O)OC$_{1-6}$ alkyl, $C_{2-6}$alkenyl or $C_{2-6}$ alkynyl;

(i) $R_5$ is H; $C_{1-6}$ alkyl optionally substituted with 1–3 halogens; or $C_{1-6}$ alkoxy provided $R_4$ is $C_{1-10}$ alkyl;

(j) X is O, S, SO, $SO_2$, $OCH_2$, $CH_2O$ or NH;

(k) R' is Het, $C_{6-10}$ aryl or $C_{7-14}$ alkylaryl, each optionally substituted with $R^a$; provided that when R' is Het, the Het is other than unsubstituted, monosubstituted, or disubstituted quinoline; and (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, trifluoromethoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, di ($C_{1-6}$) alkyl(alkoxy)amine, $C_{6-10}$ aryl, $C_{7-14}$ alkylaryl, or a 5–7 membered monocyclic heterocycle; and (m) $R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl;

or a pharmaceutically acceptable enantiomer, diastereomer, salt, solvate or prodrug thereof.

2. The compound of claim 1 wherein

A is

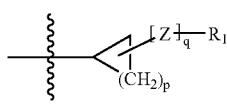

z is

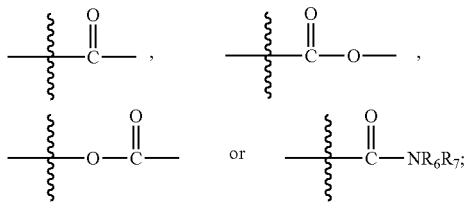

p is 1, 2 or 3;

q is 0 or 1;

$R_1$ is $C_{3-7}$ cycloalkyl, $C_{4-7}$ cycloalkenyl; $C_{7-14}$ alkylaryl; $C_{7-14}$ alkylaryloxy; $C_{8-15}$ alkylarylester; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{6-10}$ aryloxy, $C_{8-15}$ alkylarylester or Het; or $R_1$ is trialkylsilane or halogen, provided q is 0; and $R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl.

3. The compound of claim 1 wherin $R_2$ is $C_{1-6}$ alkyl, $C_{2-6}$ alkenyl or $C_{3-7}$ cycloalkyl.

4. The compound of claim 3 wherein $R_2$ is $C_{2-6}$ alkenyl.

5. The compound of claim 1 wherein $R_3$ is $C_{1-8}$ alkyl optionally substituted with $C_6$aryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl; or $C_{4-10}$ alkylcycloalkyl.

6. The compound of claim 5 wherein $R_3$ is $C_{1-8}$ alkyl optionally substituted with $C_{1-6}$ alkoxy; or $C_{3-7}$ cycloalkyl.

7. The compound of claim 1 wherein Y is H.

8. The compound of claim 1 wherein B is H, $C_{1-6}$ alkyl, $R_4$—(C=O)—, $R_4O(C=O)$—, $R_4$—$N(R_5)$—C(=O)—, $R_4$—$N(R_5)$—C(=S)—, $R_4SO_2$—, or $R_4$—$N(R_5)$—$SO_2$—.

9. The compound of claim 8 wherein B is $R_4$—(C=O)—, $R_4O(C=O)$—, or $R_4$—$N(R_5)$—C(=O)—.

10. The compound of claim 9 wherein B is $R_4O(C=O)$— and $R_4$ is $C_{1-6}$ alkyl.

11. The compound of claim 1 wherein $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl, methoxy, $CF_3$, or halogen.

12. The compound of claim 11 wherein $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl.

13. The compound of claim 1 wherein $R_5$ is H or $C_{1-6}$ alkyl optionally substituted with 1–3 halogens.

14. The compound of claim 13 wherein $R_5$ is H.

15. The compound of claim 1 wherein X is O or NH.

16. The compound of claim 15 wherein R' is Het; or $C_{6-10}$ aryl optionally substituted with $R^a$, provided that when R' is Het, the Het is other than unsubstituted, monosubstituted, or disubstituted quinoline.

17. The compound of claim 16 wherein R' is Het, provided the Het is other than unsubstituted, monosubstituted, or disubstituted quinoline.

18. The compound of claim 17 wherein the heterocycle contains 1 or 2 nitrogen atoms and optionally a sulfur atom or an oxygen atom in the ring, provided that the heterocycle is other than unsubstituted, monosubstituted, or disubstituted quinoline.

19. The compound of claim 18 wherein the heterocycle is substituted with at least one of $C_{1-6}$ alkyl, $C_{1-6}$ alkoxy, trifluoromethoxy, halo, $C_{6-10}$ aryl, $C_{7-14}$ alkylaryl, or a 5–7 membered monocyclic heterocycle.

20. The compound of claim 1 wherein $R^a$ is $C_{1-6}$ alkyl, $C_{3-7}$ cycloalkyl, $C_{1-6}$ alkoxy, halo-$C_{1-6}$ alkyl, trifluoromethoxy, halo, amino, $C_6$ aryl, or a 5–7 membered monocyclic heterocycle.

21. A compound having the formula

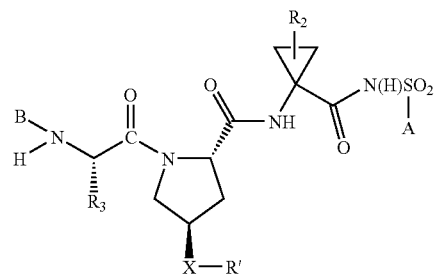

(II)

wherein:

(a) A is

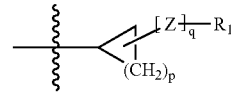

z is

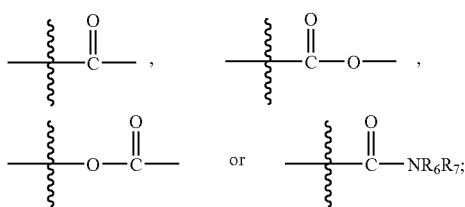

p is 1, 2 or 3;
q is 0 or 1; and
$R_1$ is $C_{3-7}$ cycloalkyl, $C_{4-7}$ cycloalkenyl; $C_{7-14}$ alkylaryl; $C_{7-14}$ alkylaryloxy; $C_{8-15}$ alkylarylester; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{6-10}$ aryloxy, $C_{8-15}$ alkylarylester or Het; or $R_1$ is trialkylsilane or halogen, provided q is 0;
(b) $R_2$ is $C_{1-6}$ alkyl, $C_{2-6}$ alkenyl or $C_{3-7}$ cycloalkyl;
(c) $R_3$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl;
(d) Y is H;
(e) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;
(f) $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl, methoxy, $CF_3$, or halogen;
(g) $R_5$ is H or $C_{1-6}$ alkyl optionally substituted with 1–3 halogens;
(h) X is O or NH;
(i) R' is Het; or $C_{6-10}$ aryl optionally substituted with $R^a$, provided that when R' is Het, the Het is other than unsubstituted, monosubstituted, or disubstituted quinoline;
(j) $R^a$ is $C_{1-6}$ alkyl, $C_{3-7}$ cycloalkyl, $C_{1-6}$ alkoxy, trifluoromethoxy, halo-$C_{1-6}$ alkyl, halo, amino, $C_6$ aryl, or a 5–7 membered monocyclic heterocycle; and
(k) $R_6$ and $R_7$ are each independently H; or $C_{1-6}$ alkyl, $C_{2-10}$ alkenyl or $C_{6-10}$ aryl, each of which may be optionally substituted with halo, cyano, nitro, $C_{1-6}$ alkoxy, amido, amino or phenyl;
or a pharmaceutically acceptable enantiomer, diastereomer salt, solvate or prodrug thereof.

22. The compound of claim 21 wherein R' is a bicyclic heterocycle, provided that the heterocycle is other than unsubstituted, monosubstituted, or disubstituted quinoline.

23. The compound of claim 22 wherein the heterocycle contains 1 or 2 nitrogen atoms and optionally a sulfur atom or an oxygen atom in the ring, provided that the heterocycle is other than unsubstituted, monosubstituted, or disubstituted quinoline.

24. The compound of claim 22 wherein the heterocycle is substituted with at least one of $C_{1-6}$ alkyl, $C_{1-6}$ alkoxy, halo, $C_6$ aryl, and a 5–7 membered monocyclic heterocycle.

25. The compound of claim 21 wherein R' is a bicyclic heterocycle containing 1 nitrogen atom and substituted with methoxy and at least one of a $C_6$ aryl and a 5–7 membered monocyclic heterocycle, provided that the heterocycle is other than unsubstituted quinoline.

26. The compound of claim 21 wherein R' is a monocyclic heterocycle.

27. The compound of claim 26 wherein the heterocycle contains 1 or 2 nitrogen atoms and optionally a sulfur atom or an oxygen atom in the ring.

28. The compound of claim 26 wherein the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle.

29. The compound of claim 21 wherein R' is a monoyclic heterocycle containing 1 or 2 nitrogen atoms and substituted with methoxy and at least one of a $C_6$ aryl and a 5–7 membered monocyclic heterocycle.

30. A compound having the formula

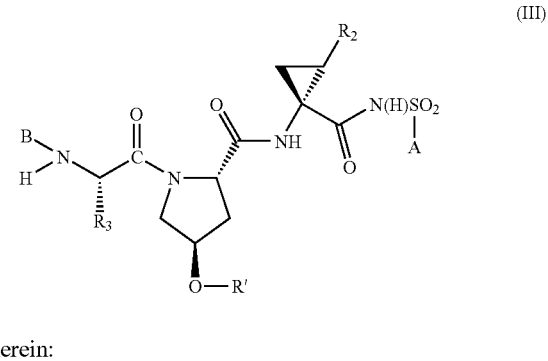

(III)

wherein:
(a) A is

p is 1, 2 or 3;
$R_1$ is $C_{7-14}$ alkylaryl; $C_{1-8}$ alkyl optionally substituted with $C_{1-6}$ alkoxy, $C_{2-10}$ alkenyl or $C_{4-10}$ alkylcycloalkyl; or $R_1$ is trialkylsilane or halogen;
(b) $R_2$ is $C_{2-6}$ alkenyl;
(c) $R_3$ is $C_{1-8}$ alkyl;
(e) B is $R_4O(C=O)$—, or $R_4$—N(H)—C(=O)—;
(f) $R_4$ is $C_{1-10}$ alkyl;
(g) R' is a bicyclic heterocycle optionally substituted with $R^a$, provided that the heterocycle is other than unsubstituted, monosubstituted, or disubstituted quinoline; and
(h) $R^a$ is $C_{1-6}$ alkyl, $C_{1-6}$ alkoxy, halo, trifluoromethoxy, $C_6$ aryl, or a 5–7 membered monocyclic heterocycle;
or a pharmaceutically acceptable enantiomer, diastereomer salt, solvate or prodrug thereof.

31. The compound of claim 30 wherein $R_1$ is cyclopropyl or cyclobutyl.

32. The compound of claim 30 wherein $R_2$ is vinyl.

33. The compound of claim 30 wherein $R_3$ is t-butyl.

34. The compound of claim 30 wherein $R_4$ is t-butyl.

35. The compound of claim 30 wherein R' is isoquinoline optionally substituted with $R^a$.

36. The compound of claim 30 wherein $R_1$ is cyclopropyl, $R_2$ is vinyl, $R_3$ is t-butyl, $R_4$ is t-butyl, and R' is isoquinoline substituted with $R^a$.

37. The compound of claim 36 wherein $R^a$ is $C_{1-6}$ alkoxy.

38. The compound of claim 37 wherein $R^a$ further includes at least one of $C_6$ aryl or a 5–7 membered monocyclic heterocycle.

39. A composition comprising the compound of claim 1 and a pharmaceutically acceptable carrier.

40. The composition according to claim 39 further comprising a compound having anti-HCV activity.

41. The composition according to claim 40 wherein the compound having anti-HCV activity is an interferon.

42. The composition according to claim 41 wherein the interferon is selected from the group consisting of interferon alpha 2B, pegylated interferon alpha, consensus interferon, interferon alpha 2A, and lymphoblastiod interferon tau.

43. The composition according to claim 40 wherein the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

44. The composition according to the claim 39 further comprising an interferon and ribavirin.

45. A method of inhibiting the function of the HCV serine protease comprising contacting the HCV serine protease with the compound of claim 1.

46. A method of treating an HCV infection in a patient, comprising administering to the patient a therapeutically effective amount of the compound of claim 1, or a pharmaceutically acceptable enantiomer, diastereomer, solvate, prodrug or salt thereof.

47. The method according to claim 46 wherein the compound is effective to inhibit the function of the HCV NS5B protein.

48. The method according to claim 46 further comprising administering another compound having anti-HCV activity prior to, after or simultaneously with the compound of claim 1.

49. The method according to claim 48 wherein the other compound having anti-HCV activity is an interferon.

50. The method according to claim 49 wherein the interferon is selected from the group consisting of interferon alpha 2B, pegylated interferon alpha, consensus interferon, interferon alpha 2A, lymphoblastiod interferon tau.

51. The method according to claim 48 wherein the other compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

52. The method according to claim 51 wherein the compound having anti-HCV activity is a small molecule.

53. The method according to claim 52 wherein the compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

54. The method according to claim 48 wherein the other compound having anti-HCV activity is effective to inhibit the function of target in the HCV life cycle other than the HCV NS5B protein.

* * * * *

UNITED STATES PATENT AND TRADEMARK OFFICE
CERTIFICATE OF CORRECTION

PATENT NO. : 7,135,462 B2  Page 1 of 1
APPLICATION NO. : 10/992548
DATED : November 14, 2006
INVENTOR(S) : Paul Michael Scola et al.

It is certified that error appears in the above-identified patent and that said Letters Patent is hereby corrected as shown below:

Col. 153 Claim 2, lines 32-43, "z is [structure] " should be -- z is [structure] --.

Col. 154 Claim 11, line 11, "hydroxy, $C_{1-6}$alkoxy;" should be --hydroxy, or $C_{1-6}$alkoxy--.

Col. 155 Claim 21, column 155, lines 1-12, "z is [structure] " should be -- z is [structure] --.

Signed and Sealed this

Third Day of April, 2007

JON W. DUDAS
*Director of the United States Patent and Trademark Office*